US 12,429,428 B2

(12) United States Patent
Heron et al.

(10) Patent No.: US 12,429,428 B2
(45) Date of Patent: Sep. 30, 2025

(54) LATERAL FLOW BODILY FLUID TESTING SYSTEM AND METHOD

(71) Applicant: TestCard Ltd., East Ayton (GB)

(72) Inventors: Luke Heron, Brompton by Sawdon (GB); Andrew Botham, Brompton by Sawdon (GB); Christopher Hewitt, Brompton by Sawdon (GB)

(73) Assignee: TestCard Ltd., East Ayton (GB)

( * ) Notice: Subject to any disclaimer, the term of this patent is extended or adjusted under 35 U.S.C. 154(b) by 828 days.

(21) Appl. No.: 17/633,909

(22) PCT Filed: Jun. 4, 2020

(86) PCT No.: PCT/GB2020/051341
§ 371 (c)(1),
(2) Date: Feb. 8, 2022

(87) PCT Pub. No.: WO2021/023960
PCT Pub. Date: Feb. 11, 2021

(65) Prior Publication Data
US 2022/0291205 A1     Sep. 15, 2022

(30) Foreign Application Priority Data

Aug. 8, 2019 (GB) ......................................... 1911371
Aug. 8, 2019 (GB) ......................................... 1911372
(Continued)

(51) Int. Cl.
*B01L 3/00* (2006.01)
*A61B 5/145* (2006.01)
(Continued)

(52) U.S. Cl.
CPC ..... *G01N 21/8483* (2013.01); *A61B 5/14507* (2013.01); *A61B 5/1477* (2013.01);
(Continued)

(58) Field of Classification Search
CPC .. G01N 21/8483; G01N 21/78; G01N 33/493; G01N 33/521; G01N 33/54388;
(Continued)

(56) References Cited

U.S. PATENT DOCUMENTS

| 2013/0136347 A1* | 5/2013 | Wachtell | G06T 7/90 |
| | | | 382/162 |
| 2014/0170757 A1* | 6/2014 | Tsai | G01N 21/8483 |
| | | | 436/55 |

(Continued)

FOREIGN PATENT DOCUMENTS

| JP | 2012225864 | 11/2012 |
| JP | 2015197399 | 11/2015 |

(Continued)

OTHER PUBLICATIONS

Notification of Reasons for Rejection from related Japan Patent Application No. 2022-507885, dated Mar. 22, 2023, 4 pages.

(Continued)

*Primary Examiner* — Jennifer Wecker
*Assistant Examiner* — Oyeleye Alexander Alabi
(74) *Attorney, Agent, or Firm* — Brooks, Cameron & Huebsch, PLLC

(57) ABSTRACT

A lateral flow bodily fluid testing system is provided. The system comprises an application-analysable bodily fluid testing equipment (100, 200, 300) and an electronic device (1001) comprising a camera (1002) and one or more processors (1004). The one or more processors are configured to acquire image data of the application-analysable bodily fluid testing equipment with the camera of the electronic device, perform testing of bodily fluid applied to the application-analysable bodily fluid testing equipment using the image data to determine whether indicators of one or more bodily conditions are present in the applied bodily fluid, and (Continued)

output a result indicating whether the indicators of one or more bodily conditions are present in the applied bodily fluid.

20 Claims, 24 Drawing Sheets

(30) Foreign Application Priority Data

Aug. 8, 2019 (GB) ...................................... 1911373
Aug. 8, 2019 (GB) ...................................... 1911376

(51) Int. Cl.
| | | |
|---|---|---|
| *A61B 5/1477* | (2006.01) | |
| *B01F 33/302* | (2022.01) | |
| *B01F 33/3033* | (2022.01) | |
| *B01L 7/00* | (2006.01) | |
| *B33Y 80/00* | (2015.01) | |
| *C12M 1/00* | (2006.01) | |
| *C12M 1/34* | (2006.01) | |
| *C12M 3/00* | (2006.01) | |
| *C12M 3/06* | (2006.01) | |
| *C12Q 1/6848* | (2018.01) | |
| *C12Q 1/686* | (2018.01) | |
| *G01N 21/29* | (2006.01) | |
| *G01N 21/77* | (2006.01) | |
| *G01N 21/78* | (2006.01) | |
| *G01N 21/84* | (2006.01) | |
| *G01N 33/493* | (2006.01) | |
| *G01N 33/52* | (2006.01) | |
| *G01N 33/543* | (2006.01) | |
| *G01N 35/00* | (2006.01) | |
| *G06T 7/00* | (2017.01) | |
| *G06T 7/73* | (2017.01) | |
| *G06T 7/90* | (2017.01) | |
| *G16H 10/40* | (2018.01) | |

(52) U.S. Cl.
CPC ............ *B01L 3/5023* (2013.01); *G01N 21/78* (2013.01); *G01N 33/493* (2013.01); *G01N 33/521* (2013.01); *G01N 33/54388* (2021.08); *G01N 35/00732* (2013.01); *G06T 7/0012* (2013.01); *G06T 7/73* (2017.01); *G06T 7/90* (2017.01); *G16H 10/40* (2018.01); *A61B 2562/0295* (2013.01); *B01L 2300/021* (2013.01); *B01L 2300/069* (2013.01); *G01N 2021/7759* (2013.01); *G01N 2035/00742* (2013.01); *G06T 2207/10024* (2013.01); *G06T 2207/30204* (2013.01)

(58) Field of Classification Search
CPC ..... G01N 35/00732; G01N 2021/7759; G01N 2035/00742; A61B 5/14507; A61B 5/1477; A61B 2562/0295; A61B 2576/00; B01L 3/5023; B01L 2300/021; B01L 2300/069; G06T 7/0012; G06T 7/73; G06T 7/90; G06T 2207/10024; G06T 2207/30204; G06T 2207/30024; G16H 10/40; Y02A 90/10
See application file for complete search history.

(56) References Cited

U.S. PATENT DOCUMENTS

| | | | | |
|---|---|---|---|---|
| 2016/0077091 | A1* | 3/2016 | Tyrrell | ................... G01N 33/94 422/403 |
| 2016/0232421 | A1* | 8/2016 | Decker | ................... G01N 21/78 |
| 2018/0259449 | A1 | 9/2018 | Poulsen et al. | |

FOREIGN PATENT DOCUMENTS

| | | |
|---|---|---|
| JP | 2016125875 | 7/2016 |
| JP | 2018525613 | 9/2018 |
| WO | 20190122883 | 6/2019 |

OTHER PUBLICATIONS

International Search Report and Written Opinion from related PCT Application No. PCT/GB2020/051341, dated Nov. 20, 2020, 4 pages.

\* cited by examiner

LATERAL FLOW BODILY FLUID TESTING SYSTEM AND METHOD

FIELD OF INVENTION

The present disclosure relates to bodily fluid testing equipment and more specifically bodily fluid testing equipment analysable using a device-based application.

BACKGROUND

Bodily fluids, such as urine, are typically tested at a medical establishment such as a hospital. Such testing requires a patient to visit a doctors' surgery or hospital to deposit a sample of bodily fluid, and then wait for results. In many cases, waiting for the results can take several days.

Application-analysable prior art testing equipment is required to be laid on a flat surface for the analysis to be carried out. This can lead to both contamination of the surface from the bodily fluid, and contamination of sensitive testing equipment by any contaminants on the surface. Application-analysable prior art testing equipment also requires a reference colour pad to be placed under the testing equipment; such a two-part system cannot be efficiently packaged and stored. Application-analysable prior art testing equipment also requires reference colours to be presented on the testing equipment; this can add additional size to the equipment thereby preventing the equipment from being efficiently packaged and stored.

There is a need to provide a more user-friendly and efficient process for bodily fluid testing. An object of the present invention is, therefore, to address such a challenge.

SUMMARY

In a first aspect, there is provided an application-analysable bodily fluid testing equipment, the equipment comprising:
  at least one testing region sensitive to an indicator of a bodily condition in bodily fluid from which image data is capturable and analysable by an associated application on a device; and
  a handling indicator indicating an area of the equipment for a user to hold during the application of a bodily fluid to the at least one testing region, and during capture of the image data for analysis of the bodily fluid applied to the at least one testing region using the application on the device.

In this way, a user of the equipment can apply a bodily fluid, such as urine, to the testing region(s) of the equipment and then capture image data with an electronic device for analysis of the bodily fluid applied to the testing region(s), using an application executable on the device, without having to put the equipment down, or place it on a surface, between applying the bodily fluid and the analysis being carried out. This prevents contamination to the equipment from a surface, as well as preventing contamination to a surface from the bodily fluid applied to the equipment. This also improves hygiene. Preferably, the device may be a mobile device such as a smartphone or tablet computer. Preferably, the testing region may be a colour change pad testing region; colour change pad testing regions can be suitable for testing for bodily fluid indicators relating to conditions including urinary tract infections, diabetes, or glucose levels for diabetic screening or monitoring, and metabolic disorders, kidney disease, liver disease, dietary disorders, and pregnancy term complications, amongst others. Alternatively, the testing region may be a lateral flow testing region; lateral flow testing regions can be suitable for testing for bodily fluid indicators relating to pregnancy testing, drug misuse, and testing for hormones or antibodies in conditions where these provide diagnostic support such as ovulation health, prostate specific antigen levels, malaria, infertility, sexually transmitted infections, and diabetes HbA1c, amongst others.

Preferably, the handling indicator comprises indicia arranged on a surface of the equipment.

In this way, the indicia guide the user as to where the equipment should be held for optimal use.

Preferably the handling indicator comprises instructional text guiding the user to hold the equipment by the handling indicator.

In this way, the user can follow an instruction as to how to best hold the equipment for optimal use.

Preferably, the handling indicator further comprises a closed shape encompassing the instructional text.

In this way, the precise location of where to best hold the equipment for optimal use is conveyed to the user.

Preferably, the instructional text indicates for the user to place a thumb on the handling indicator.

Preferably, the handling indicator and the at least one testing region are both arranged on a same surface of the equipment.

In this way, rotating of the equipment and contortion of the user's wrist is negated, thereby improving the usability.

Preferably, the handling indicator is at least one of printed, embossed or debossed indicia on a surface of the equipment.

In this way, the handling indicator is clearly presented to the user, thereby aiding usability and reducing the likelihood of unintentional misuse.

Preferably, the equipment is planar in shape.

In this way the equipment can be efficiently packaged and occupy minimal space. This is especially advantageous for delivery by a postal surface as it allows for the equipment to be posted through a conventional letterbox.

Preferably, the handling indicator is arranged at an end portion of the equipment.

In this way, a user of the equipment can hygienically apply bodily fluid to the equipment and subsequently capture image data, such as a photograph or a scan, of the equipment using the application on a device without their hand obscuring the testing regions. Moreover, the position of the handling indicator encourages the user to carry out both actions without putting the equipment down in-between, thereby contributing to improved hygiene and reducing the risk of contamination.

Preferably, the equipment further comprises a support structure, wherein the handling indicator is on the support structure and the at least one testing region is mounted in a window of the support structure.

In this way, testing regions that use existing technologies can be mounted to the support structure to form the equipment. Moreover, a single design of support structure can be used for a variety of different types of testing region, i.e. different types of testing region relating to different conditions can be mounted to a single design of support structure. Only the type of testing region and any information presented on the support structure need be changed between manufacturing equipment designed for testing different conditions. This simplifies and streamlines manufacturing considerations. In another advantage, the window allows for the at least one testing region to be flush with a surface of the support structure such that the equipment has a consistent overall surface profile or height.

Preferably, the equipment is arranged for bodily fluid to be directly applied to the equipment during bodily expulsion by a user.

In this way, there is no risk of contamination to the bodily fluid before coming into contact with the testing region(s). Preferably, in such an arrangement, the testing region may be a colour change pad testing region. Colour change pad testing regions can be suitable for testing for bodily fluid indicators relating to conditions including urinary tract infections, diabetes, or glucose levels for diabetic screening or monitoring, and metabolic disorders, kidney disease, liver disease, dietary disorders, and pregnancy term complications, amongst others.

Preferably, the equipment is arranged for bodily fluid to be applied by dipping the equipment into a container housing a bodily fluid.

Preferably, in such an arrangement, the testing region may be a colour change pad testing region or a lateral flow testing region. Colour change pad testing regions can be suitable for testing for bodily fluid indicators relating to conditions including urinary tract infections, diabetes, or glucose levels for diabetic screening or monitoring, and metabolic disorders, kidney disease, liver disease, dietary disorders, and pregnancy term complications. Lateral flow testing regions can be suitable for testing for bodily fluid indicators relating to pregnancy testing, drug misuse, and testing for hormones or antibodies in conditions where these provide diagnostic support such as ovulation health, prostate specific antigen levels, malaria, infertility, sexually transmitted infections, and diabetes HbA1c, amongst others.

In this way, a user of the equipment can dip the equipment into a bodily fluid sample if, for example, they cannot expel the bodily fluid directly onto the equipment or if they are carrying out the process for a third party. This improves usability.

Preferably, the at least one testing region comprises a plurality of testing regions.

Preferably, each testing region of the plurality of testing regions may be designed to test for different conditions. In this way, a single application of bodily fluid can be used to identify the presence of indicators of relating to a plurality of conditions. For example, in the case of drug abuse identification, each of the multiple testing regions may relate to different types of drugs; a single application of bodily fluid can be used to test for the presence of multiple types of drug in the bodily system of a subject.

Preferably, the equipment further comprises a machine readable label arranged on a surface of the equipment.

In this way, a single application executable on the device can be arranged to carry out analysis for multiple tests relating to different conditions, and the application can determine the type of test that is being carried out from image data of the machine readable label captured by a camera of the device. Determining the type of test, before carrying out the analysis process, can expedite the analysis process as the application can more quickly identify what is to be analysed. Preferably the machine readable label may be a QR code. The machine readable label or information may also be used as an anchor point to aid the locating of the testing regions or sensitive regions, to provide LOT information including batch number and expiry date, for use in lighting conditions testing, to identify the date of manufacture and for a unique ID string. Preferably the machine readable label and the testing region(s) may be arranged on the same surface of the equipment.

Preferably, the equipment further comprises an integrity check incorporated to the equipment.

In this way, it can be determined whether the equipment has been used before, tampered with, or damaged, before use.

Preferably, the integrity check is a moisture identifier.

In an example, the moisture identifier is a leucocyte pad. Leucocyte pads are sensitive to moisture. In this way, the leucocyte pad can be used to indicate if the equipment has been used before, tampered with, or damaged, before use. Other examples of integrity checks include nitrite or protein pads.

Preferably, the bodily fluid is urine.

In this way, urinary indicators relating to conditions such as urinary tract infections, diabetes, or glucose levels for diabetic screening or monitoring, and metabolic disorders, kidney disease, liver disease, dietary disorders, pregnancy term complications, pregnancy testing, drug misuse, and testing for hormones or antibodies in conditions where these provide diagnostic support such as ovulation health, prostate specific antigen levels, malaria, infertility, sexually transmitted infections, and diabetes HbA1c, amongst others can be tested for.

In this way, a single application-analysable bodily fluid testing equipment, or a plurality of application-analysable bodily fluid testing equipments, can be sent to a user using postal services and can be received by the user by a conventional letterbox.

In a second aspect, there is provided a bodily fluid testing method using the application-analysable bodily fluid testing equipment of the first aspect, the method comprising:
- a user applying bodily fluid to the equipment whilst holding the equipment at the handling indicator;
- capturing image data of the equipment, using a camera of a device, whilst the user holds the equipment at the handling indicator; and
- an application executable on the device performing testing of the applied bodily fluid using the image data.

In this way, a user of the equipment can apply a bodily fluid, such as urine, to the testing region(s) of the equipment and then capture image data with an electronic device for analysis of the bodily fluid applied to the testing region(s), using an application executable on the device, without having to put the equipment down, or place it on a surface, between applying the bodily fluid and the analysis being carried out. This prevents contamination to the equipment from a surface, as well as preventing contamination to a surface from the bodily fluid applied to the equipment. This also improves hygiene. Preferably, the device may be a mobile device such as a smartphone or tablet computer.

In a third aspect, there is provided a system comprising the application-analysable bodily fluid testing equipment of the first aspect, and an application executable on a device arranged to perform testing of bodily fluid applied to the equipment using image data of the equipment captured by a camera of the device.

In this way, a user of the equipment can apply a bodily fluid, such as urine, to the testing region(s) of the equipment and then capture image data with an electronic device for analysis of the bodily fluid applied to the testing region(s), using an application executable on the device, without having to put the equipment down, or place it on a surface, between applying the bodily fluid and the analysis being carried out. This prevents contamination to the equipment from a surface, as well as preventing contamination to a surface from the bodily fluid applied to the equipment. This also improves hygiene. Preferably, the device may be a mobile device such as a smartphone or tablet computer.

In a fourth aspect, there is provided a method for determining an indicator of a bodily condition in an image of a bodily fluid testing equipment captured by an electronic device, the method comprising:

acquiring image data of a bodily fluid testing equipment, the bodily fluid testing equipment comprising one or more bodily fluid testing regions;

determining at least one edge of a first bodily fluid testing region of the one or more bodily fluid testing regions from the image data;

determining a location of the first bodily fluid testing region in the image data based upon a predetermined relationship between the at least one edge and a position of the first bodily fluid testing region;

sampling colour data of a sub-region of the first bodily fluid testing region based upon the determined location;

determining, based upon the sampled colour data, whether an indicator of a bodily condition has interacted with the first bodily testing region of the one or more bodily fluid testing regions; and providing an output, wherein the output is based upon whether the indicator of the bodily condition has interacted with the first bodily fluid testing region of the one or more bodily fluid testing regions.

In this way, the location of the one or more bodily fluid testing regions can be accurately determined. In particular, the location of the one or more bodily fluid testing regions can be determined without the need to use anchor points presented on the equipment. As such, anchor points are not required on the equipment thereby saving space on the equipment and allowing for a reduced size of equipment. Having determined the location of the first bodily fluid testing region, the determined location information can be used to ensure that the sub-region from the colour data sampled is within the bodily fluid testing region. This improves the accuracy of the determined output Preferably the electronic device may be a smartphone. Preferably the image data may be a photograph of the bodily fluid testing equipment. Preferably the bodily fluid testing region(s) may be a colour change pad(s) that changes colour in response to interaction with indicator(s) in bodily fluid. Preferably the bodily fluid may be urine.

Preferably, acquiring the image data comprises capturing the image data by a camera on the electronic device.

In this way, the user can capture the image data immediately following the application of a bodily fluid to the bodily fluid testing region(s). Preferably the image data may be captured in the form of a photograph.

Preferably, the method further comprises the method further comprises:

displaying, before the image data is captured, a live image of the bodily fluid testing equipment on a display of the electronic device using the camera of the electronic device;

displaying, before the image data is captured, a window on the display of the electronic device with the live image, wherein the bodily fluid testing equipment is alignable in the window.

In this way, the bodily fluid testing equipment can be accurately aligned in the image to aid the processing of the image.

Preferably, the window is arranged such that edges of the bodily fluid testing equipment are alignable with edges of the window.

In this way, the accuracy of the alignment of the bodily fluid testing equipment is improved.

Preferably, a machine readable label window is presented within the window and arranged such that a machine readable label on the bodily fluid testing equipment is alignable with the machine readable label window.

Preferably, the electronic device automatically captures image data of the bodily fluid testing equipment in response to identifying that the bodily fluid testing equipment is aligned in the window. Preferably, the electronic device automatically captures image data of the bodily fluid testing equipment in response to identifying that both the bodily fluid testing equipment is aligned in the window and the machine readable label is aligned in the machine readable label window.

In this way, the need for user input is minimised and the usability of the application is improved by reducing the risk of user error.

Preferably, the method further comprises determining a section of the bodily fluid testing equipment that includes the one or more bodily fluid testing regions.

In this way, a coarse identification of the approximate location of the one or more bodily fluid testing region can be determined. This approximation expedites the more precise identification using the predetermined relationship between the at least one edge and the position of the first bodily fluid testing region as the algorithm has narrower region in which to identify the at least one edge. Preferably, the determining of the section of the bodily fluid testing equipment that includes the one or more bodily fluid testing regions may be based upon a predetermined relationship. Preferably the predetermined relationship may be between the window in which the bodily fluid testing equipment is alignable and the section. Alternatively, or additionally, the predetermined relationship may be between a determined location of a machine readable label, by alignment with the machine readable label window, and the section.

Preferably, determining the at least one edge comprises determining a discontinuity in brightness between the testing region and a surrounding region indicative of the interface between the testing region and the surrounding region.

In this way, the location of the testing regions can be determined by the difference in brightness between the testing regions and the region surrounding the testing regions. Preferably, determining the at least one edge may further comprise scanning the determined section of the bodily fluid testing equipment.

Preferably, the determining at least one edge of the first bodily fluid testing region comprises determining two opposite edges of the first bodily fluid testing region, and the method further comprises determining the location of the first bodily fluid testing region as being confined between the two edges.

In this way, the accuracy of the determined location can be enhanced.

Preferably, the method further comprises presenting the output on a display of the electronic device.

In this way, a user of the bodily fluid testing equipment has immediate access to the results.

Preferably, the method is performed at the electronic device.

In this way, all of the processing can be carried out locally at the electronic device. This is particularly beneficial if, for example, a connection to a remote server is not available.

Preferably, subsequent to acquiring the image data the electronic device transmits the image data to a server, and the server performs the steps of:

determining at least one edge of a first bodily fluid testing region of the one or more bodily fluid testing regions from the image data;

determining a location of the first bodily fluid testing region in the image data based upon a predetermined relationship between the at least one edge and a position of the first bodily fluid testing region;

sampling colour data of a sub-region of the first bodily fluid testing region based upon the determined location;

determining, based upon the sampled colour data, whether an indicator of a bodily condition has interacted with the first bodily testing region of the one or more bodily fluid testing regions; and providing an output, wherein the output is based upon whether the indicator of the bodily condition has interacted with the first bodily fluid testing region of the one or more bodily fluid testing regions;

and wherein the method further comprises transmitting, by the server to the electronic device, instructions that instruct the electronic device to present a determined output, based upon the sampled colour data, on a display of the electronic device.

In this way, the processing can be carried out remotely at the server rather than locally at the electronic device. This is particularly advantageous for non-iOS devices which do not necessarily have a consistent colour spectrum between devices. By carrying out the processing at a server, a consistent colour spectrum can be used to ensure that consistent results are achieved. Preferably the server may utilise a Python application programming interface.

Preferably, the server further performs the step of determining a section of the bodily fluid testing equipment that includes the one or more bodily fluid testing regions.

Preferably, the determining of the section of the bodily fluid testing equipment that includes the one or more bodily fluid testing regions may be based upon a predetermined relationship. Preferably the predetermined relationship may be between the window in which the bodily fluid testing equipment is alignable and the section. Alternatively, or additionally, the predetermined relationship may be between a determined location of a machine readable label, by alignment with the machine readable label window, and the section.

Preferably, determining the at least one edge comprises determining a discontinuity in brightness between the testing region and a surrounding region indicative of the interface between the testing region and the surrounding region.

Preferably, the determining at least one edge of the first bodily fluid testing region comprises determining two opposite edges of the first bodily fluid testing region, and the server further performs the step of determining the location of the first bodily fluid testing region as being confined between the two edges.

In a fifth aspect, there is provided a non-transitory computer-readable medium storing instructions thereon that when executed by one or more processors of an electronic device cause the electronic device to perform the steps of:

acquiring image data of a bodily fluid testing equipment, the bodily fluid testing equipment comprising one or more bodily fluid testing regions;

determining at least one edge of a first bodily fluid testing region of the one or more bodily fluid testing regions from the image data;

determining a location of the first bodily fluid testing region in the image data based upon a predetermined relationship between the at least one edge and a position of the first bodily fluid testing region;

sampling colour data of a sub-region of the first bodily fluid testing region based upon the determined location;

determining, based upon the sampled colour data, whether an indicator of a bodily condition has interacted with the first bodily testing region of the one or more bodily fluid testing regions; and providing an output, wherein the output is based upon whether the indicator of the bodily condition has interacted with the first bodily fluid testing region of the one or more bodily fluid testing regions;

In this way, all of the processing can be carried out locally at the electronic device. This is particularly beneficial if, for example, a connection to a remote server is not available.

Preferably, acquiring the image data comprises capturing the image data by a camera on the electronic device;

Preferably the non-transitory computer-readable medium further stores instructions that when executed by the one or more processors cause the electronic device to perform the steps of displaying, before the image data is captured, a live image of the bodily fluid testing equipment on a display of the electronic device using the camera of the electronic device, and displaying, before the image data is captured, a window on the display of the electronic device with the live image, wherein the bodily fluid testing equipment is alignable in the window;

Preferably, the window is arranged such that edges of the bodily fluid testing equipment are alignable with edges of the window;

Preferably, a machine readable label window is presented within the window and arranged such that a machine readable label on the bodily fluid testing equipment is alignable with the machine readable label window.

Preferably, the non-transitory computer-readable medium further stores instructions that when executed by the one or more processors cause the electronic device to perform the step of automatically capturing image data of the bodily fluid testing equipment in response to identifying that the bodily fluid testing equipment is aligned in the window. Preferably, the electronic device automatically captures image data of the bodily fluid testing equipment in response to identifying that both the bodily fluid testing equipment is aligned in the window and the machine readable label is aligned in the machine readable label window.

Preferably, the non-transitory computer-readable medium further stores instructions that when executed by the one or more processors cause the electronic device to perform the step of determining a section of the bodily fluid testing equipment that includes the one or more bodily fluid testing regions. Preferably, the determining of the section of the bodily fluid testing equipment that includes the one or more bodily fluid testing regions may be based upon a predetermined relationship. Preferably the predetermined relationship may be between the window in which the bodily fluid testing equipment is alignable and the section. Alternatively, or additionally, the predetermined relationship may be between a determined location of a machine readable label, by alignment with the machine readable label window, and the section.

Preferably, the non-transitory computer-readable medium further stores instructions that when executed by the one or more processors cause the electronic device to perform the step of determining the at least one edge comprises determining a discontinuity in brightness between the testing region and a surrounding region indicative of the interface between the testing region and the surrounding region;

Preferably, the determining at least one edge of the first bodily fluid testing region comprises determining two opposite edges of the first bodily fluid testing region, and the non-transitory computer-readable medium further stores instructions that when executed by the one or more processors cause the electronic device to perform the step of determining the location of the first bodily fluid testing region as being confined between the two edges;

Preferably, the non-transitory computer-readable medium further stores instructions that when executed by the one or more processors cause the electronic device to perform the step of presenting the output on a display of the electronic device Preferably, the method is performed at the electronic device.

In a sixth aspect, there is provided an electronic device comprising one or more processors, the one or more processors arranged to cause the electronic device to perform the steps of:

acquiring image data of a bodily fluid testing equipment, the bodily fluid testing equipment comprising one or more bodily fluid testing regions;

determining at least one edge of a first bodily fluid testing region of the one or more bodily fluid testing regions from the image data;

determining a location of the first bodily fluid testing region in the image data based upon a predetermined relationship between the at least one edge and a position of the first bodily fluid testing region;

sampling colour data of a sub-region of the first bodily fluid testing region based upon the determined location;

determining, based upon the sampled colour data, whether an indicator of a bodily condition has interacted with the first bodily testing region of the one or more bodily fluid testing regions; and providing an output, wherein the output is based upon whether the indicator of the bodily condition has interacted with the first bodily fluid testing region of the one or more bodily fluid testing regions.

In this way, all of the processing can be carried out locally at the electronic device. This is particularly beneficial if, for example, a connection to a remote server is not available.

Preferably, acquiring the image data comprises capturing the image data by a camera on the electronic device.

Preferably the one or more processors are further arranged to cause the electronic device to perform the steps of displaying, before the image data is captured, a live image of the bodily fluid testing equipment on a display of the electronic device using the camera of the electronic device; and displaying, before the image data is captured, a window on the display of the electronic device with the live image, wherein the bodily fluid testing equipment is alignable in the window.

Preferably, the window is arranged such that edges of the bodily fluid testing equipment are alignable with edges of the window.

Preferably, a machine readable label window is presented within the window and arranged such that a machine readable label on the bodily fluid testing equipment is alignable with the machine readable label window.

Preferably, the one or more processors are further arranged to cause the electronic device to perform the step of automatically capturing the image data of the bodily fluid testing equipment in response to identifying that the bodily fluid testing equipment is aligned in the window. Preferably, the electronic device automatically captures image data of the bodily fluid testing equipment in response to identifying that both the bodily fluid testing equipment is aligned in the window and the machine readable label is aligned in the machine readable label window.

Preferably the one or more processors are further arranged to cause the electronic device to perform the step of determining a section of the bodily fluid testing equipment that includes the one or more bodily fluid testing regions. Preferably, the determining of the section of the bodily fluid testing equipment that includes the one or more bodily fluid testing regions may be based upon a predetermined relationship. Preferably the predetermined relationship may be between the window in which the bodily fluid testing equipment is alignable and the section. Alternatively, or additionally, the predetermined relationship may be between a determined location of a machine readable label, by alignment with the machine readable label window, and the section.

Preferably, determining the at least one edge comprises determining a discontinuity in brightness between the testing region and a surrounding region indicative of the interface between the testing region and the surrounding region.

Preferably, the determining at least one edge of the first bodily fluid testing region comprises determining two opposite edges of the first bodily fluid testing region, and the one or more processors are further arranged to cause the electronic device to perform the step of determining the location of the first bodily fluid testing region as being confined between the two edges.

Preferably the one or more processors are further arranged to cause the electronic device to perform the step of presenting the output on a display of the electronic device.

Preferably, the method is performed at the electronic device.

In a seventh aspect, there is provided a server arranged to perform a bodily fluid testing region identification, the bodily fluid testing region identification comprising the following steps:

receiving image data, from an electronic device, of a bodily fluid testing equipment, the bodily fluid testing equipment comprising one or more bodily fluid testing regions;

determining at least one edge of a first bodily fluid testing region of the one or more bodily fluid testing regions from the image data;

determining a location of the first bodily fluid testing region in the image data based upon a predetermined relationship between the at least one edge and a position of the first bodily fluid testing region;

sampling colour data of a sub-region of the first bodily fluid testing region based upon the determined location;

determining, based upon the sampled colour data, whether an indicator of a bodily condition has interacted with the first bodily testing region of the one or more bodily fluid testing regions; and providing an output, wherein the output is based upon whether the indicator of the bodily condition has interacted with the first bodily fluid testing region of the one or more bodily fluid testing regions.

In this way, the location of the one or more bodily fluid testing regions can be accurately determined. Additionally, in this way, the processing can be carried out remotely at the server rather than locally at the electronic device. This is particularly advantageous for non-iOS devices which do not necessarily have a consistent colour spectrum between devices. By carrying out the processing at a server, a consistent colour spectrum can be used to ensure that consistent results are achieved. Having determined the location of the first bodily fluid testing region, the determined location information can be used to ensure that the sub-region from the colour data sampled is within the bodily fluid testing region. This improves the accuracy of the determined output.

Preferably the electronic device may be a smartphone. Preferably the image data may be a photograph of the bodily fluid testing equipment. Preferably the bodily fluid testing region(s) may be a colour change pad(s) that changes colour in response to interaction with indicator(s) in bodily fluid. Preferably the server may utilise a Python application programming interface.

Preferably, the server is further arranged to perform the step of determining a section of the bodily fluid testing equipment that includes the one or more bodily fluid testing regions.

In this way, a coarse identification of the approximate location of the one or more bodily fluid testing regions can be determined. Preferably the determining may be based upon a predetermined relationship between an alignment of the bodily fluid testing equipment and a window displayed on the display of an electronic device when the image data is captured using a camera of the electronic device. Alternatively, or additionally, the determining may be based upon a predetermined relationship between a determined location of a machine readable label and the section.

Preferably, determining the at least one edge comprises determining a discontinuity in brightness between the testing region and a surrounding region indicative of the interface between the testing region and the surrounding region.

In this way, the location of the testing regions can be determined by the difference in brightness between the testing regions and the region surrounding the testing regions. Preferably, determining the at least one edge may further comprise scanning the determined section of the bodily fluid testing equipment.

Preferably, the determining at least one edge of the first bodily fluid testing region comprises determining two opposite edges of the first bodily fluid testing region, and the method further comprises determining the location of the first bodily fluid testing region as being confined between the two edges.

In this way, the accuracy of the determined location can be enhanced.

Preferably, the steps further comprise sending the output to the electronic device.

In an eighth aspect, there is provided a system comprising an electronic device arranged to capture and transmit image data of a bodily fluid testing equipment to a server, the bodily fluid testing equipment comprising one or more bodily fluid testing regions, and a server according to the seventh aspect.

In a ninth aspect, there is provided a method for determining an indication of a bodily condition in image data of bodily fluid testing equipment, the image data captured by an electronic device, the method comprising:

determining colour data of a first bodily fluid testing region of one or more bodily fluid testing regions of a bodily fluid testing equipment from image data of the bodily fluid testing equipment by sampling a colour of the first bodily fluid testing region;

determining colour calibration data of at least one background sub-region of a background region of the bodily fluid testing equipment, wherein the background region is adjacent to the one or more bodily fluid testing regions;

calibrating the colour data based upon the determined colour calibration data to determine calibrated colour data;

determining, by comparing the calibrated colour data to reference colour data, whether an indicator of a bodily condition has interacted with the first bodily fluid testing region of the one or more bodily fluid testing regions; and providing an output, wherein the output is based upon whether the indicator of the bodily condition has interacted with the first bodily fluid testing region of the one or more bodily fluid testing regions.

In this way, the colour data can be calibrated, or adjusted, to negate the effects of ambient lighting when calculating a colour change in the bodily fluid testing region following the application of a bodily fluid. The skilled person will readily understand that the terms colour calibration and colour adjustment are interchangeable in the context.

Preferably the bodily fluid may be urine. Preferably, if there is more than one background sub-region, the calibration of the colour data may be based upon the determined colour calibration data of each of the background sub-regions. Preferably, the background region may be a border surrounding the bodily fluid testing region on the bodily fluid testing equipment. Preferably the image data may be captured using the camera of an electronic device. Preferably the electronic device may be a smartphone. Preferably the colour calibration data may be a colour temperature, or light temperature, of the at least one background sub-region of the background region. The terms colour temperature and light temperature are used interchangeably. A colour temperature is a characteristic of a light source illuminating an object and can range from a cool temperature or 'bluish' colour to a warm temperature or 'yellowish' colour; colour temperature relates to the temperature at which a black body would emit radiation of the same colour.

Preferably, the background region is substantially white in colour.

In this way, the colour calibration data, such as a colour temperature, of the white background region can be used to determine the colour calibration data resulting from ambient lighting illuminating the bodily fluid testing equipment. This allows for the colour data to be calibrated thereby removing effects in the colour data resulting from the ambient lighting. Moreover, this removes the need to use separate colour calibration charts either on the bodily fluid testing equipment, or captured with the image data of the bodily fluid testing equipment as the white background can instead be used.

Preferably, the colour data is determined based upon sampling a testing sub-region of the first bodily fluid testing region, the testing sub-region at a location within the bodily fluid testing region.

In this way, the entire bodily fluid testing region need not be sampled. This improves the accuracy of the colour data by decreasing the likelihood of sampling a region that overlaps the bodily fluid testing region and background region if the position of the sampling is not entirely accurate.

Preferably, a location of the at least one background sub-region is determined based upon a predetermined displacement from the location of the testing sub-region.

In this way, it can be ensured that the colour calibration data is determined from the background region rather than the bodily fluid testing region, or a combination of the bodily fluid testing region and the background region.

Preferably, the testing sub-region, and the bodily fluid testing equipment may be of known sizes, for example as determined from a machine readable label presented on the bodily fluid testing equipment. Due to alignment of the bodily fluid testing equipment in a window presented on a display of the electronic device when the image data is captured, and these known sizes, and a determined location of the testing sub-region, this information can be utilised to arrange (each of) the background sub-region(s) such that they are on the background region of the bodily fluid testing equipment in the image data, rather than on the testing sub-region or away from the bodily fluid testing equipment itself.

Preferably, the at least one background sub-region comprises two background sub-regions.

In this way, a more accurate determination of colour calibration data can be achieved.

Preferably, a first background sub-region of the two background sub-regions is displaced away from the bodily fluid testing region on a first side of the bodily fluid testing region, and a second background sub-region of the two background sub-regions is displaced away from a second side of the bodily fluid testing region, wherein the second side of the bodily fluid testing region is an opposing side of the bodily fluid testing region to the first side of the bodily fluid testing region.

In this way, differing ambient lighting illuminating either side of the bodily fluid testing equipment is accounted for in the calibration. As such, the accuracy of the calibrated colour data is improved.

Preferably, each of the testing sub-region, the first background sub-region and the second background sub-region are arranged along a straight line between the first background sub-region and the second background sub-region, and where the method further comprises:
  determining a first colour calibration data of the first background sub-region;
  determining a second colour calibration data of the second background sub-region;
  determining a colour calibration gradient along the line joining testing sub-region, the first background sub-region and the second background sub-region, the colour calibration data gradient based upon the first colour calibration data and the second colour calibration data; and
  calculating a calculated colour calibration data, based upon the colour calibration data gradient, at a point along the line, wherein the point corresponds to the location of the testing sub-region, and wherein calibrating the colour data based upon the determined colour calibration data comprises calibrating the colour data at the testing sub-region based upon the calculated colour calibration data to determine the calibrated colour data.

In this way, if there is a colour calibration data gradient across the equipment, for example caused by different ambient lighting sources either side of the bodily fluid testing equipment when the image data is captured, this is accounted for in the calibration. As such, the accuracy of the calibration is improved.

Preferably, the image data is captured with a camera of an electronic device, using a camera flash associated with the camera.

Preferably calibrating the colour data further comprises using colour calibration data of the flash. Preferably the colour calibration data of the flash may be the colour temperature of the flash. In this way, the accuracy of the calibrated colour data can be further improved, particularly because the colour calibration data of the primary light source illuminating the bodily fluid testing equipment is known. The camera flash of an electronic device such as a smartphone may have a known predetermined colour temperature. Due to the proximity of the camera flash to the bodily fluid testing equipment when the image data is captured, the colour temperature of the camera flash may dominate any ambient lighting effects. As such, colour data of a first bodily fluid testing region can be calibrated using the known colour temperature of the camera flash. Alternatively, the flash can be used to contribute to ambient lighting conditions.

Preferably, the bodily fluid testing region comprises a colour change pad that changes colour in response to interaction with an indicator in the bodily fluid.

In this way, if a bodily fluid contains an indicator of a predetermined condition that the colour change pad is sensitive to, the colour change pad will change colour in response to interacting with the bodily fluid. As such, a change in colour of the testing region can be used to determine if the condition associated with the indicator is present in the bodily system of an individual who has expelled the bodily fluid.

Preferably, the output is presented on a display of an electronic device.

Preferably, the method of the ninth aspect is performed at an electronic device, and the image data is captured with a camera of the electronic device.

In this way, all of the processing can be carried out locally at the electronic device. This is particularly beneficial if, for example, a connection to a remote server is not available.

Preferably, the method further comprises, prior to capturing the image data:
  displaying a live image of the bodily fluid testing equipment on a display of the electronic device using the camera of the electronic device; and
  displaying a window on the display of the electronic device with the live image, wherein the bodily fluid testing equipment is alignable in the window.

In this way, the bodily fluid testing equipment can be accurately aligned in the image to aid the processing of the image. Preferably, a machine readable label window is presented within the window and arranged such that a machine readable label on the bodily fluid testing equipment is alignable with the machine readable label window. Preferably, a section of the bodily fluid testing equipment that includes one or more bodily fluid testing regions may be identified based upon a predetermined relationship. Preferably the predetermined relationship may be between the window in which the bodily fluid testing equipment is alignable and the section. Alternatively, or additionally, the predetermined relationship may be between a determined location of a machine readable label and the section, wherein the location of the machine readable label can be determined based upon the alignment of the machine readable label in the machine readable label window.

Alternatively, the method of the ninth aspect may be performed at a server in response to an electronic device transmitting the image data of the bodily fluid testing equipment to the server.

In this way, the processing can be carried out remotely at the server rather than locally at the electronic device. This is particularly advantageous for non-iOS devices which do not necessarily have a consistent colour spectrum between devices. By carrying out the processing at a server, a consistent colour spectrum can be used to ensure that consistent results are achieved. Preferably, the image data may be captured by a camera at the electronic device. Preferably, prior to capturing the image data, the electronic device may display a live image of the bodily fluid testing equipment on a display of the electronic device using the camera of the electronic device, and display a window on the display of the electronic device with the live image wherein the bodily fluid testing equipment is alignable in the window. Preferably, the server may utilise a Python application programming interface.

Preferably, providing the output comprises the server transmitting the output to the electronic device.

In this way, the advantages of the processing be carried out at the server can be utilised whilst then presenting the output to the user at the electronic device.

In an tenth aspect, there is provided an electronic device comprising one or more processors, wherein the electronic device is arranged to capture the image data, and wherein the one or more processors are arranged to cause the electronic device to perform the steps of:
  determining colour data of a first bodily fluid testing region of one or more bodily fluid testing regions of a bodily fluid testing equipment from image data of the bodily fluid testing equipment by sampling a colour of the first bodily fluid testing region;
  determining colour calibration data of at least one background sub-region of a background region of the bodily fluid testing equipment, wherein the background region is adjacent to the one or more bodily fluid testing regions;
  calibrating the colour data based upon the determined colour calibration data to determine calibrated colour data;
  determining, by comparing the calibrated colour data to reference colour data, whether an indicator of a bodily condition has interacted with the first bodily fluid testing region of the one or more bodily fluid testing regions; and
  providing an output, wherein the output is based upon whether the indicator of the bodily condition has interacted with the first bodily fluid testing region of the one or more bodily fluid testing regions.

In this way, all of the processing can be carried out locally at the electronic device. This is particularly beneficial if, for example, a connection to a remote server is not available.

Preferably, the background region is substantially white in colour;

Preferably, the colour data is determined based upon sampling a testing sub-region of the first bodily fluid testing region, the testing sub-region at a location within the bodily fluid testing region;

Preferably, a location of the at least one background sub-region is determined based upon a predetermined displacement from the location of the testing sub-region;

Preferably, the at least one background sub-region comprises two background sub-regions;

Preferably, a first background sub-region of the two background sub-regions is displaced away from the bodily fluid testing region on a first side of the bodily fluid testing region, and a second background sub-region of the two background sub-regions is displaced away from a second side of the bodily fluid testing region, wherein the second side of the bodily fluid testing region is an opposing side of the bodily fluid testing region to the first side of the bodily fluid testing region;

Preferably, each of the testing sub-region, the first background sub-region and the second background sub-region are arranged along a straight line between the first background sub-region and the second background sub-region, and wherein the one or more processors are further arranged to cause the electronic device to perform the steps of:
  determining a first colour calibration data of the first background sub-region;
  determining a second colour calibration data of the second background sub-region;
  determining a colour calibration gradient along the line joining testing sub-region, the first background sub-region and the second background sub-region, the colour calibration data gradient based upon the first colour calibration data and the second colour calibration data; and
  calculating a calculated colour calibration data, based upon the colour calibration data gradient, at a point along the line, wherein the point corresponds to the location of the testing sub-region, and wherein calibrating the colour data based upon the determined colour calibration data comprises calibrating the colour data at the testing sub-region based upon the calculated colour calibration data to determine the calibrated colour data Preferably, the image data is captured with a camera of an electronic device, using a camera flash associated with the camera.

Preferably, the bodily fluid testing region comprises a colour change pad that changes colour in response to interaction with an indicator in the bodily fluid.

Preferably, the output is presented on a display of an electronic device.

Preferably, the method is performed at an electronic device, and the image data is captured with a camera of the electronic device.

Preferably, the one or more processors are further arranged to cause the electronic device to, prior to capturing the image data, perform the steps of:
  displaying a live image of the bodily fluid testing equipment on a display of the electronic device using the camera of the electronic device; and
  displaying a window on the display of the electronic device with the live image, wherein the bodily fluid testing equipment is alignable in the window.

In a eleventh aspect, there is provided a server arranged to receive the image data from an electronic device, and further arranged to perform the method of:
  determining colour data of a first bodily fluid testing region of one or more bodily fluid testing regions of a bodily fluid testing equipment from image data of the bodily fluid testing equipment by sampling a colour of the first bodily fluid testing region;
  determining colour calibration data of at least one background sub-region of a background region of the bodily fluid testing equipment, wherein the background region is adjacent to the one or more bodily fluid testing regions;
  calibrating the colour data based upon the determined colour calibration data to determine calibrated colour data;
  determining, by comparing the calibrated colour data to reference colour data, whether an indicator of a bodily condition has interacted with the first bodily fluid testing region of the one or more bodily fluid testing regions; and
  providing an output, wherein the output is based upon whether the indicator of the bodily condition has interacted with the first bodily fluid testing region of the one or more bodily fluid testing regions.

In this way, the processing can be carried out remotely at the server rather than locally at the electronic device. This is particularly advantageous for non-iOS devices which do not necessarily have a consistent colour spectrum between devices. By carrying out the processing at a server, a consistent colour spectrum can be used to ensure that consistent results are achieved. Preferably, the image data may be captured by a camera at the electronic device. Preferably, prior to capturing the image data, the electronic device may display a live image of the bodily fluid testing equipment on a display of the electronic device using the camera of the electronic device, and display a window on the display of the electronic device with the live image wherein the bodily fluid testing equipment is alignable in the window. Preferably, the server may utilise a Python application programming interface.

Preferably, the background region is substantially white in colour;

Preferably, the colour data is determined based upon sampling a testing sub-region of the first bodily fluid testing region, the testing sub-region at a location within the bodily fluid testing region;

Preferably, a location of the at least one background sub-region is determined based upon a predetermined displacement from the location of the testing sub-region;

Preferably, the at least one background sub-region comprises two background sub-regions;

Preferably, a first background sub-region of the two background sub-regions is displaced away from the bodily fluid testing region on a first side of the bodily fluid testing region, and a second background sub-region of the two background sub-regions is displaced away from a second side of the bodily fluid testing region, wherein the second side of the bodily fluid testing region is an opposing side of the bodily fluid testing region to the first side of the bodily fluid testing region;

Preferably, each of the testing sub-region, the first background sub-region and the second background sub-region are arranged along a straight line between the first background sub-region and the second background sub-region, and wherein the server is further arranged to perform the method of:

determining a first colour calibration data of the first background sub-region;

determining a second colour calibration data of the second background sub-region;

determining a colour calibration gradient along the line joining testing sub-region, the first background sub-region and the second background sub-region, the colour calibration data gradient based upon the first colour calibration data and the second colour calibration data; and calculating a calculated colour calibration data, based upon the colour calibration data gradient, at a point along the line, wherein the point corresponds to the location of the testing sub-region, and wherein calibrating the colour data based upon the determined colour calibration data comprises calibrating the colour data at the testing sub-region based upon the calculated colour calibration data to determine the calibrated colour data Preferably, the image data is captured with a camera of an electronic device, using a camera flash associated with the camera.

Preferably, the bodily fluid testing region comprises a colour change pad that changes colour in response to interaction with an indicator in the bodily fluid.

Preferably, providing the output comprises the server transmitting the output to the electronic device.

In this way, the advantages of the processing be carried out at the server can be utilised whilst then presenting the output to the user at the electronic device.

In a twelfth aspect, there is provided a system comprising, an electronic device arranged to capture and transmit image data of a bodily fluid testing equipment to a server, the bodily fluid testing equipment comprising one or more bodily fluid testing regions, and a server according to the eleventh aspect.

In a thirteenth aspect, there is provided a non-transitory computer-readable medium storing instructions thereon that when executed by a processor of an electronic device cause the electronic device to perform the method steps of: determining colour data of a first bodily fluid testing region of one or more bodily fluid testing regions of a bodily fluid testing equipment from image data of the bodily fluid testing equipment by sampling a colour of the first bodily fluid testing region;

determining colour calibration data of at least one background sub-region of a background region of the bodily fluid testing equipment, wherein the background region is adjacent to the one or more bodily fluid testing regions;

calibrating the colour data based upon the determined colour calibration data to determine calibrated colour data;

determining, by comparing the calibrated colour data to reference colour data, whether an indicator of a bodily condition has interacted with the first bodily fluid testing region of the one or more bodily fluid testing regions; and providing an output, wherein the output is based upon whether the indicator of the bodily condition has interacted with the first bodily fluid testing region of the one or more bodily fluid testing regions.

In this way, all of the processing can be carried out locally at the electronic device. This is particularly beneficial if, for example, a connection to a remote server is not available.

Preferably, the background region is substantially white in colour;

Preferably, the colour data is determined based upon sampling a testing sub-region of the first bodily fluid testing region, the testing sub-region at a location within the bodily fluid testing region;

Preferably, a location of the at least one background sub-region is determined based upon a predetermined displacement from the location of the testing sub-region;

Preferably, the at least one background sub-region comprises two background sub-regions;

Preferably, a first background sub-region of the two background sub-regions is displaced away from the bodily fluid testing region on a first side of the bodily fluid testing region, and a second background sub-region of the two background sub-regions is displaced away from a second side of the bodily fluid testing region, wherein the second side of the bodily fluid testing region is an opposing side of the bodily fluid testing region to the first side of the bodily fluid testing region;

Preferably, each of the testing sub-region, the first background sub-region and the second background sub-region are arranged along a straight line between the first background sub-region and the second background sub-region, and wherein the non-transitory computer-readable medium further stores instructions that when executed by a processor of an electronic device cause the electronic device to perform the method steps of:

determining a first colour calibration data of the first background sub-region;
determining a second colour calibration data of the second background sub-region;
determining a colour calibration gradient along the line joining testing sub-region, the first background sub-region and the second background sub-region, the colour calibration data gradient based upon the first colour calibration data and the second colour calibration data; and
calculating a calculated colour calibration data, based upon the colour calibration data gradient, at a point along the line, wherein the point corresponds to the location of the testing sub-region, and wherein calibrating the colour data based upon the determined colour calibration data comprises calibrating the colour data at the testing sub-region based upon the calculated colour calibration data to determine the calibrated colour data Preferably, the image data is captured with a camera of an electronic device, using a camera flash associated with the camera.

Preferably, the bodily fluid testing region comprises a colour change pad that changes colour in response to interaction with an indicator in the bodily fluid.

Preferably, the output is presented on a display of an electronic device.

Preferably, the method of the ninth aspect is performed at an electronic device, and the image data is captured with a camera of the electronic device.

Preferably, the non-transitory computer-readable medium further stores instructions that when executed by a processor of an electronic device cause the electronic device to perform the method steps of, prior to capturing the image data:
displaying a live image of the bodily fluid testing equipment on a display of the electronic device using the camera of the electronic device; and
displaying a window on the display of the electronic device with the live image, wherein the bodily fluid testing equipment is alignable in the window.

In a fourteenth aspect, there is provided a lateral flow bodily fluid testing system, the system comprising:
an application-analysable bodily fluid testing equipment having a body portion and one or more lateral flow testing strips combined with a first surface of the body portion, the one or more lateral flow strips being sensitive to indicators of bodily conditions in bodily fluid, and wherein the one or more lateral flow strips each comprise a fluid uptake region connected to an analysis region; and
an electronic device comprising a camera and one or more processors, wherein the one or more processors are configured to:
acquire image data of the application-analysable bodily fluid testing equipment with the camera of the electronic device;
perform testing of bodily fluid applied to the application-analysable bodily fluid testing equipment using the image data to determine whether indicators of one or more bodily conditions are present in the applied bodily fluid; and
output a result indicating whether the indicators of one or more bodily conditions are present in the applied bodily fluid.

In this way, lateral flow testing can be achieved in an efficient manner without the reliance on specialist lateral flow testing devices. Lateral flow testing provides for testing for indicators of bodily conditions in the bodily fluid of a person. The testing can be performed on a single device, thereby improving the usability. Preferably, the one or more lateral flow testing strips are arranged to test for to pregnancy, drug misuse, and testing for hormones or antibodies in conditions where these provide diagnostic support such as ovulation health, prostate specific antigen levels, malaria, infertility, sexually transmitted infections, and diabetes HbA1c, amongst others. In an example, a lateral flow strip is sensitive to analytes respectively associated with the aforementioned conditions. In an example of drug misuse, the lateral flow strip is sensitive to a drug metabolite associated with the drug being tested for.

Preferably the one or more lateral flow strips may each be arranged to draw bodily fluid along their length by capillary action. Preferably the one or more lateral flow strips may have a region along their length that is sensitive to indicators of bodily conditions in the bodily fluid, wherein a line appears within the region in response to the indicator of the bodily condition being present in the bodily fluid. Preferably the one or more lateral flow strips may be attached to the first surface of the body portion. Preferably the electronic device may be a smartphone.

Preferably, the body portion further comprises machine readable information arranged on the body portion.

In this way, a single application executable on the electronic device can be arranged to carry out analysis for multiple tests relating to different conditions, and the application can determine the type of test that is being carried out from image data of the machine readable label captured by a camera of the device. Determining the type of test, before carrying out the analysis process, can expedite the analysis process as the application can more quickly identify what is to be analysed.

Preferably, the machine readable information may be usable by the associated application to access, from storage accessible by the application, equipment information corresponding to the machine readable information. The machine readable information may also be used as an anchor point to aid the locating of the testing regions or sensitive regions, to provide LOT information including batch number and expiry date, for use in lighting conditions testing, to identify the date of manufacture and for a unique ID string.

Preferably, the equipment information may include any of a size or aspect ratio of the card, the type of indicators the lateral flow strips are sensitive to, the number and size of lateral flow strips, and the position of the lateral flow strips in relation to (or displacement from) the machine readable label, the one or more anchor points and/or the anchor bar.

Preferably the machine readable label and the testing region(s) may be arranged on the same surface, i.e. the first surface, of the body portion.

Preferably the machine readable label may be a QR code.

Preferably, the body portion comprises a holding area, the holding area holdable by a user both when applying bodily fluid to the one or more lateral flow strips and capturing image data of the equipment.

In this way, a user of the equipment does not need to put the equipment down between the steps of applying the bodily fluid and capturing the image data; the entire process of applying the bodily fluid, capturing the image, and analysis with the application can be performed whilst maintaining the equipment in the user's hand. This is beneficial as it obviates any contamination to the equipment by placing the equipment on a surface when capturing the image, and also inhibits any contamination to a surface from the applied bodily fluid. This also improves hygiene.

Preferably, the holding area comprises indicia indicating to a user of the equipment to hold the equipment by the holding area.

In this way, it is clear to the user as to where to hold the equipment for optimised use, thereby improving the usability.

Preferably, the body portion is substantially planar.

In this way, the equipment can be efficiently packaged. More so, this allows for the equipment to be delivered to a user by conventional postal services.

Preferably, at least a portion of the liquid uptake region of each of the one or more lateral flow testing strips extends over an edge of the first surface of the body portion.

In this way, the equipment the one or more lateral flow strips can be dipped into bodily fluid without the bodily fluid contacting the body portion of the equipment. This improves hygiene. Additionally, due to this arrangement, the body portion is maintained in a clean and dry state which may be beneficial during analysis by the associated application.

Preferably, the one or more lateral flow testing strips comprises a plurality of lateral flow testing strips separate from one another and combined with a common holding region.

In this way, the accuracy can be improved by performing multiple tests from a single application of bodily fluid.

Preferably, the lateral flow strips may be attached to the common holding region.

Preferably, the plurality of lateral flow testing strips are arranged to test for indicators of different conditions in bodily fluid.

In this way, indicators of multiple conditions can be tested for from a single application of bodily fluid.

Preferably, each lateral flow strip may be arranged to test for an indicator of a different condition.

Preferably, the one or more lateral flow strips is arranged to detect the presence of indicators of one or more drugs in bodily fluid applied the one or more lateral flow strips.

In this way, the equipment can be used to identify whether the person who has expelled the bodily fluid has taken part in drug abuse/drug misuse.

Preferably, the one or more lateral flow strips may be arranged to detect the presence of indicators of one or more of cannabis or marijuana (THC), amphetamine, cocaine, ecstasy, methamphetamine, morphine, heroin, fentanyl, synthetic cannabinoids, methcathinone, ketamine LSD and acids and/or their metabolites, amongst others, in applied bodily fluid.

Preferably, the one or more lateral flow strips may comprise a plurality of lateral flow strips arranged to detect indicators of the presence of a plurality of drugs in the bodily fluid applied to the plurality of lateral flow strips. In this way, a single application of bodily fluid can be used to test for the presence of indicators of multiple drugs.

Preferably, each lateral flow strip of the plurality of lateral flow strips may be arranged to detect indicators of a different drug in bodily fluid applied to the lateral flow strips.

Preferably, the bodily fluid is urine.

In this way, the equipment can be used to identify indicators of conditions present in a urine sample.

Preferably, the one or more processors are further configured to determine whether one or more lines are present in the analysis regions of the one or more lateral flow strips when performing the testing of the bodily fluid.

Preferably, the one or more processors are further configured to:

output a positive result that indicators are present in the bodily fluid for each lateral flow strip for which a predetermined test line appears in the respective analysis region; and output a negative result that indicators are not present in the bodily fluid for each lateral flow strip for which a predetermined test line does not appear in the respective analysis region.

Preferably, the one or more processors are further configured to determine the intensity of the one or more lines in response to determining that a predetermined test line is present.

Preferably, before acquiring image data, the one or more processors are further configured to:

display a live image of the bodily fluid testing equipment on a display of the electronic device using the camera of the electronic device; and display a window on the display of the electronic device with the live image, wherein the bodily fluid testing equipment is alignable in the window.

In this way the bodily fluid testing equipment can be easily aligned before the image data is acquired. Preferably, a machine readable label window is presented within the window and arranged such that a machine readable label on the bodily fluid testing equipment is alignable with the machine readable label window. Preferably, a section of the bodily fluid testing equipment that includes the analysis regions may be identified based upon a predetermined relationship. Preferably the predetermined relationship may be between the window in which the bodily fluid testing equipment is alignable and the section. Alternatively, or additionally, the predetermined relationship may be between a determined location of a machine readable label and the section, wherein the location of the machine readable label can be determined based upon the alignment of the machine readable label in the machine readable label window.

Preferably, the one or more processors are further configured to automatically capture the image data of the bodily fluid testing equipment in response to identifying that the bodily fluid testing equipment is aligned in the window.

In this way, the need for user input is minimised and the usability of the application is improved by reducing the risk of user error.

Preferably, the one or more processors are further configured to determine positions of the analysis regions of the one or more lateral flow strips based upon determined positions of at least one of a machine readable label, one or more anchor points and/or an anchor bar arranged on the bodily fluid testing equipment.

In this way, the associated application can determine the position of the analysis region of the one or more lateral flow strips during analysis of the equipment. This expedites the processing and improves the accuracy of results of the analysis.

Preferably, the application may be configured to determine the position of the analysis regions of the one or more lateral flow strips using predetermined displacements from one or more lateral flow strips based upon determined positions of at least one of a machine readable label, one or more anchor points and/or an anchor bar. Preferably, the predetermined displacements may be included in equipment information associated with machine readable information presented on the application-analysable bodily fluid testing equipment.

Preferably the application may scan machine readable information usable by the application to access, from storage accessible by the application, equipment information corresponding to the machine readable information. Preferably, the equipment information may include the type of indicators the lateral flow strips are sensitive to, the number and size of lateral flow strips, and the position of the lateral flow strips in relation to (or displacement from) the machine readable label, the one or more anchor points and/or the anchor bar. Preferably the application may display a window on the display of the electronic device with the live image, wherein the bodily fluid testing equipment is alignable in the window.

Preferably, the body portion further comprises a machine readable label arranged on the first surface of the body portion, and wherein the one or more processors are further configured to determine a position of the machine readable label in the image data.

Preferably, the body portion further comprises one or more application-detectable anchor points arranged on the first surface of the body portion, and wherein the one or more processors are further configured to determine positions of the one or more anchor points in the image data.

Preferably the equipment may comprise a plurality of anchor points.

Preferably, the one or more anchor points comprise a plurality of anchor points positioned proximal to the analysis region, and wherein one of the anchor points is distinct from the other anchor points.

In this way, the application may use the distinct anchor point to identify the orientation of the application-analysable bodily fluid testing equipment in the image data.

Preferably, the one or more anchor points comprise indicia presented on the first surface of the body portion.

In this way, the anchor points may be efficiently identified in the image data.

Preferably, the body portion further comprises an anchor bar arranged on the first surface of the body portion at a substantially central position, and wherein the one or more processors are further configured to determine a position of the anchor bar in the image data.

Preferably, the body portion of the equipment further comprises a machine readable label arranged on the body portion, and wherein the one or more processors are further configured to:
  scan the machine readable label; and
  determine, from the machine readable label, equipment information relating to the type of test for which the equipment is arranged.

In this way, a single application executable on the electronic device can be arranged to carry out analysis for multiple tests relating to different conditions, and the application can determine the type of test that is being carried out from image data of the machine readable label captured by a camera of the device. Determining the type of test, before carrying out the analysis process, can expedite the analysis process as the application can more quickly identify what is to be analysed. Preferably, the application may scan the machine readable information and determine the equipment information prior to acquiring the image data.

Preferably, the application may use the machine readable information to access, from storage accessible by the application, equipment information corresponding to the machine readable information. Preferably the storage may be local to the electronic device. Alternatively the storage may be at a server accessible by the electronic device using a network connection.

Preferably, the equipment information may include any of a size or aspect ratio of the card, the type of indicators the lateral flow strips are sensitive to, the number and size of lateral flow strips, and the position of the lateral flow strips in relation to (or displacement from) machine readable information, the one or more anchor points and/or the anchor bar.

Preferably the machine readable label and the testing region(s) may be arranged on the same surface, i.e. the first surface, of the body portion.

Preferably the machine readable information may be a QR code.

In a fifteenth aspect, there is provided a method of testing bodily fluid in a lateral flow bodily fluid testing system, the method comprising:
  acquiring, by a camera of an electronic device, image data of an application-analysable bodily fluid testing equipment comprising one or more lateral flow strips;
  performing, by the electronic device, testing of bodily fluid applied to the application-analysable bodily fluid testing equipment using the image data to determine whether indicators of one or more bodily conditions are present in the applied bodily fluid; and
  outputting, by the electronic device, a result indicating whether the indicators of one or more bodily conditions are present in the applied bodily fluid.

In this way, lateral flow testing can be achieved in an efficient manner without the reliance on specialist lateral flow testing devices. Lateral flow testing provides for testing for indicators of bodily conditions in the bodily fluid of a person. The testing can be performed on a single device, thereby improving the usability.

Preferably the one or more lateral flow strips may each be arranged to draw bodily fluid along their length by capillary action. Preferably the one or more lateral flow strips may have a region along their length that is sensitive to indicators of bodily conditions in the bodily fluid, wherein a line appears within the region in response to the indicator of the bodily condition being present in the bodily fluid.

Preferably the one or more lateral flow strips may be attached to the first surface of the body portion.

Preferably the electronic device may be a smartphone.

Preferably, performing testing of the bodily fluid comprises determining, by the electronic device, whether one or more lines are present in the analysis regions of the one or more lateral flow strips.

Preferably, the outputting the result comprises:
  outputting a positive result that indicators are present in the bodily fluid for each lateral flow strip for which a predetermined test line appears in the respective analysis region; and
  outputting a negative result that indicators are not present in the bodily fluid for each lateral flow strip for which a predetermined test line does not appear in the respective analysis region.

Preferably, the method further comprises in response to determining that a predetermined test line is present determining, by the application, the intensity of the one or more lines.

Preferably, before acquiring the image data, the method further comprises:
  displaying, by a display of the electronic device, a live image of the bodily fluid testing equipment using the camera of the electronic device; and
  displaying, by the display of the electronic device, a window with the live image, wherein the bodily fluid testing equipment is alignable in the window.

In this way the bodily fluid testing equipment can be easily aligned before the image data is acquired. Preferably, a machine readable label window is presented within the window and arranged such that a machine readable label on the bodily fluid testing equipment is alignable with the machine readable label window. Preferably, a section of the bodily fluid testing equipment that includes the analysis regions may be identified based upon a predetermined relationship. Preferably the predetermined relationship may be between the window in which the bodily fluid testing equipment is alignable and the section. Alternatively, or additionally, the predetermined relationship may be between a determined location of a machine readable label and the section, wherein the location of the machine readable label can be determined based upon the alignment of the machine readable label in the machine readable label window.

Preferably, the method further comprises automatically capturing the image data of the bodily fluid testing equipment in response to identifying that the bodily fluid testing equipment is aligned in the window.

In this way, the need for user input is minimised and the usability of the application is improved by reducing the risk of user error.

Preferably, the method further comprises determining positions of analysis regions of the one or more lateral flow strips based upon determined positions of at least one of a machine readable label, one or more anchor points and/or an anchor bar on the bodily fluid testing equipment.

In this way, the associated application can determine the position of the analysis region of the one or more lateral flow strips during analysis of the equipment. This expedites the processing and improves the accuracy of results of the analysis.

Preferably, the application may be configured to determine the position of the analysis regions of the one or more lateral flow strips using predetermined displacements from one or more lateral flow strips based upon determined positions of at least one of a machine readable label, one or more anchor points and/or an anchor bar. Preferably, the predetermined displacements may be included in equipment information associated with machine readable information presented on the application-analysable bodily fluid testing equipment.

Preferably the application may scan machine readable information usable by the application to access, from storage accessible by the application, equipment information corresponding to the machine readable information. Preferably, the equipment information may include the type of indicators the lateral flow strips are sensitive to, the number and size of lateral flow strips, and the position of the lateral flow strips in relation to (or displacement from) the machine readable label, the one or more anchor points and/or the anchor bar. Preferably the application may display a window on the display of the electronic device with the live image, wherein the bodily fluid testing equipment is alignable in the window.

Preferably, the method further comprises determining a position of the machine readable label in the image data.

Preferably, the method further comprises determining positions of the one or more anchor points in the image data.

Preferably the equipment may comprise a plurality of anchor points.

Preferably, the method further comprises determining a position of the anchor bar in the image data.

Preferably, the method further comprises:
scanning, by the application, a machine readable label on the bodily fluid testing equipment; and
determining, by the application, from the machine readable label, equipment information relating to the type of test for which the equipment is arranged.

In this way, a single application executable on the electronic device can be arranged to carry out analysis for multiple tests relating to different conditions, and the application can determine the type of test that is being carried out from image data of the machine readable label captured by a camera of the device. Determining the type of test, before carrying out the analysis process, can expedite the analysis process as the application can more quickly identify what is to be analysed. Preferably, the application may scan the machine readable information and determine the equipment information prior to acquiring the image data.

Preferably, the application may use the machine readable information to access, from storage accessible by the application, equipment information corresponding to the machine readable information. Preferably the storage may be local to the electronic device. Alternatively the storage may be at a server accessible by the electronic device using a network connection.

Preferably, the equipment information may include any of a size or aspect ratio of the card, the type of indicators the lateral flow strips are sensitive to, the number and size of lateral flow strips, and the position of the lateral flow strips in relation to (or displacement from) the machine readable label, the one or more anchor points and/or the anchor bar.

Preferably the machine readable label and the testing region(s) may be arranged on the same surface, i.e. the first surface, of the body portion.

Preferably the machine readable information may be a QR code.

In a sixteenth aspect, there is provided a non-transitory computer-readable medium with instructions stored thereon that when executed by a processor cause the processor to perform the method steps of the fifteenth aspect.

BRIEF DESCRIPTION OF DRAWINGS

Embodiments of the invention are now described, by way of example, with reference to the drawings, in which.

DETAILED DESCRIPTION

Figure 1A:
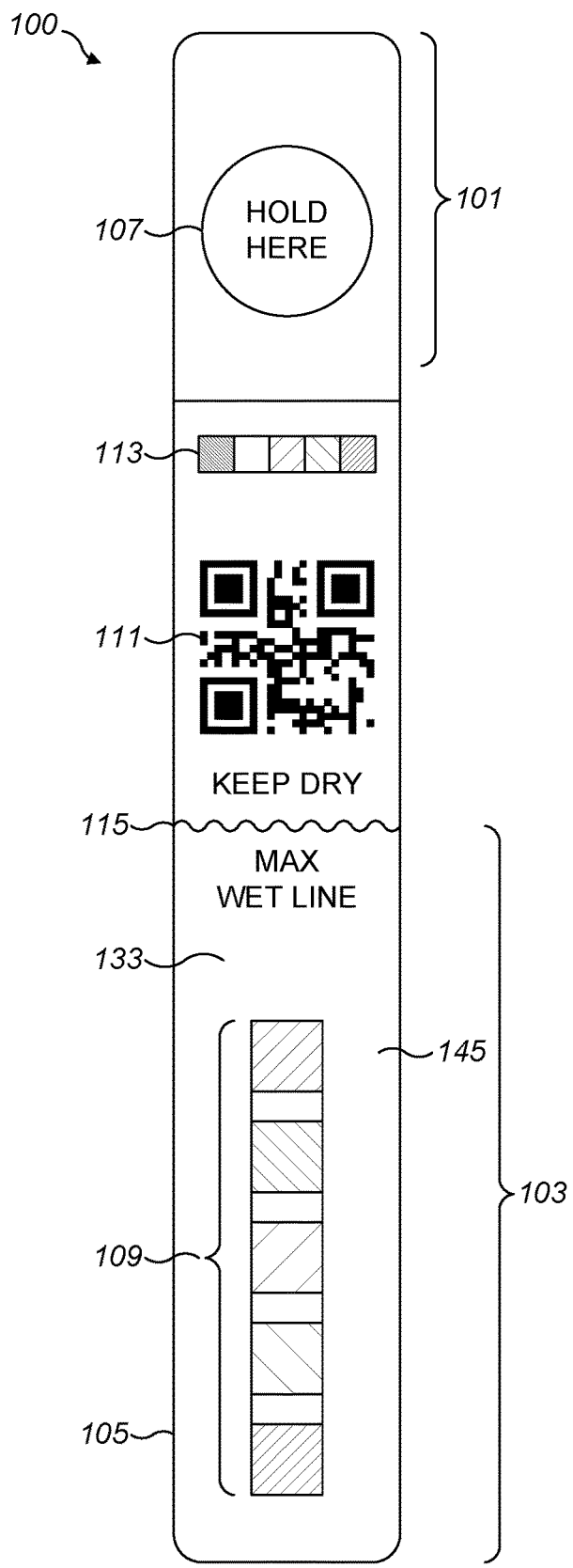
FIG. 1a shows a plan view of the front side of an application-analysable bodily fluid testing equipment according to a first embodiment.

FIGS. 1, 2 and 3 show a bodily fluid testing equipment 100, 200, 300 according to embodiments of the present disclosure. In the present description, the equipment is referred to as a card 100, 200, 300. It will be readily understood, however, that the equipment can be any other shape, size or material suitable to carry out its purpose.

The bodily fluid testing card 100, 200, 300 is arranged such that a user can hold a holding area 101, 201, 301 of the card 100, 200, 300 whilst applying a bodily fluid, such as urine, to a testing area 103, 203, 303 of the card 100, 200, 300. In the present description, the bodily fluid is described as urine. However, the skilled person will readily understand that the embodiments described can also be used with other bodily fluids, such as blood or saliva, or any other suitable bodily fluid. The testing area 103, 203, 303 has one or more colour change pads 109, 209 or lateral flow strips 309, defining one or more testing regions, which interact with identifiers of conditions in the urine. Image data of the card 100, 200, 300, is captured whilst the user is still holding the holding area 101, 201, 301, using a camera of an electronic device such as a smartphone. An application executable on the smartphone implements one or more algorithms to analyse the captured image data and output a result. The result indicates whether or not a condition is present in the user's bodily system based upon indicators of the condition in the user's urine which have interacted with the pads 109, 209 or strips 309 in the testing area 103, 203, 303. As an example, conditions that can be identified include urinary tract infections, diabetes, or glucose levels for diabetic screening or monitoring, and metabolic disorders, kidney disease, liver disease, dietary disorders, pregnancy term complications, pregnancy testing, drug misuse, and testing for hormones or antibodies in conditions where these provide diagnostic support such as ovulation health, prostate specific antigen levels, malaria, infertility, sexually transmitted infections, and diabetes HbA1c, amongst others.

The bodily fluid testing card 100, 200, 300 has a body 105, 205, 305 with an elongate shape which acts as a support structure for the testing pad(s) 109, 209 or strip(s) 309. The body 105, 205, 305 is planar in shape, in that the length and width of the card 100, 200, 300 is considerably greater than the thickness. This is advantageous as the equipment can be efficiently packaged and occupy minimal space. The body 105, 205, 305 can be made from any suitable material for the application of fluid; examples of which can include paper, card, plasticised card, polymer(s) or composites/combinations thereof. The body 105, 205, 305 can be formed of a single layer of the aforementioned materials, alternatively the body 105, 205, 305 can be made of two or more layers of the aforementioned materials adhered together to form a multi-layer structure.

A first end portion of the card 100, 200, 300 is defined as a holding area 101, 201, 301. A second end portion, opposite the first end portion, is defined as a testing area 103, 203, 303.

Figure 1B:
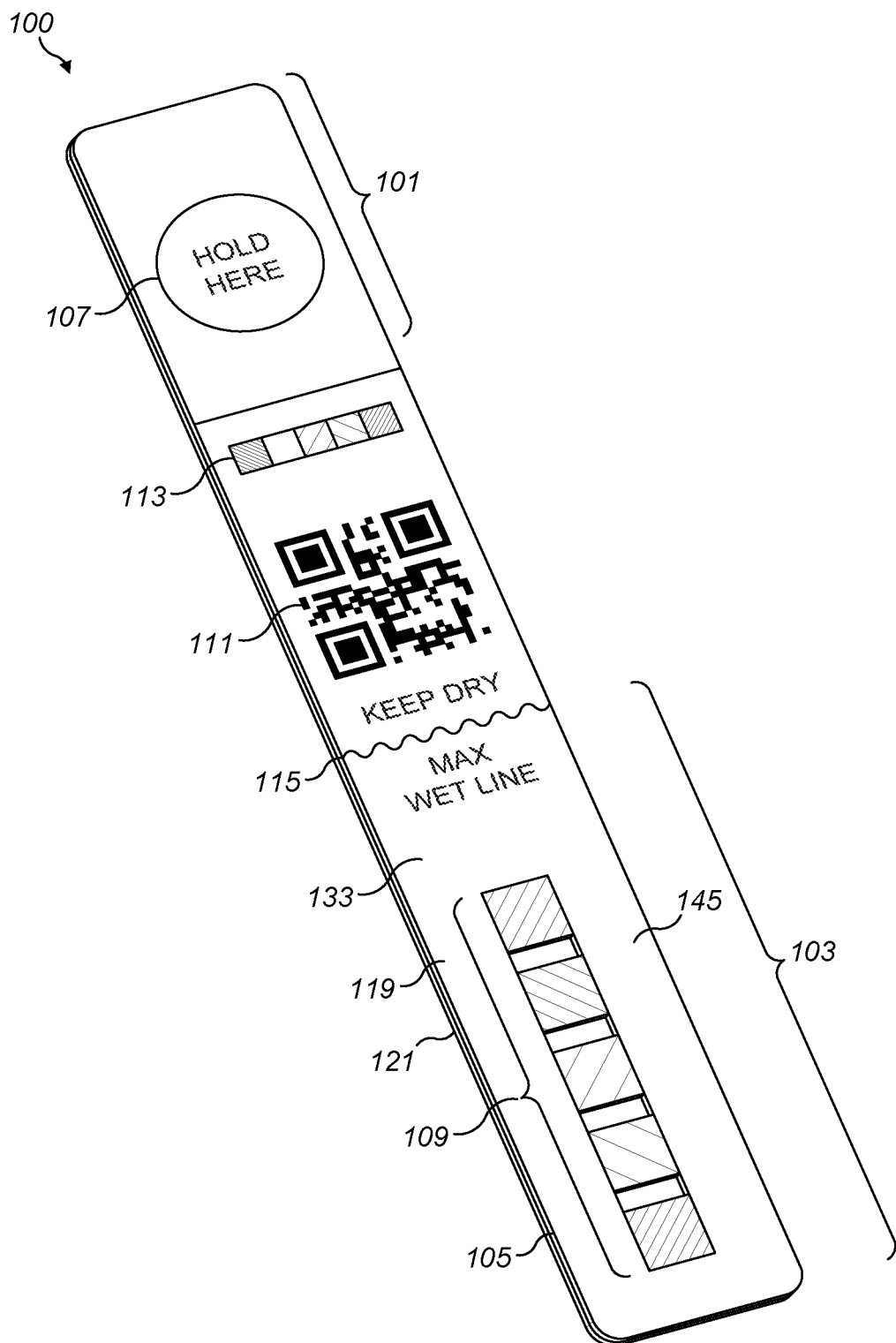
FIG. 1b shows a perspective view of the front side of an application-analysable bodily fluid testing equipment according to the first embodiment.
Figure 1C:
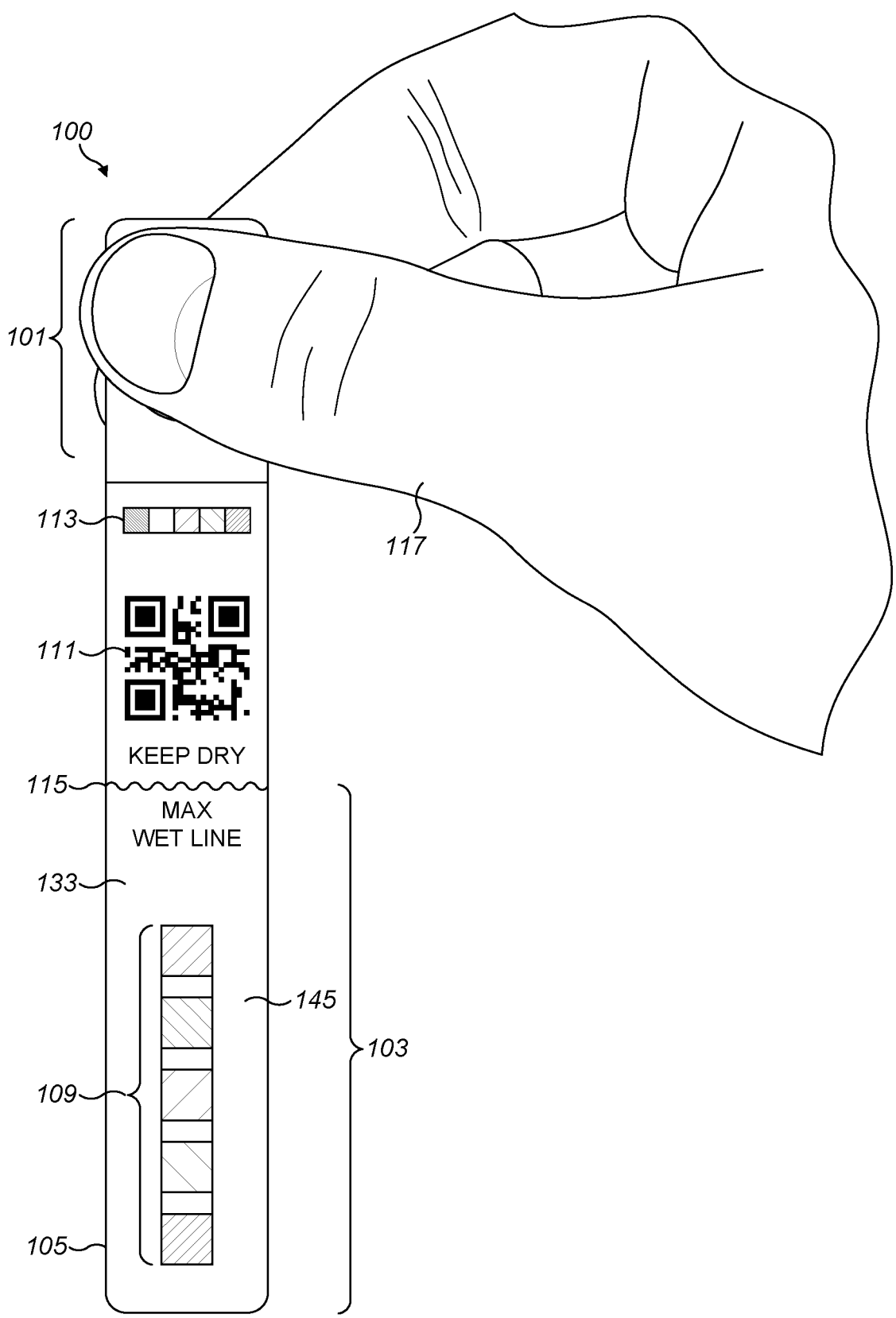
FIG. 1c shows a diagram of a hand holding an application-analysable bodily fluid testing equipment according to the first embodiment.

The holding area 101, 201, 301 includes a handling indicator 107, 207, 307 defining a sub-region of the holding area 101, 201, 301 at which a user of the card 100, 200, 300 should apply a finger/thumb 117, 217, 317 when using the card 100, 200, 300. FIGS. 1c, 2c and 3c show cards 100, 200, 300 according various embodiments being held by the handling indicator 107, 207, 307. The handling indicator 107, 207, 307 comprises indicia such as textual information indicating to the user to hold the card 100, 200, 300 at the handling indicator 107, 207, 307 when in use. The textual information can be surrounded by an enclosed shape, such as a circle, to clearly convey the specific area the user should apply their thumb 117, 217, 317. The handling indicator 107, 207, 307 is printed on a surface 133, 233, 333 of the body 105, 205, 305. Alternatively, the handling indicator 107, 207, 307 can be embossed, debossed, or presented in any other suitable manner on the surface 133, 233, 333. Advantageously, the indicia guide the user as to where the equipment should be held for optimal use.

The surface 133, 233, 333 includes machine readable information 111, 211, 311, such as a QR code. The application scans the QR code 111, 211, 311 to determine the specific test to be performed, as well as reagent lot characteristics and expiry information, and as such which analysis is to be carried out, and to determine specific parameters for scanning or analysing the testing equipment 100, 200, 300. Such parameters can include, but are not limited to, the size and/or aspect ratio of the card, the layout of colour change pads 109, 209 or lateral flow strips 309, sizes of the colour change pads 109, 209 or lateral flow strips 309, distances between the colour change pads 109, 209 or lateral flow strips 309, distances between the colour change pads 109, 209 or lateral flow strips 309 and other features on the card such as the QR code 111, 211, 311, the type or types of colour change pad 109, 209 or lateral flow strip 309, reference colours for the colour change pads 109, 209 and others. The application uses information from the QR code 111, 211, 311 to access equipment information associated with the QR code 111, 211, 311 from storage that is associated with and accessible by the application. The equipment information can include specific parameters relating to the card 100, 200, 300. The location of the QR code 111, 211, 311 can be used by the application in determining the location of the pads 109, 209, 309.

The surface 133, 233, 333 can also include a colour reference chart 113, 213. The colour reference chart 113, 213 is a series of cells printed on in the holding area 101, 201, 301 in colours which can act as colour reference colours for quality control of picture and/or camera performance. In the example of FIG. 1, the colour reference chart 113 comprises a single strip of cells arranged in a line above the QR code 111; the cells colours may include (but not limited to) primary colours and/or key colours to support colour transition points on the dipstick pads. In the example of FIG. 2, the colour reference chart 213 comprises strips of cells substantially surrounding the QR code 211. The skilled person will readily understand that either colour reference chart is compatible with either embodiment.

The testing area 103, 203, 303 includes testing pads 109, 209 or strips 309 that are sensitive to analytes measurable in urine. The testing area 103, 203, 303 is arranged on the same surface 133, 233, 333 of the body 105, 205, 305 as the handling indicator 107, 207, 307. The testing area 103, 203, 303 is described in more detail subsequently.

A maximum depth line 115, 215, 315 is presented on the same surface 133, 233, 333 of the body 105, 205, 305 as the handling indicator 107, 207, 307. The maximum depth line 115, 215, 315 indicates the maximum depth to which the card 100, 200, 300 should be dipped in a urine sample or below which the strip can be exposed for direct application of urine.

The testing area 103, 203, 303 optionally can further include a test pad which has a low tolerance for exposure to ambient moisture (pre-dipping). Which pad is used depends on the configuration of the test but may include leucocytes, nitrites, or protein. The application can utilise an algorithm with these pads to detect for the presence of moisture which can be indicative of the integrity of the dipstick. This may indicate damage or tampering to the packaging 100, 200, 300, that the strip has been left outside of the packaging for an extended period prior to use, or that the strip has been previously dipped.

Any of the aforementioned features can be included in any of the following embodiments, as appropriate.

In the embodiments of FIGS. 1 and 2, the testing area 103, 203 comprises testing region(s) in the form of colour changing pads 109, 209 which change colour in response to the presence of indicators in applied urine. The testing pads are surrounded or bordered by a background area 145, 245. Urine can be applied directly to colour change pads 109, 209 by expulsion from a user, or the colour change pads 109, 209 can be dipped into a urine sample by dipping the card 100, 200 into the urine sample. Colour change pads 109, 209 can be used in testing for conditions including urinary tract infections, diabetes, or glucose levels for diabetic screening or monitoring, and metabolic disorders, kidney disease, liver disease, dietary disorders, and pregnancy term complications, amongst others. In an example, the colour change pads can detect, amongst others, the presence of leucocytes, nitrites, protein, glucose, ketones, urobilinogen, bilirubin, erythrocytes, haemoglobin, creatinine, microalbumin, as well measure specific gravity and pH. These can be used in combination, for example, to identify a pathological condition relevant to a disease. Reagents within the colour change pads react with an analyte related to the condition being tested for (if present in the urine or bodily fluid) to create a colour change. The type and extent of the colour can be indicative of the amount of analyte present. In an example, a testing equipment for a urinary tract infection uses a leucocyte pad, a nitrite pad and a pH pad. The number of colour change pads 109, 209 required can vary with the test for which the colour change pads are to be used.

In the embodiment of FIG. 3, the testing area 303 comprises testing region(s) in the form of one or more lateral flow strips 309. The lateral flow strip(s) 309 are sensitive to indicators in urine and present a line indicative of whether the analyte is present in the applied urine. Lateral flow strips can be used in testing for pregnancy, drug misuse, testing for hormones or antibodies in conditions where these provide diagnostic support such as ovulation health, prostate specific antigen levels, malaria, infertility, sexually transmitted infections, and diabetes HbA1c, amongst others. Lateral flow strips are sensitive to an analyte respectively associated with the condition being tested for being present in the applied urine or bodily fluid. An analyte can, for example, include a hormone, a small protein, a macroprotein, or an antibody. The urine is applied by dipping the lateral flow strip(s) 309 into a urine sample, or as a direct application by the user mid-flow. In an example, a lateral flow strip 309 is a immunochromatographic assay. This strip is composed of capillary beds capable of spontaneously transporting fluid (eg Urine) along its length. These capillary beds may be formed or porous paper or polymer. Each lateral flow strip 309 has a region of antibodies specific to the analyte of interest (that is, an analyte associated with the condition for which the test is being carried out) immobilised on the surface of the lateral flow strip in a set location, as well as conjugated to a colour reporter and desiccated within an absorbent pad. During the course of the test process, these antibodies bind strongly to the analyte of interest creating a visual band (or line), the density of which is related to the concentration of the analyte present. Each lateral flow strip will have a test region and a control region, each having one or more area or immobilised antibody; these are not visually obvious prior to doing the test. A control line will directly bind the colour reporter to provide an indication that the test has been successful. A test line will bind the analyte of interest, if present, which will have already bound the colour reporter (this is reversed in the case of competitive assays). The location and number of these lines can vary depending on the test that is being performed, but are predetermined and known within the application, for example from the machine readable information or related to the QR code 311.

In the embodiment of FIGS. 1a to 1j, the body 105 is made of two layers of material adhered together. The layers can be any of the previously described body 105, 205, 305 materials. The handling indicator 107 is presented on the surface 133 of a frontward layer 119 of the two layers. A rearward layer 121 is adhered to the opposite side of the frontward layer 119.

Figure 1D:
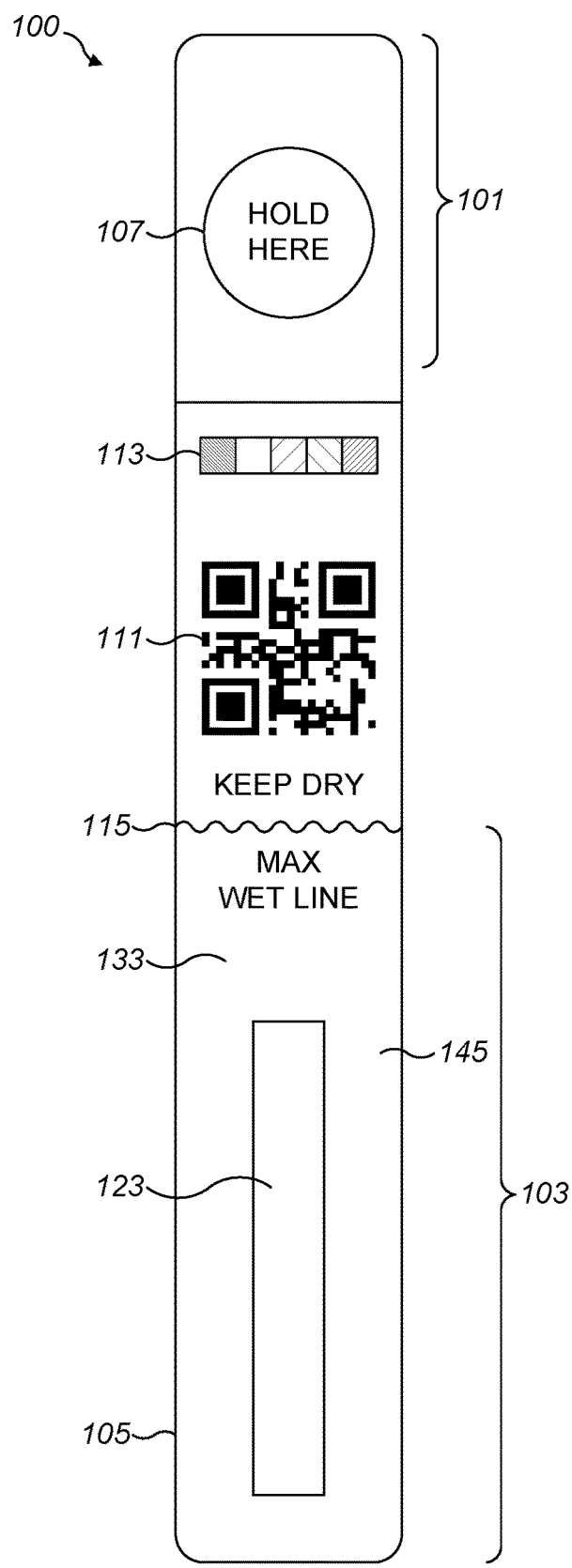
FIG. 1d shows a plan view of the front side of an application-analysable bodily fluid testing equipment according to the first embodiment with the testing pads removed.
Figure 1E:
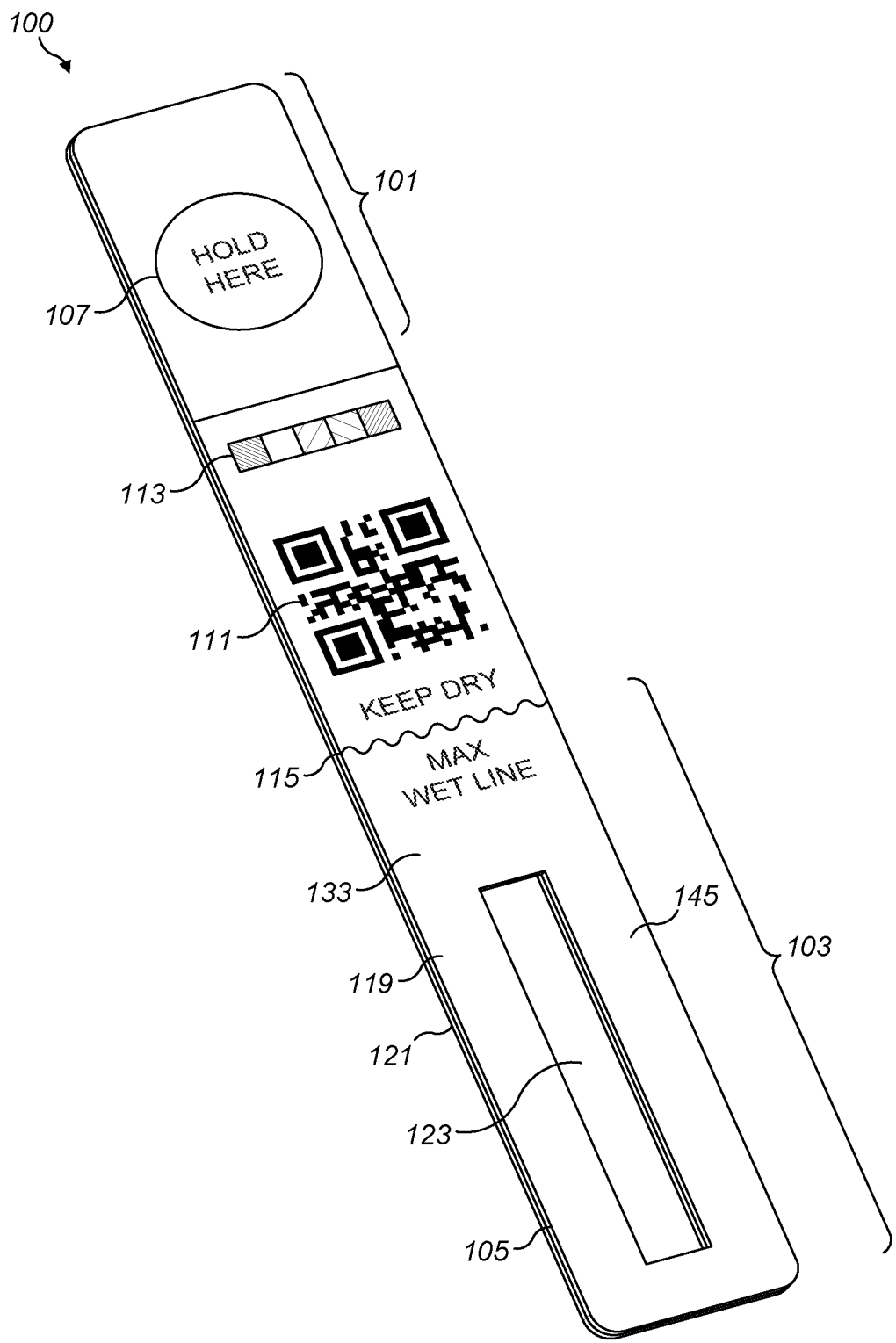
FIG. 1e shows a perspective view of the front side of an application-analysable bodily fluid testing equipment according to the first embodiment with the testing pads removed.
Figure 1F:
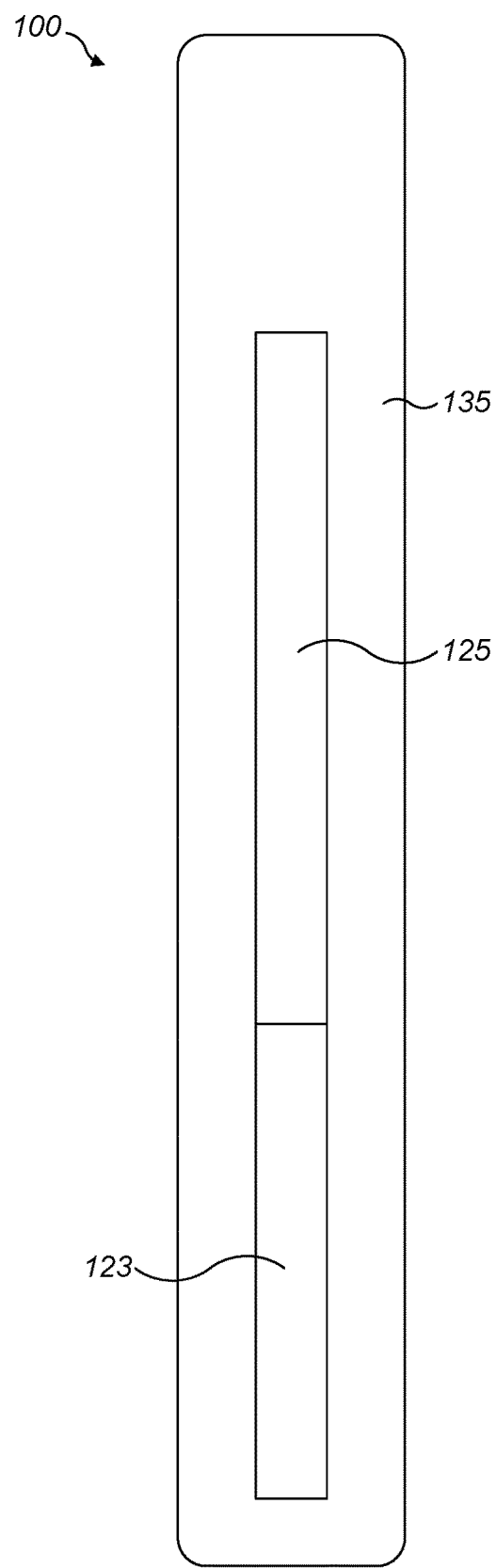
FIG. 1f shows a plan view of the rear side of an application-analysable bodily fluid testing equipment according to the first embodiment with the testing pads removed.
Figure 1G:
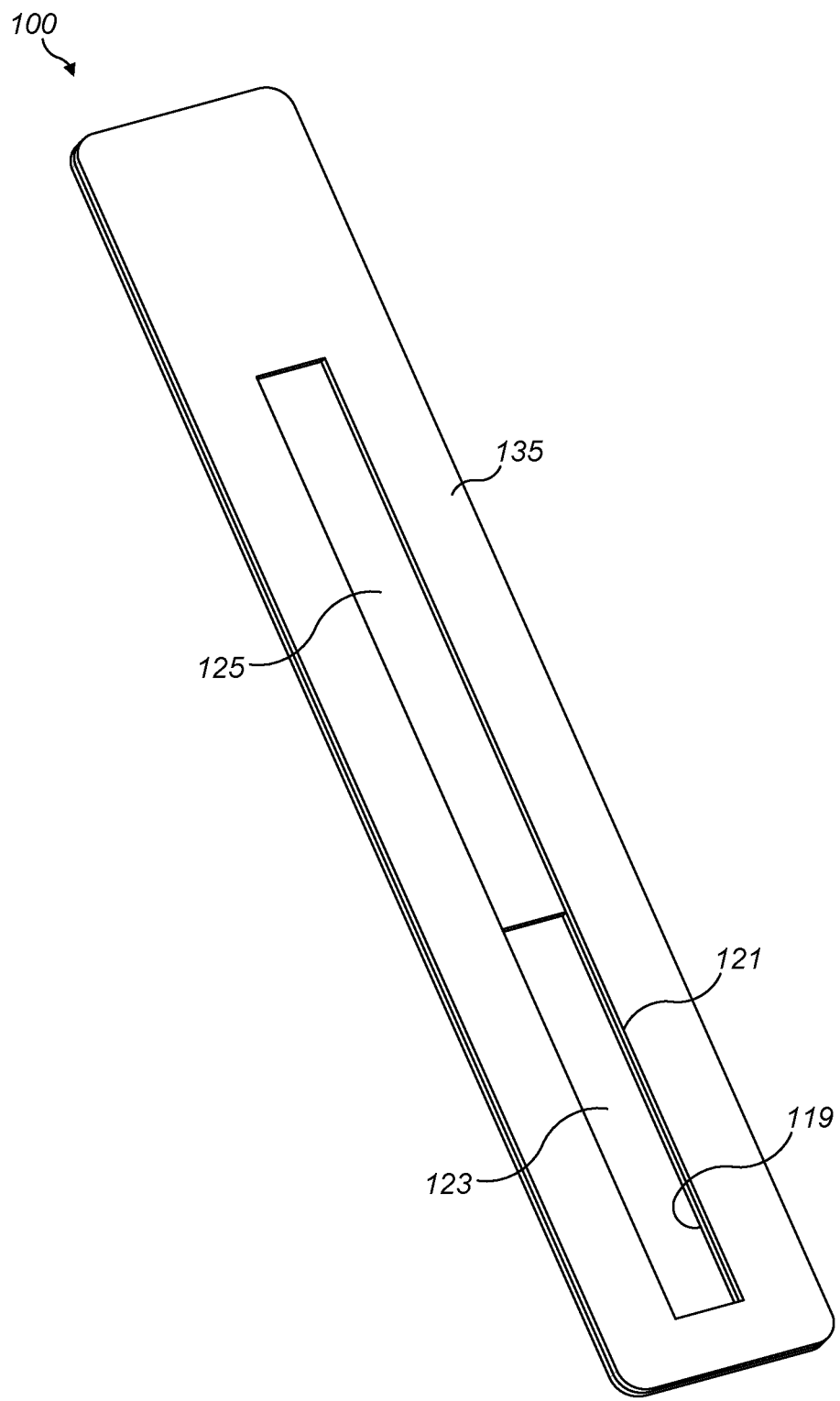
FIG. 1g shows a perspective view of the rear side of an application-analysable bodily fluid testing equipment according to the first embodiment with the testing pads removed.
Figure 1H:
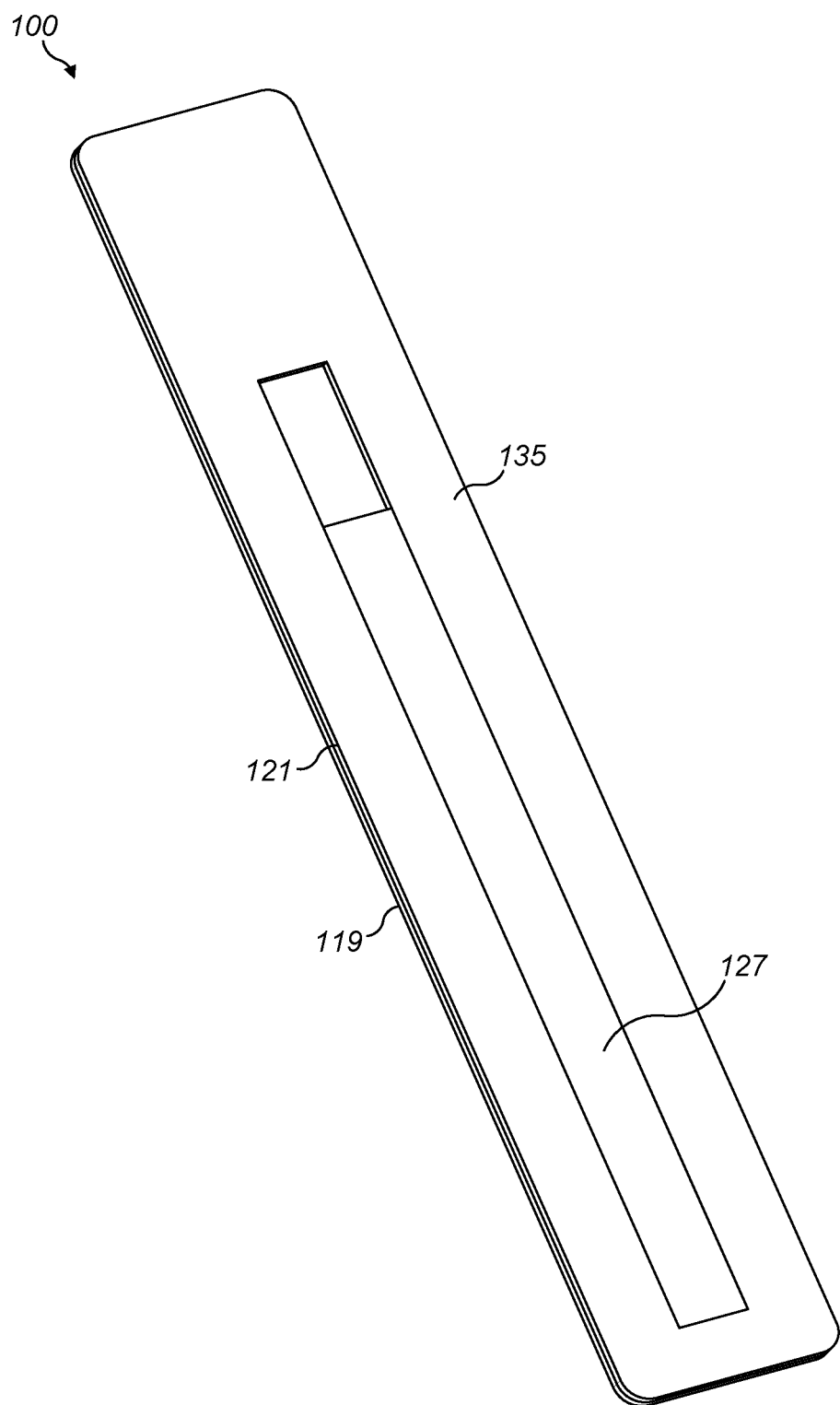
FIG. 1h shows a perspective view of the rear side of an application-analysable bodily fluid testing equipment according to the first embodiment with the testing pads included.
Figure 1I:
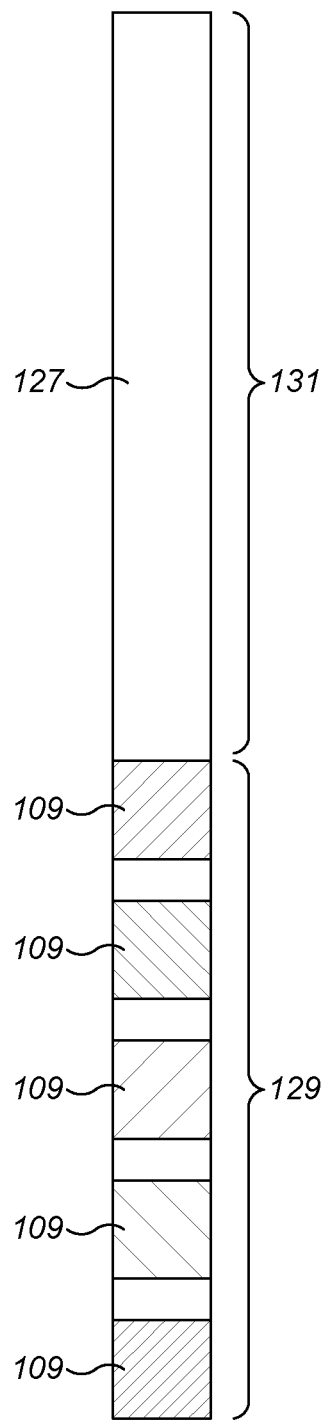
FIG. 1i shows a plan view of the testing pads of an application-analysable bodily fluid testing equipment according to the first embodiment.
Figure 1J:
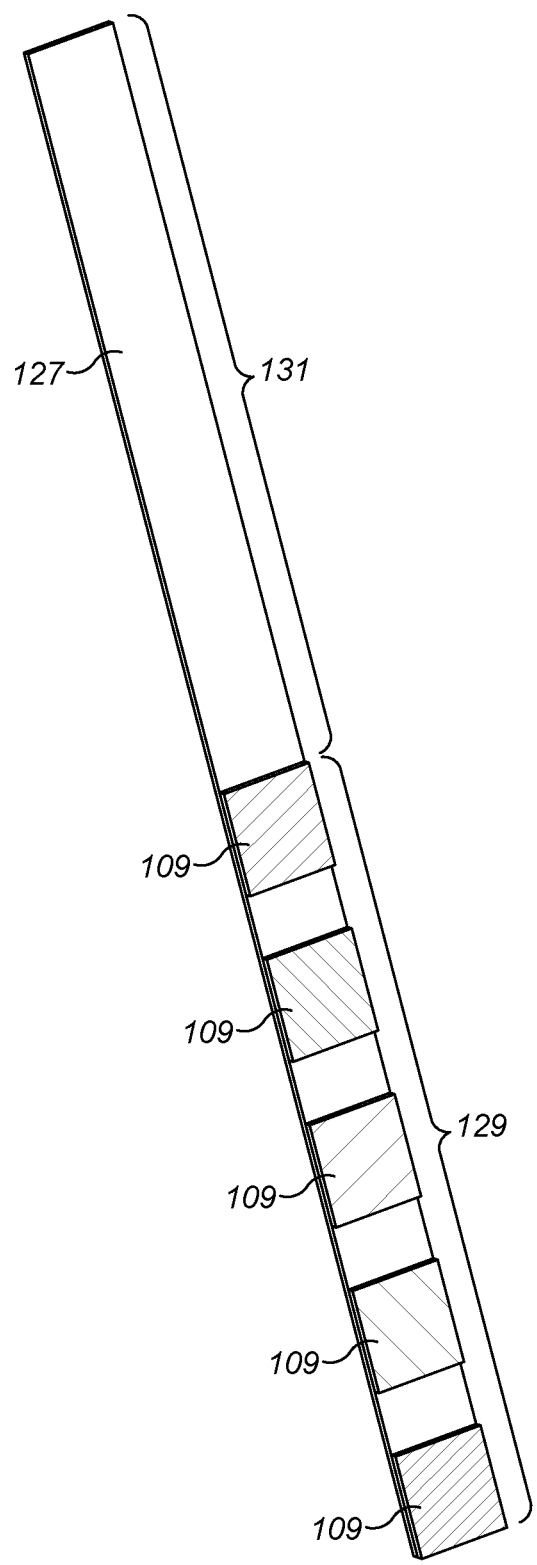
FIG. 1j shows a perspective view of the testing pads of an application-analysable bodily fluid testing equipment according to the first embodiment.

The testing pad(s) 109 are arranged on the surface of a strip 127 to define two portions of the strip 127, a first portion 129 where the testing pad(s) 109 are arranged, and a second portion 131 where the testing pad(s) 109 are not arranged, as shown in FIG. 1i and 1j. The strip 127 is affixed the body 105 by the second portion 131 of the strip 127. As shown in FIGS. 1*d* and 1*e*, a first window 123 is cut away from the testing area 103 of the frontward layer 119 of the body 105; the first window 123 is at least equal in size and shape to the first portion 129 of the strip 127. A second window 125 is cut away from the rearward layer 121; the second window 125 is at least equal in size and shape to the combined first 129 and second 131 portions of the strip 127, as shown in FIG. 1*f* and 1*g*. The first window 123 overlays the second window 125 when the frontward 119 and rearward 121 layers are affixed to one another defining an overall cutaway window in the body 105 of approximately equal size and shape to the first portion 129 of the strip 127. This overlaying also forms a recessed portion in the rearward layer 121 approximately equal in size and shape to the second portion 131 of the strip 127.

The second portion 131 of the strip 127 is adhered in the recess, to the back side of the frontward layer 119 (i.e. the surface of the frontward layer 119 opposite the surface 133 upon which the handling indicator 107 is presented) such that the testing pad(s) 109 are presented through the cutaway window on the same side of the body 105 as the handling indicator 107. The second portion 131 is adhered to the back surface of the frontward layer 119 by any suitable conventional affixer.

Advantageously, testing regions that use existing technologies can be mounted to the body 105 to form the card. Moreover, a single design of body 103 can be used for a variety of different types of testing strips 127 with different types of testing pads 109 relating to different conditions can be mounted to a single design of body 103. Only the type of strip and any information presented on the body need be changed between manufacturing cards 100 designed for testing different conditions. This simplifies and streamlines manufacturing considerations.

The combined thickness of the strip 127 and the testing pad(s) 109 is approximately equal to the combined thickness of the layers 119, 121 of the body 105, and the rearward layer 121 of the body 105 is approximately equal in thickness to the second portion 131 of the strip 127. In this way, when the strip 127 is mounted to the body 105, the testing pad(s) 109 are approximately flush to the surface 133 of the frontward layer 119, as shown in FIG. 1*b* and the strip 127 is approximately flush to the surface 135 of the rearward layer 121 of the body 105 as shown in FIG. 1*h*. This gives a consistent surface profile, or height, on both surfaces 133, 135 of the card 100.

Figure 2A:
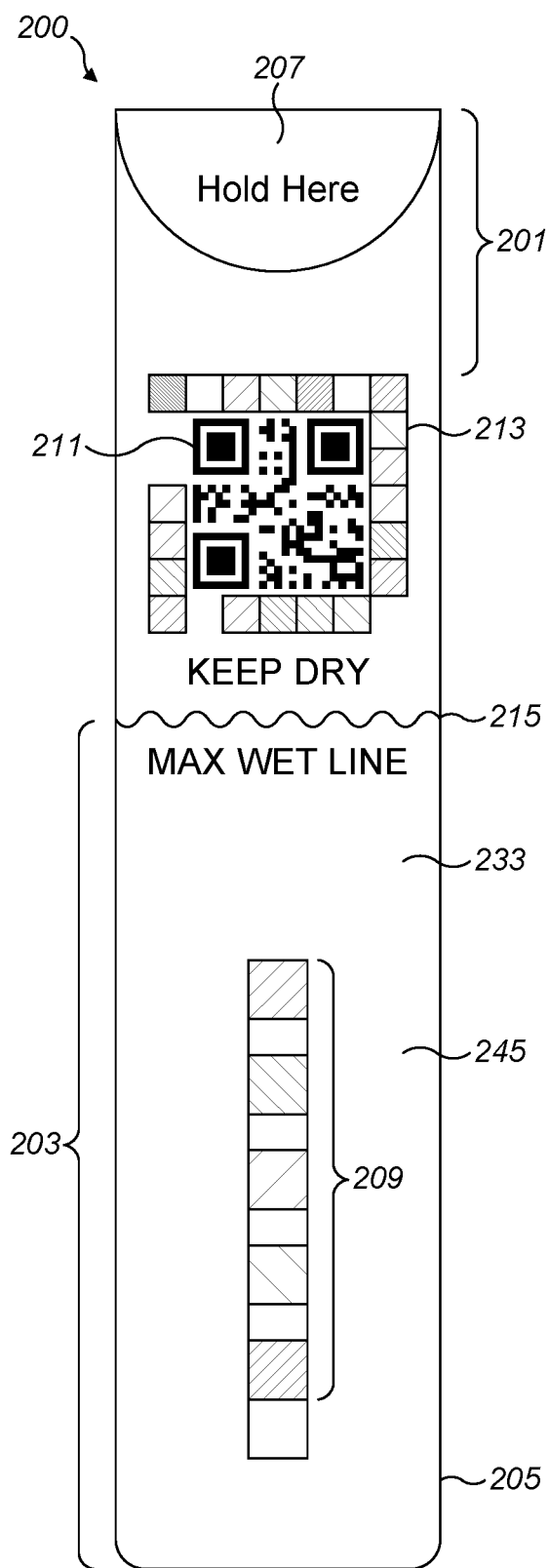
FIG. 2a shows a plan view of the front side of an application-analysable bodily fluid testing equipment according to a second embodiment.
Figure 2B:
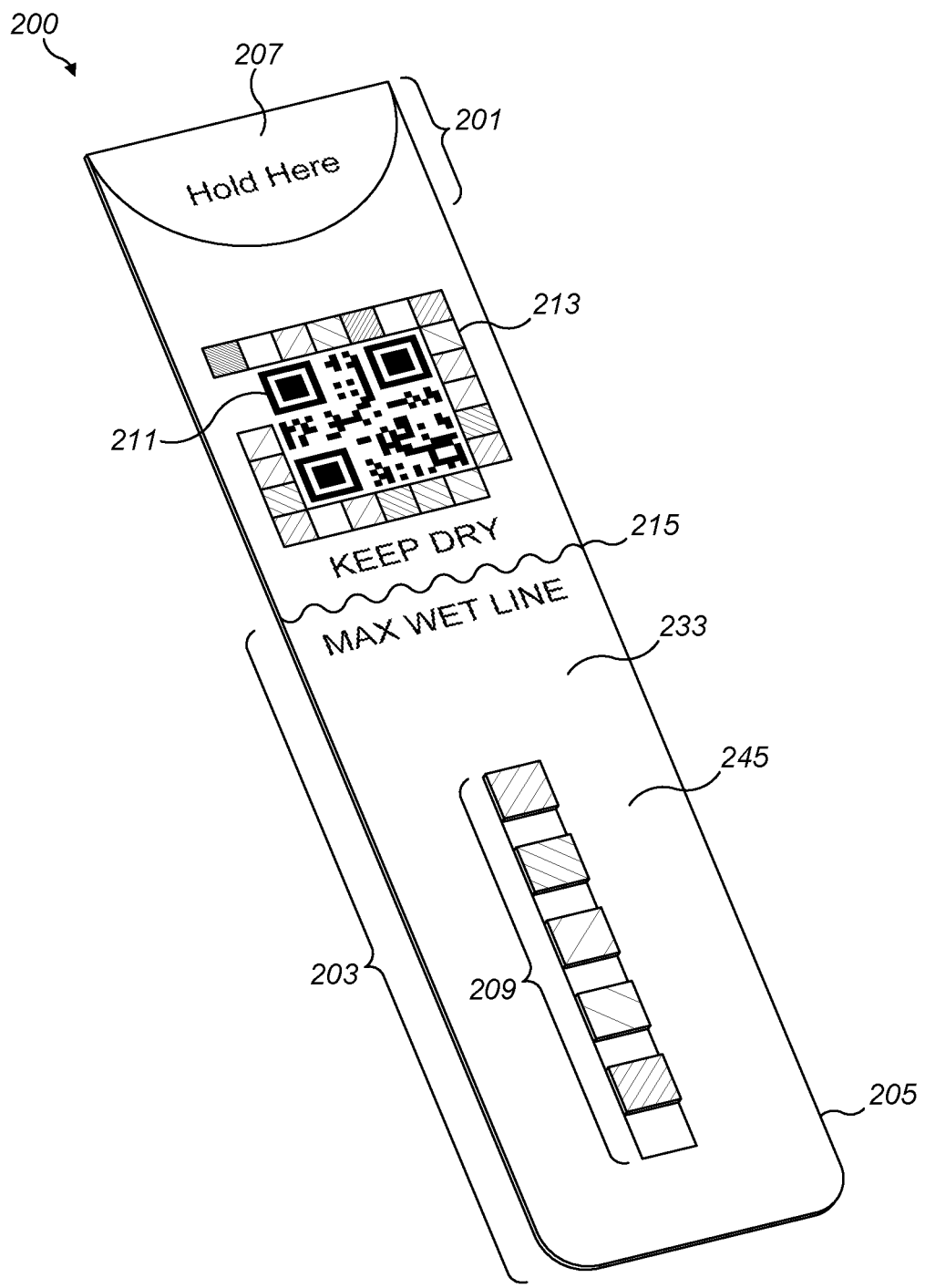
FIG. 2b shows a perspective view of the front side of an application-analysable bodily fluid testing equipment according to the second embodiment.
Figure 2C:
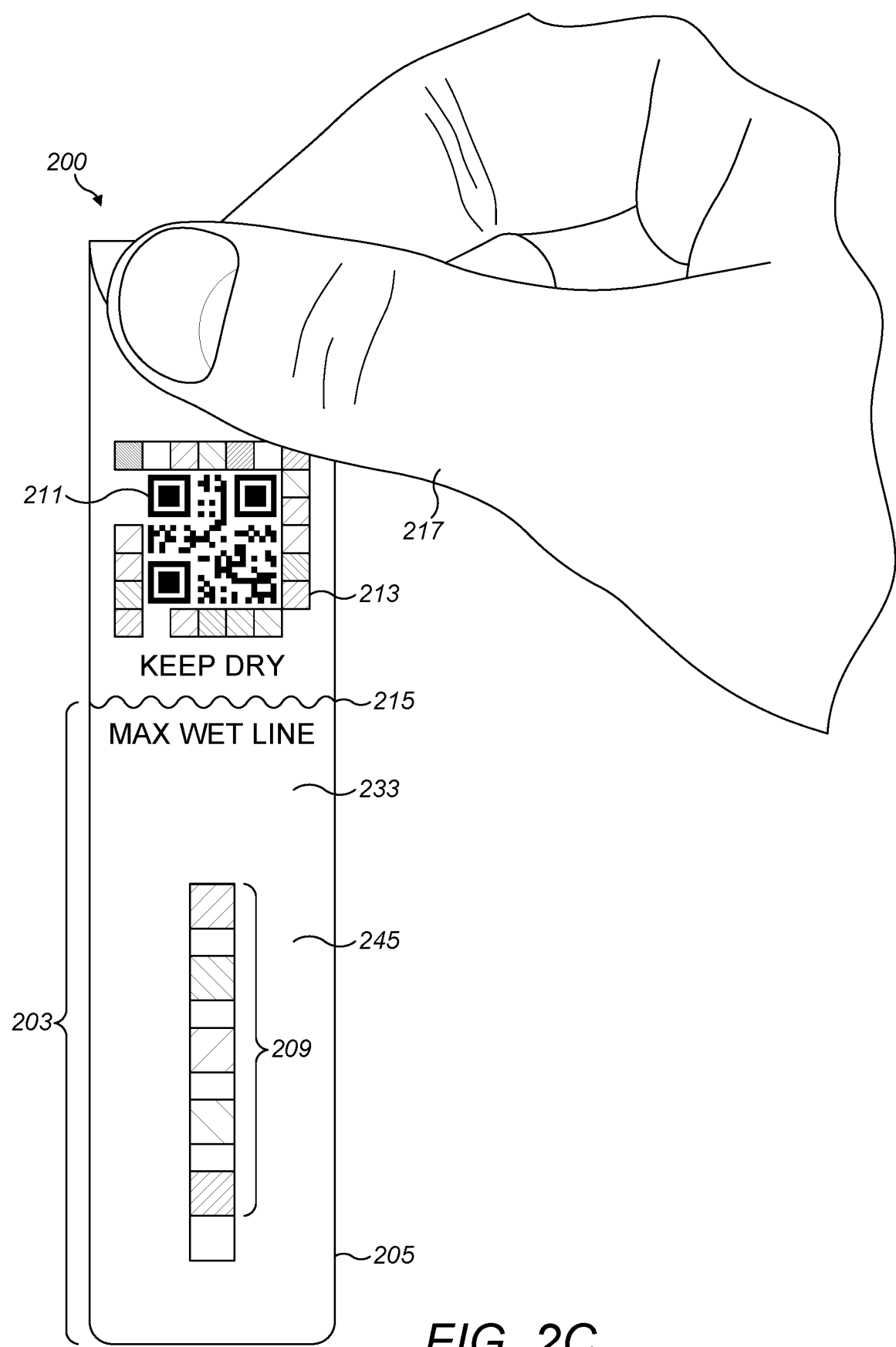
FIG. 2c shows a diagram of a hand holding an application-analysable bodily fluid testing equipment according to the second embodiment.

In an alternative embodiment, as presented in FIGS. 2*a* to 2*c*, the testing pad(s) 209 are directly mounted on to the same surface 233 of the body 205 as that upon the handling indicator 207 is presented. The testing pads are adhered to the surface 233 in the testing area 203 by any suitable conventional affixer. The testing pad(s) 209 may be arranged on a strip, with the strip adhered to the surface 233 of the body 205.

Figure 3A:
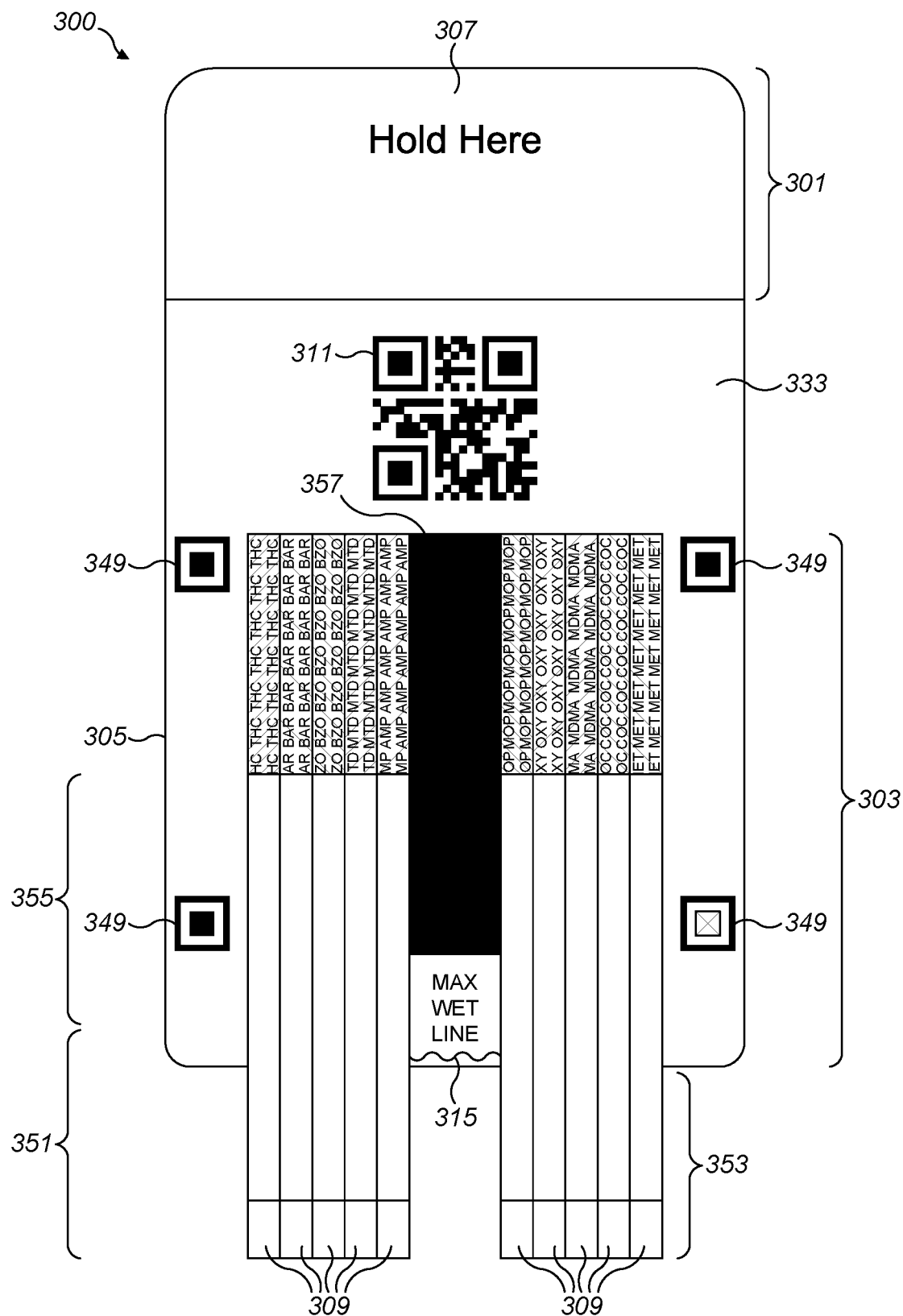
FIG. 3a shows a plan view of the front side of an application-analysable bodily fluid testing equipment according to a third embodiment.
Figure 3B:
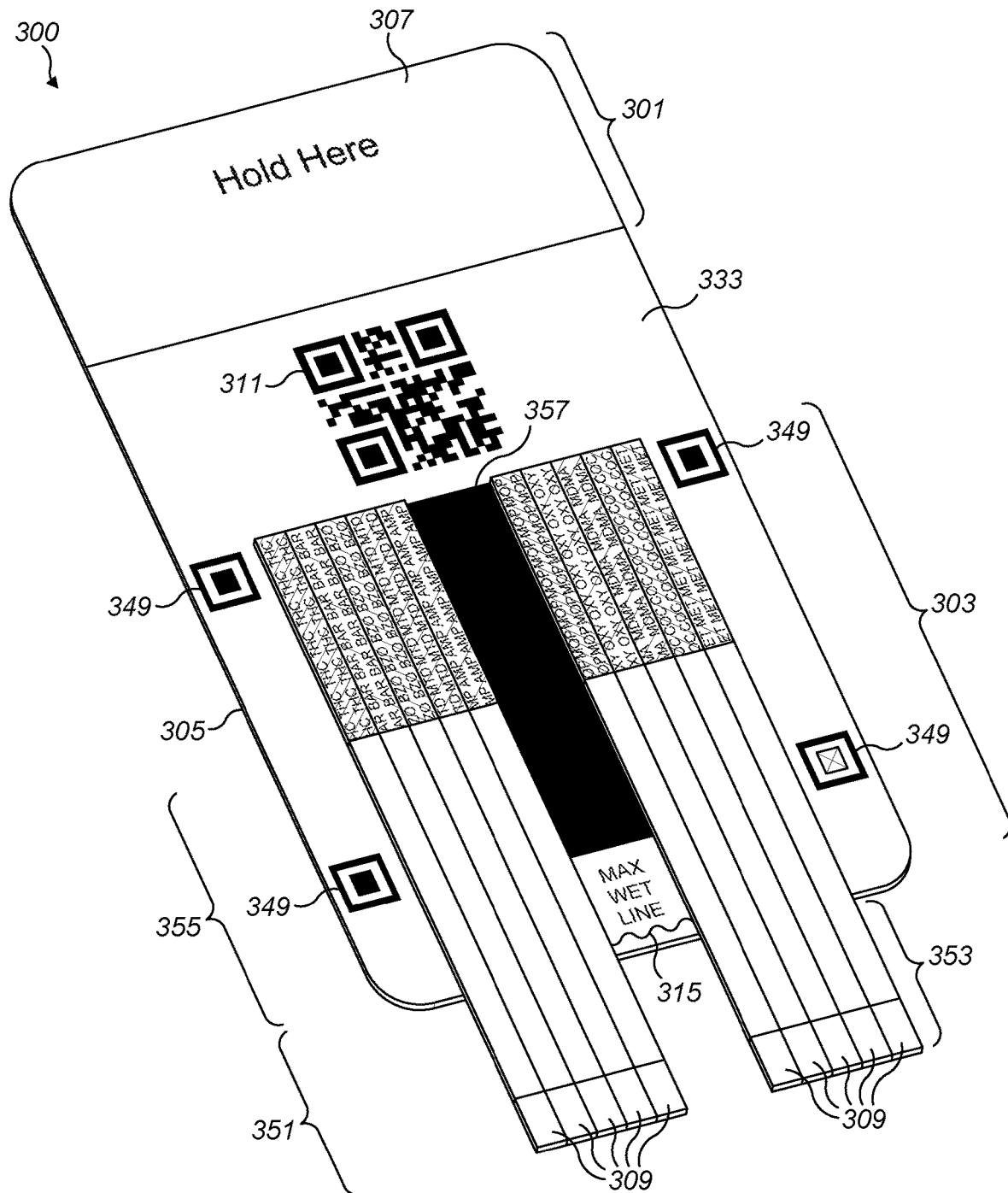
FIG. 3b shows a perspective view of the front side of an application-analysable bodily fluid testing equipment according to the third embodiment.
Figure 3C:
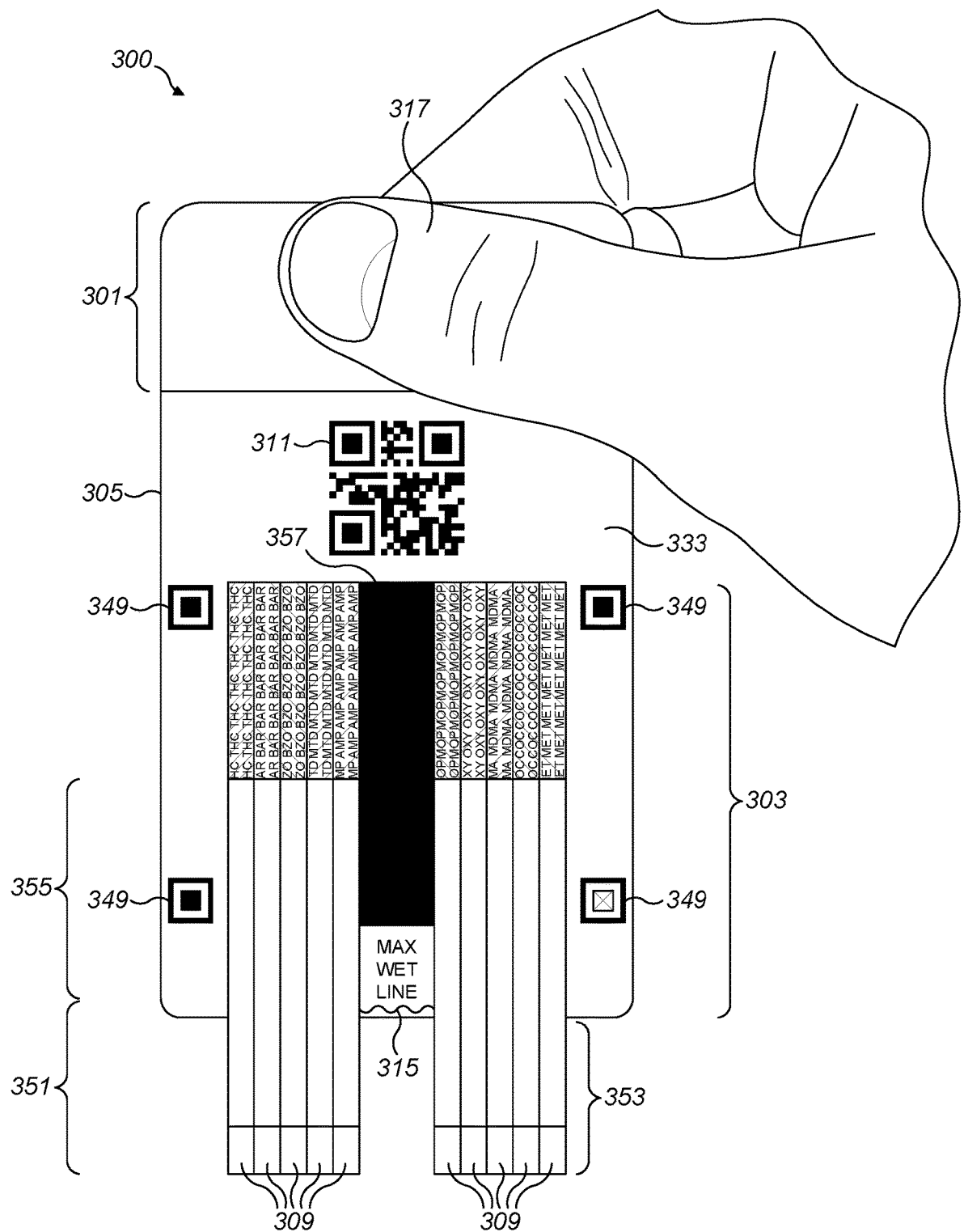
FIG. 3c shows a diagram of a hand holding an application-analysable bodily fluid testing equipment according to the third embodiment.

In another alternative embodiment, one or more lateral flow strips 309 are affixed to the body 305, as shown in FIGS. 3*a* to 3*c*. The lateral flow strip(s) 309 are affixed to the same surface 333 of the body 305 as that upon which the handling indicator 307 is presented. In FIG. 3, ten lateral flow strips 309 are included, although a larger or smaller number of lateral flow strips 309 could instead be included. The lateral flow strips comprise an analysis region 355, within which the line appears if the analyte for which the lateral flow strip is sensitive is present in the bodily fluid sample. Liquid is drawn by a liquid uptake region 351 of the lateral flow strip 309 to the analysis region 355.

The lateral flow strip(s) 309 are adhered to the surface 333 of the body 305, in the testing area 303, using any suitable conventional affixer.

A portion 353 of the liquid uptake region 351 of each lateral flow strip 309 extends beyond the edge of the body 305. This allows for the lateral flow strip(s) 309 to take up urine from a container without wetting the body 305 of the card when the liquid uptake region 351 is dipped into the urine.

One or more anchor points 349 are displayed on the same surface 333 of the body as that to which the lateral flow strip(s) are adhered. In the example presented in FIG. 3, four anchor points 349 are arranged substantially in the corners of the testing area 303. It will be readily understood to the skilled person, however, that any suitable number of anchor points may be included.

During analysis of the image data of the card 300, the associated application locates the anchor points 349 and uses these to identify the analysis region 355 of the lateral flow strips. The anchor points 349 are indicia presented on the first surface 333 of the body portion 305. One of the anchor points can be distinct from the other anchor points, for example the distinct anchor point includes a different colour to the other anchor points. The application can use the distinct anchor point to identify the orientation of the application-analysable bodily fluid testing equipment in the image data. Advantageously the anchor points 349 allow for the associated application to determine the position of the analysis region 355 of the one or more lateral flow strips 309 during analysis of the card 300. This expedites the processing and improves the accuracy of results of the analysis. An anchor bar 357 is displayed on the same surface 333 of the body as that to which the lateral flow strip(s) are adhered. The anchor bar 357 is arranged substantially centrally to the card 300 between two groups of lateral flows strips 309. In an example, the anchor bar 357 is a solid black rectangle. During analysis of image data of the card 300, the associated application locates the anchor bar 357 and uses it in the identification of the analysis region 355 of the lateral flow strips. In an example, the application uses a combination of the machine readable label 311, the one or more anchor points 349 and the anchor bar 357 to determine the position of the analysis region 355 of the lateral flow strips 309.

The lateral flow test provided by the lateral flow strip(s) 309 is useful for the identification of drug abuse and misuse. Multiple lateral flow strips 309 can be included; in the case of drug abuse and misuse the strips 309 can relate to the identification of different drugs in the urine sample. In an example, the lateral flow strips can be sensitive to indicators of drugs including cannabis or marijuana (THC), amphetamine, cocaine, ecstasy, methamphetamine, morphine, heroin, fentanyl, synthetic cannabinoids, methcathinone, ketamine LSD and acids and/or their metabolites, amongst others. The equipment can therefore be used to identify whether the person who has expelled the bodily fluid has taken part in drug abuse/drug misuse. Advantageously the multiple lateral strips allow for a single application of urine to be used to identify the presence of indicators of relating to a plurality different drugs. In the case of drug misuse and abuse identification, a lateral flow strip is sensitive to a metabolite of the drug being tested for in the bodily fluid such as urine.

There will now be described a method of using the equipment described with reference to the previous embodiments. In operation, a user holds the card 100, 200, 300 by the handling indicator 107, 207, 307 and applies urine (or any other suitable bodily fluid) by direct expulsion from their body 105, 205, 305 (in the case of the embodiments of FIGS. 1 and 2), or by dipping the card 100, 200, 300 into urine (in the case of the embodiments of FIGS. 1, 2 and 3).

In response to indicators in the urine, the colour change pad(s) 109, 209 may change colour, or a line may appear in the case of the lateral flow strip(s) 309.

Whilst still holding the card 100, 200, 300, the user opens a related application on an electronic device, such as a smartphone. The application prompts the user to capture an image of the card 100, 200, 300, using a camera on the electronic device, whilst the user is still holding the card 100, 200, 300. The application can display a frame or outline on the device display to guide the user to correctly orientate the card 100, 200, 300 for the image capture. The application may display a countdown timer to the user prior to capturing the image. The time period of the countdown timer can correspond to an amount of time needed for a colour to sufficiently change (i.e. the time it takes for the result to develop) for colour change pads 109, 209, or for the reagents and urine to migrate along the lateral flow test to form one or more lines 309. The length of time can be set according to the type of test being carried out, as determined from the machine readable information 111, 211, 311. The application additionally limits the period of time after dipping that the strip may be read to ensure the optimum scanning time window.

The application can identify the type of test, for example urinary tract infection tests, diabetes, or glucose levels for diabetic screening or monitoring, and metabolic disorder tests, kidney disease tests, liver disease tests, dietary disorder tests, pregnancy term complication tests, pregnancy tests, drug misuse tests, and hormonal and antibody related conditions such as ovulation health test, prostate specific antigen level tests, malaria tests, infertility tests, sexually transmitted infection tests, and diabetes HbA1c tests, amongst others, from the machine readable information 111, 211, 311 (such as a QR code) presented on the card 100, 200, 300 by accessing equipment information associated with the machine readable information 111, 211, 311 in storage accessible by the application. Image data of the card 100, 200, 300 is captured by the camera. The application executes an algorithm to analyse any colour change in the case of colour change pad(s) 109, 209 or the presence, position and/or intensity of a line formed in the case of lateral flow strip(s) 309 in the image data.

In the case of the colour change pad(s) 109, 209, the application can execute a colour calibration algorithm prior to analysing a colour change in the colour change pad(s) 109, 209.

By analysing the colour change of the colour change pad(s) 109, 209 compared to predefined colours, or the presence, position and/or intensity of a line formed in the case of lateral flow strip(s) 309, based upon the captured image data, the application determines whether the condition for which the user is testing is present. Example conditions that can be tested for include urinary tract infections, diabetes, or glucose levels for diabetic screening or monitoring, and metabolic disorders, kidney disease, liver disease, dietary disorders, pregnancy term complications, pregnancy testing, drug misuse, and testing for hormones or antibodies in conditions where these provide diagnostic support such as ovulation health, prostate specific antigen levels, malaria, infertility, sexually transmitted infections, and diabetes HbA1c, amongst others. If the identifiers of such conditions are present in the urine sample, the application identifies this using the image data of the colour change pad(s) 109, 209 or lateral flow strip(s) 309 and the application outputs this information to the user on the display of the device.

Advantageously, a user of the equipment can apply a bodily fluid, such as urine, to the testing region(s) of the equipment and then capture image data with an electronic device for analysis of the bodily fluid applied to the testing region(s), using an application executable on the device, without having to put the equipment down, or place it on a surface, between applying the bodily fluid and the analysis being carried out. This prevents contamination to the equipment from a surface, as well as preventing contamination to a surface from the bodily fluid applied to the equipment. This also improves hygiene.

Additionally, in the case of the equipment having a pad that can be used for an integrity check eg a leucocyte, nitrite or protein pad, if the card packaging for 100, 200, 300 has been tampered with, damaged, or the dip has been left out for an extended period prior to use or already used, the application determines this from the "integrity" pad and alerts the user halting further progress.

Figure 4:
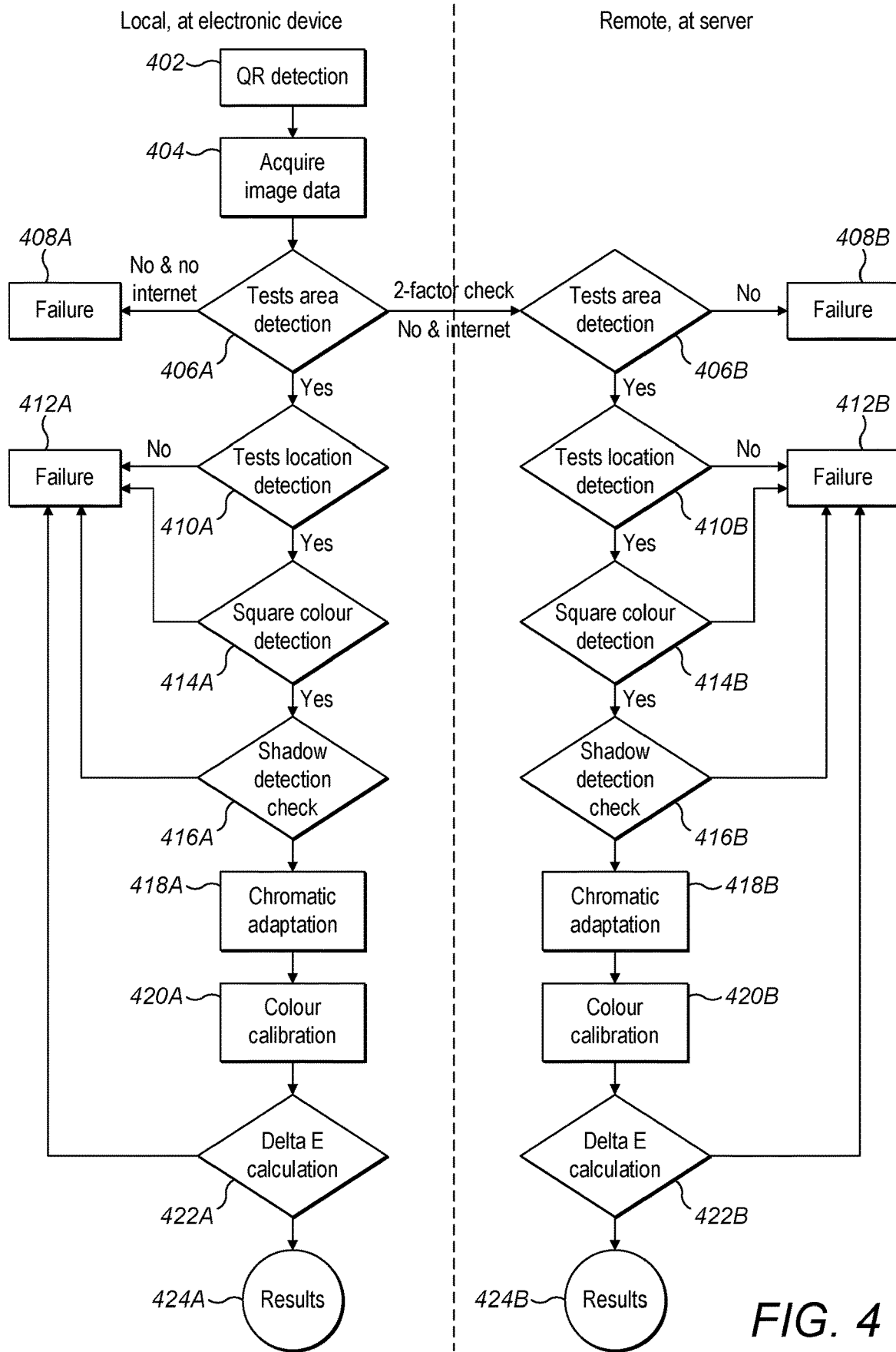
FIG. 4 is a flow diagram of processing steps involved in analysing image data of an application-analysable bodily fluid testing equipment.

FIG. 4 depicts a flow diagram of the processing steps involved in an algorithm for analysing colour change in the colour change pad(s) 109, 209 (or testing region(s)) of the testing equipment (or card) described with reference to FIGS. 1 and 2. In the present description multiple colour change pads are described. However the skilled person will readily understand that the same steps can be applied when using a card with only one colour change pad. Likewise, the description is directed to urine analysis, however the skilled person will readily understand that the described process steps can also be applied to the analysis of other suitable bodily fluids.

The user holds the card and applies urine to the testing region or colour change pad(s) 109, 209 of the testing equipment or card. An application executed on an electronic device, such a smartphone, utilises a camera of the electronic device to capture image data of the card. The user directs the camera of the electronic device toward the card, which may be held or placed on a surface, so that the application displays a live image of the card, as detected by the camera, on a display of the electronic device.

At step 402 the application detects the presence of a machine readable label 211, such as a QR code, on the card using an image detection algorithm at the electronic device suitable for identifying a QR code. For example, the algorithm determines the location of the QR code as being in the machine readable label area 547; the box 547 presents a visual representation of the area in which the QR code reading takes place. The algorithm decodes an image of the QR code into information. The machine readable label 211 is used to indicate the type of card. The application scans the QR code using the camera of the electronic device. The application determines, from the machine readable information, equipment information relating to the type of test for which the equipment is arranged. The application compares the machine readable information to pre-stored equipment information to identify equipment information associated with the machine readable information. The equipment information may be stored locally at the electronic device in storage accessible by the application.

Alternatively the application can communicate the machine readable information with a server in connection with the electronic device. The server can provide the associated equipment information to the electronic device for use with the application.

From the equipment information, by way of the machine readable label 211, the application determines the type of testing equipment or card for which the image data has been captured, i.e. the application determines which type of urine test the card is used for from the machine readable label 211, for example urinary tract infection tests, diabetes, or glucose levels for diabetic screening or monitoring, and metabolic disorder tests, kidney disease tests, liver disease tests, dietary disorder tests and pregnancy term complication tests, amongst others. Other examples of equipment information can include, but are not limited to, the size and/or aspect ratio of the card, the layout of colour change pads, sizes of the colour change pads, distances between the colour change pads, distances between the colour change pads and other features on the card such as the QR code, the type or types of colour change pad, reference colours for the colour change pads and others. That is, using the machine readable label 211, the application identifies information that corresponds to the machine readable label 211, i.e. information that corresponds to different types of card. This determined information is used to determine properties such as card geometries, colour change pad layouts and reference colours that should be used when determining the colour change in the colour change pads 109, 209 due to the application of the urine. Different types of card may have colour change pads of different sizes and/or shapes that can be positioned at different locations on the card; determining the type of testing equipment can aid the application in determining the position of the colour change pads based upon predetermined information relating to the positions of the pads for different types of card. The machine readable information may also be used as an anchor point to aid the locating of the testing regions or sensitive regions, to provide LOT information including batch number and expiry date, for use in lighting conditions testing, to identify the date of manufacture and for an ID string unique to the individual strip. The QR code serialisation can also be used to identify the source of purchase (ie retailer, direct sale, healthcare provider) to improve the user experience or aftersales care.

Figure 11:
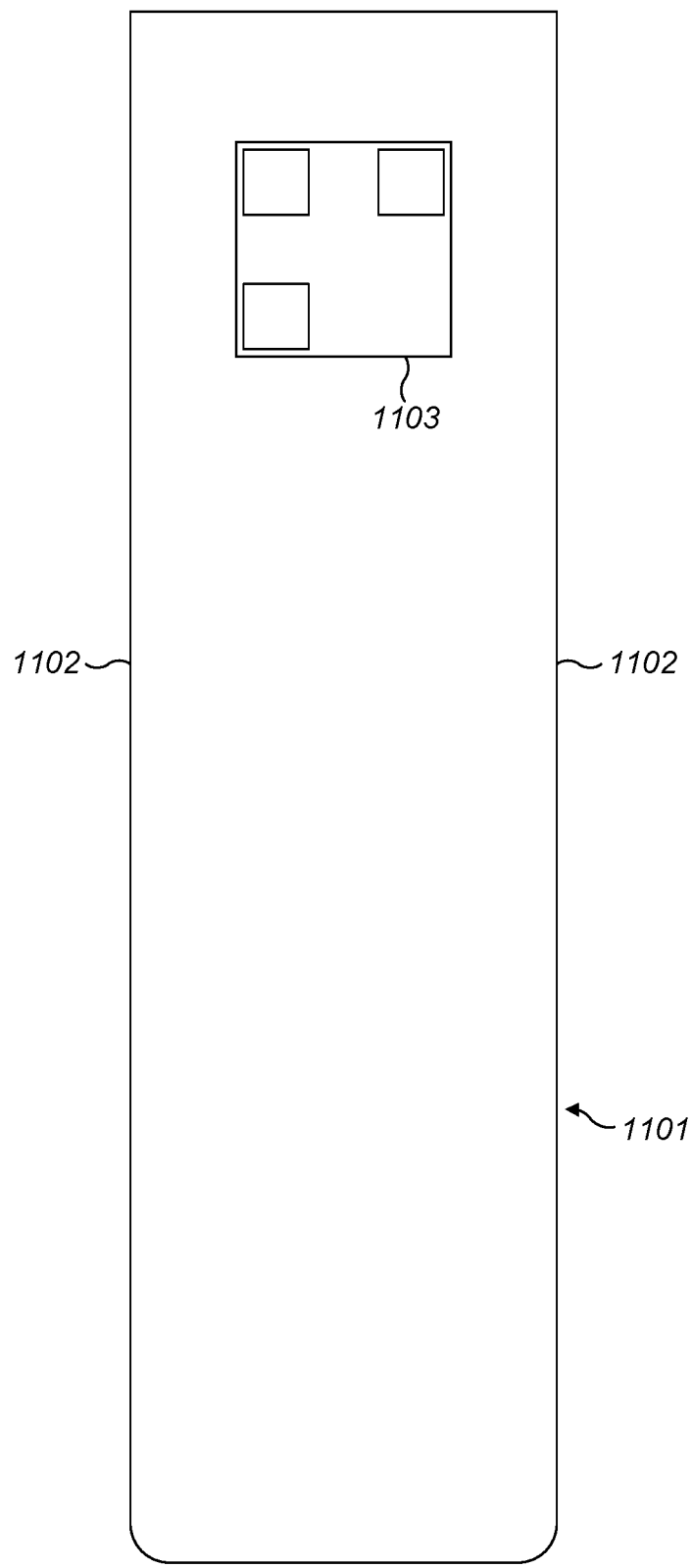
FIG. 11 is a conceptual diagram of an alignment window.

The application presents a window 1101, or box, on the display in which the user is prompted to align the card by moving the card and/or camera as necessary; FIG. 11 shows a schematic representation of such a window. The window 1101 is of a similar shape to the card so as to aid the user in aligning the edges of the card with the edges 1102 of the window 1101. This allows for the card to be accurately aligned thereby aiding the capture and processing of the image. A sub-window 1103 can be presented within the window; the sub-window 1103 can be arranged such that the user is prompted to align the machine readable label or QR code 211 within the sub-window 1103. This can improve the alignment of the card for image capture. The application detects the presence of the aligned card 200 in the window 1101 and/or the machine readable label 200 is aligned within the sub-window 1103 and automatically acquires image data of the card 200, for example by capturing a photograph of the card at step 404. Advantageously, this minimises the required user input thereby improving the usability and decreasing the risk of user error. The application can also wait for a successful ISO and focus listening before the image capture. If the machine readable label 211 is obscured, due to a finger or thumb of the user covering (or partially covering) the label 211 for example, the application may not capture the image until the machine readable label 211 is no longer obscured (i.e. the user has moved their finger or thumb away from the machine readable label 211).

In an alternative, when the card is suitably aligned in the window 1101 and/or the machine readable label 200 is aligned within the sub-window 1103, the user can instruct the application to record the image data using the camera by selecting, for example, a 'capture image' button.

Alternatively, in place of steps 402 and 404, the user can import a pre-stored photograph of the card and align it within the window by rotating and/or zooming the image as necessary. The application can then scan the QR code from the image data and access the equipment information.

At step 406A the application performs a two-factor test by determining whether the application is being executed on an iOS operating system, and by determining whether the electronic device has an active internet connection (e.g. a WiFi connection, a 4G connection, a 5G connection, or any other suitable type of internet connection).

If it is determined that the application is not being executed on an iOS operating system, and there is no active internet connection, the process proceeds to steps 408A and the application presents the user with a notification indicating that analysis cannot be carried out.

Figure 5:
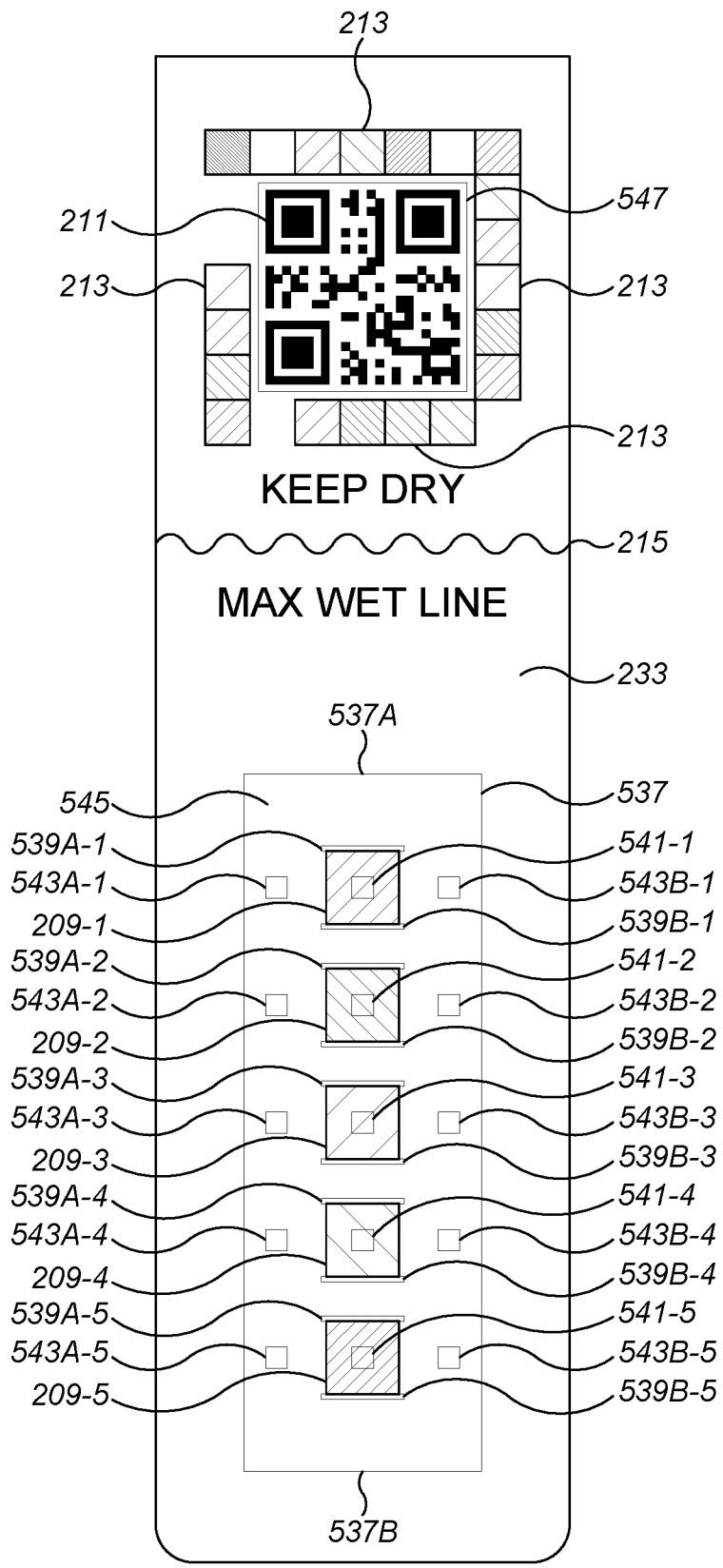
FIG. 5 is a conceptual diagram of the regions of an application-analysable bodily fluid testing equipment analysed by an application.

If it is determined that the application is being executed on an iOS operating system, the application determines a test area 537 in which the colour change pads 109, 209 are located as conceptually presented in FIG. 5. The region of the card 200 presented in FIG. 5 corresponds to the region captured within the window 1101. The test area 537 is a predetermined position in which the application can expect to find the colour change pad(s) 209. The top and bottom of each colour change pad 209, as well as the lateral position of the card 200, are specifically identified on a case-by-case basis; this allows for minor variations in manufacture, and variations in the handling and presentation to the camera of the card 200 by a user. Whilst FIG. 5 is presented according to the embodiment of FIG. 2, it will be readily understood that the same processes can be readily applied to the embodiment of FIG. 1. In an example, the position of the test area 537 is determined based upon a predetermined position within the window which encompasses the colour change pads when the card is aligned with the edges of the window. In another example, the position of the test area 537 is determined from a predetermined relationship with respect to the determined position of the QR code 211 based upon the alignment of the QR code 211 with the sub-window 1103 during image capture. That is, the application can access a stored a predetermined relationship for the test area location within the window and/or with respect to the determined position of the QR code 211. This predetermined relationship can be accessed using the machine readable information 211. Different types of card can have different test areas, for example due to differing numbers and/or types of colour change pads. For example with the machine readable information 211, the application can access, from storage associated with the application, different relationships or distances between the window and the test area, or the position of the QR code 211 and the test area 537, for different types of card. Alternatively, the application can access different relationships between the window and the test area, or the position of the QR code 211 and the test area 537, for different types of card from a server in communication with the electronic device upon which the application is being executed. In an example, the card 200 is aligned in the window 1101, and the QR code 211 is aligned in the sub-window 1103; the application can use this alignment, in combination with a known distance between the QR code 211 and the test area 537 for an aligned card 200 and QR code 211 with the respective window and sub-window, to identify where it expects the test area 537 to be based upon the position of the QR code 211.

The application may use the QR code or machine readable label 211 to identify which type of card is being used, and as such, which predetermined relationship to use and thereby where to apply the test area 537.

Advantageously, this allows for a coarse identification of the approximate location of the colour change pads 209 be determined.

Following the determination of the test area, the process continues to step 410A.

At step 410A the application determines the precise location of each of the one or more colour change pads by detecting two opposite edges 539A, 539B of each of the colour change pads, as conceptually presented in FIG. 5. The application scans the test area from a first side 537A to a second side 537B opposite the first side. The application identifies discontinuities in brightness as it scans across the test area. Discontinuities in brightness relate to a change in colour from the colour of the background area 545 of the test area (i.e. the colour of the portion 545 of test area that surrounds the colour change pads) to the colour of a colour change pad. In an example, the background colour of the test area is white, and the colour change pads are non-white.

In an example as presented in the conceptual diagram of FIG. 5, the application scans from the topmost side 537A of the test area 537 in a direction toward the bottommost side 537B of the test area 537. In another example, the application may scan from a leftmost edge of the test area to a rightmost edge.

When scanning in this direction the application identifies a first brightness discontinuity when passing from the background region 545 of the test area 537 onto a first colour change pad 209-1. This brightness discontinuity is indicative of the first edge 539A-1 of the first colour change pad 209-1. The application stores coordinates of this first edge 539A-1 using a coordinate system for the image.

The application continues scanning toward the bottommost side of the of the test area 537 and identifies a second brightness discontinuity when passing from the first colour change pad 209-1 to the background region 545 of the test area 537. This brightness discontinuity is indicative of the second edge 539B-1 of the first colour change pad 209-1. The application stores coordinates of this second edge using the coordinate system.

From the first edge 539A-1 and the second edge 539B-1, the application determines the location of the first colour change pad as being the region contained between the two edges 539A-1 and 539B-1. That is, the coordinates of the first colour change pad 209-1 are the coordinates contained between the coordinates of the first edge 539A-1 and the second edge 539B-1.

The application repeats this process when scanning toward the bottommost side of the test area in order to identify the location of the second colour change pad 209-2 using coordinates of the first edge 539A-2 and second edge 539B-2 of the second colour change pad 209-2, the third colour change pad 209-3 using coordinates of the first edge 539A-3 and second edge 539B-3 of the third colour change pad 209-3, the fourth colour change pad 209-4 using coordinates of the first edge 539A-4 and second edge 539B-4 of the fourth colour change pad 209-4, and the fifth colour change pad 209-5 using coordinates of the first edge 539A-5 and second edge 539B-5 of the fifth colour change pad 209-5. The skilled person will readily understand that this is not limited to five colour change pads, and that the process can be carried out in a similar manner for equipment comprising one or more colour change pads.

Advantageously, step 410A allows for the location of the colour change pads 209 to be accurately determined. In particular, the location of colour change pads 209 can be determined without the need to use anchor points presented on the card 200. As such, anchor points are not required on the card 200 thereby saving space on the card 200 and allowing for a reduced size of card 200.

If the edge detection is successful in detecting two opposite edges 539A, 539B of each colour change pad, the process continues to step 414A.

If the colour change pad locating fails, for example if one or more of the expected edges cannot be detected, the process proceeds to step 412A and the application presents the user with a notification, by the display of the electronic device, indicating that the processing has failed or cannot be carried out. In an example, the application can determine how many edges should be expected based upon information accessible using the machine readable label 211.

Once the location(s) of the colour change pad(s) 209 have been specifically determined, an area or sub-region of each colour change pad 209 is selected to provide a suitably representative colour sample. At step 414A, the application uses the location of each of the colour change pads, as determined in step 410A, to sample colour data of a testing sub-region 541 within each test region (i.e. each colour change pad), as conceptually presented in FIG. 5. The sampling comprises sampling the colour of the region. The sub-region 541 is a square (or any other suitable shape) that is smaller in size than the test region 209 in the image data as determined by the edge locating in step 410A, and contained within the test region. For each colour change pad 209, the application arranges the testing sub-region 541 such that it is in an area between the edges 543A and 543B of the colour change pad 209. That is, the testing sub-region is within the determined coordinate area of the colour change pad 209. The colour sampling processing is repeated for each of the colour change pads.

If the colour sampling at step 414A is successful, the process continues to step 416A. If the colour sampling fails, the process proceeds to step 412A and the application presents the user with a notification, by the display of the electronic device, indicating that the processing has failed or cannot be carried out.

At step 416A shadow detection is carried out. The shadow detection is repeated for each of the colour change pads. The shadow detection is used to remove possible interference in the colour detection of a strong locally applied light source that may cause the electronic device to cast a shadow across the card 200. The shadow detection uses background sub-regions adjacent to the colour change pad(s) (the background sub-regions, or known white regions, are described in more detail subsequently). A large discrepancy between light quality readings across multiple background sub-regions is indicative of a shadow. If shadowing is detected, the application alerts the user, and provides guidance to change the location in which the image capture for analysis is taking place; this suppresses the reporting of results from analysis when a shadow is present in the image data.

At step 418A chromatic adaption is carried out to account for varying brightness in the image data. The chromatic adaption is repeated for each of the colour change pads. The chromatic adaption uses brightness measurements at the background sub-regions adjacent to the colour change pad(s). A discrepancy in brightness across multiple background sub-regions is indicative of varying brightness in the image data. If a brightness discrepancy is detected, the application adapts the brightness across the image based upon the brightnesses at the background sub-regions.

At step 420A, the application performs a colour calibration of each sampled colour to account for effects in the sampled colours resulting from lighting conditions when the image data was captured.

Colour calibration or adjustment is achieved by taking a colour sample of the background sub-regions either side of the colour change pad 209 (such as known "white" regions) in order to provide light quality readings, including colour temperature, or light temperature, and intensity. The skilled person will readily understand that, in the present context, the terms calibration and adjustment are interchangeable. These light readings are then used to adjust the colour sampled for ambient lighting conditions. In more detail, the colour calibration is carried out on colour data of the first testing sub-region 541-1 of the first colour change pad 209-1 as sampled at step 414A. The application determines colour calibration data, such as colour or light temperatures, of first background sub-regions 543A-1, 543B-1 separate from, arranged either side of, and corresponding to, the first colour change pad 209-1 as presented in the conceptual diagram in FIG. 5. A colour or light temperature is a characteristic of a light source illuminating an object and can range from a cool temperature or 'bluish' colour to a warm temperature or 'yellowish' colour; colour or light temperature relates to the temperature at which a black body would emit radiation of the same colour. The terms colour temperature and light temperature are used interchangeably. Whilst FIG. 5 is presented according to the embodiment of FIG. 2, it will be readily understood that the same process applies to the embodiment of FIG. 1. One first background sub-region 543A-1 is arranged proximal to a first side of the first colour change pad 209-1 and the other first background sub-region 543B-1 is arranged proximal to a second side of the first colour change pad 209-1; the first side of the colour change pad 209-1 being an opposite side to the second of the colour change pad 209-1.

The background sub-regions 543A-1, 543B-1 are sub-regions of the background region 545 of the card surrounding or bordering the colour change pads 209. The background sub-regions 543A-1, 543B-1 are disposed at predetermined displacements either side of the first colour change pad 209-1 in order to sample the colour temperature(s) of the background region 545 either side of the first colour change pad 209-1. The colour change pads 209 are of a known size, and the card 200 is of a known size, for example as determined from the machine readable label 211, and due to the alignment of the card 200 in the window of the display when the image is captured, and these known sizes, as well as the determined location of the colour change pads, the application can utilise this information to arrange the background sub-regions such that they are on the background region 545 of the card 200 in the image, rather than on the colour change pad(s) 209 or away from the card 200 itself.

The background sub-regions 543A-1, 543B-1 are arranged such that a straight line extending between the two background sub-regions 543A-1, 543B-1 passes through the first testing sub-region 541-1. In an example, each of the background sub-regions 543A-1, 543B-1 is equal in size to the first testing sub-region 541-1.

The background region is substantially white in colour. The application determines a first colour temperature of the first background sub-region 543A-1 on a first side of the first colour change pad 209-1 and a second colour temperature of the first background sub-region 543B-1 on a second side of the colour change pad 209-1 opposite the first side. The application then determines a colour temperature gradient along the line using the first colour temperature and the second colour temperature as end points.

Advantageously the colour temperature of the white background region can be used to determine calibration data resulting from ambient lighting illuminating the card. This allows for the colour data to be calibrated thereby removing effects in the colour data resulting from the ambient lighting. Moreover, this removes the need to use separate colour reference charts either on the card, or captured with the image data of the card as the white background can instead be used.

Using the colour temperature gradient, and a coordinate system applied to the image, the application calculates a colour temperature at a position along the line corresponding to the position of the first testing sub-region 541-1. The application then calibrates the colour data of the first testing sub-region 541-1 using the calculated colour temperature for the first testing sub-region 541-1 to account for any distortions to colour in the image that result from the ambient lighting irradiating the card 200 when the image is captured. In an example, the application calibrates the colour data by subtracting the calculated captured light temperature from the colour data. The colour data can include descriptors, RGB values, LAB values, CMYK values amongst others.

The application then repeats the process for each of the colour change pads. That is, the application calibrates sampled colour data of a second testing sub-region 541-2 of the second colour change pad 209-2 using the second background sub-regions 543A-2 and 543B-2, a third testing sub-region 541-3 of the third colour change pad 209-3 using the third background sub-regions 543A-3 and 543B-3, a fourth testing sub-region 541-4 of the fourth colour change pad 209-4 using the fourth background sub-regions 543A-4 and 543B-4, and a fifth testing sub-region 541-5 of the fifth colour change pad 209-5 using the fifth background sub-regions 543A-5 and 543B-5. The skilled person will readily understand that this is not limited to five colour change pads, and that the process can be carried out in a similar manner for equipment comprising one or more colour change pads.

Advantageously, this colour calibration allows for the colour change pads to be analysed under varying lighting conditions such as sunlight and artificial lighting. Moreover, the gradient allows for differing lighting illuminating either side of the card to be accounted for, i.e. if two different light sources are illuminating the card from different positions. The colour calibration may utilise a camera flash associated with the camera of the electronic device when the image is captured such that the flash contributes to the ambient lighting thereby improving the image data recorded, and the sampled colour data.

In a further colour calibration technique, the colour calibration may utilise a camera flash associated with the camera of the electronic device when the image is captured. The camera flash of an electronic device such as a smartphone has a known predetermined colour temperature. Due to the proximity of the camera flash to the card 200 when the image is captured, the colour temperature of the camera flash dominates any ambient lighting effects. As such, the sampled colour data of the testing sub-regions 541-1, 541-2, 541-3, 541-4 and 541-5 can be calibrated by the application using the known colour temperature of the camera flash. In an example, the application calibrates the colour data by subtracting the colour temperature of the camera flash from the colour data. The application may utilise either or both of the colour calibration techniques.

In an alternative colour calibration technique, the application may use a colour reference chart 213 present on the card. Sampled colours of the colour reference chart 213 extracted from the image data can be compared to corresponding known predetermined colours by the application. The known predetermined colours may be accessed using information derivable from the machine readable label 211; for example, the known predetermined colours may be identified by the application using information derived from the machine readable label 211 and accessed by the application from storage accessible to the application using such information. The difference between the extracted colour from the image data of the colour reference chart 213 and the corresponding known predetermined colours can be used to calibrate the colour data of the testing sub-regions 541.

The application can utilise any individual one of the colour calibration techniques, or a combination of two or more of the colour calibration techniques.

Following the colour calibration, the process proceeds to step 422A.

At step 422A, the calibrated colour is compared to predetermined reference standards, or reference colours in storage accessible by the application. A delta E value is determined between each reference colour and the adjusted sampled colour. The reference colour with the smallest delta E value is selected as the closest matching reference colour and is used to determine the reported value. In more detail, the application compares the calibrated colour data of the calibrated sampled colours to predetermined reference colours for each colour change pad prior to the application of urine. In an example, the predetermined reference colours are stored in memory of the electronic device associated with the application. Alternatively, the predetermined reference colours can be accessed by the electronic device from a server in communication with the electronic device. The predetermined colours can be identified based upon the determination of the type of test using the machine readable label 211, as described with reference to step 404. A delta E calculation is performed by the application to determine the difference between the predetermined reference colours and the calibrated sampled colour. For each colour change pad, the reference colour with the smallest delta E value, compared to the calibrated sampled colour, is determined. That is, the closest matching predetermined reference colour to the adjusted sampled colour is calculated by being the predetermined reference colour with the smallest delta E value when compared to the adjusted sampled colour. When a condition (such as a urinary tract infection, diabetes, or glucose levels for diabetic screening or monitoring, or a metabolic disorder, kidney disease, liver disease, a dietary disorder, or a pregnancy term complication, amongst others) is being tested for using a colour change pad, an indicator of the condition in the urine will cause the colour change pad to change colour when the urine interacts with reagents in the colour change pad. If the measured analyte is present in the urine the colour to which the colour change pad changes will correspond to a reference colour which is an indicator of the presence of the condition. That is, when the closest matching predetermined reference colour to the calibrated sample colour corresponds to a predetermined reference colour representing indicators of the condition being present in the bodily fluid sample, it is determined that the indicators of the condition are present in the bodily fluid sample, i.e. the condition is present in the bodily system of the provider of the bodily fluid. Likewise, when the closest matching predetermined reference colour to the calibrated sample colour does not correspond to a predetermined reference colour representing indicators of the condition being present in the bodily fluid sample, it is determined that the indicators of the condition are not present in the bodily fluid sample, i.e. the condition is not present in the bodily system of the provider of the bodily fluid. Following the delta E calculation, the process continues to step 424A.

At step 424A, if it is determined that the indicator(s) of the condition being tested for are present in the urine sample, a result indicating that the condition is present in the bodily system of the user is output to the user, by the application, on the display of the electronic device. Advantageously, this allows for the user of the equipment to have immediate access to the results. Likewise, if it is determined that the indicator(s) of the condition being tested for are not present in the urine sample a result indicating that the condition is not present in the bodily system of the user is output to the user, by the application, on the display of the electronic device.

Returning to step 406A, if it is determined that the application is not executing on an iOS operating system, but there is an active internet connection, the process progresses to step 406B.

Devices using the iOS operating system have a colour spectrum that is consistent across such a range of devices. On the other hand, devices using an operating system such as the Android operating system have varying colour spectrums between devices. It follows that, for colour analysis purposes, consistent results are not necessarily achieved between different non-iOS devices. As such, for non-iOS devices the application forwards the image data to a server at which the processing is carried out using a consistent colour spectrum such that consistent results are achieved.

In progressing to step 406B the application forwards the image data from the electronic device to a remote server in a communication using the internet connection. The processing of the image data is then performed at the server. In an example, the server utilises a Python application programming interface to process the image data. In addition to the image data, the communication may include metadata relating to the image data. In an example, the metadata can include information related to the machine readable label 211. In another example, the machine readable label 211 may be read at the server.

The server determines a test area 537 in which the colour change pads 109, 209 are located as conceptually presented in FIG. 5. The region of the card 200 presented in FIG. 5 corresponds to the region captured within the window 1101. The test area 537 is a predetermined position in which the server can expect to find the colour change pad(s) 209. The top and bottom of each colour change pad 209, as well as the lateral position of the card 200, are specifically identified on a case-by-case basis; this allows for minor variations in manufacture, and variations in the handling and presentation to the camera of the card 200 by a user. Whilst FIG. 5 is presented according to the embodiment of FIG. 2, it will be readily understood that the same process applies to the embodiment of FIG. 1. In an example, the position of the test area 537 is determined based upon a predetermined position within the window which encompasses the colour change pads when the card is aligned with the edges of the window. In another example, the position of the test area 537 is determined from a predetermined relationship with respect to the determined position of the QR code 211 based upon the alignment of the QR code 211 with the sub-window 1103 during the image capture. That is, the server can access a stored predetermined relationship for the test area location within the window and/or with respect to the determined position of the QR code 211. This predetermined relationship can be accessed using the machine readable information 211. Different types of card can have different test areas, for example due to differing numbers and/or types of colour change pads. For example, with the machine readable information 211, the server can access, from storage associated with the server, different relationships or distances between the window and the test area, or the position of the QR code 211 and the test area 537, for different types of card. In an example, the card 200 is aligned in the window 1101, and the QR code 211 is aligned in the sub-window 1103; the server can use this alignment, in combination with a known distance between the QR code 211 and the test area 537 for an aligned card 200 and QR code 211 with the respective window and sub-window, to identify where it expects the test area 537 to be based upon the position of the QR code 211.

The server may use the QR code or machine readable label 211 to identify which type of card is being used, and as such, which predetermined relationship to use and thereby where to apply the test area 537.

Advantageously, this allows for a coarse identification of the approximate location of the colour change pads 209 be determined.

Following the determination of the test area, the process continues to step 410B.

At step 410B the server determines the precise location of each of the one or more colour change pads by detecting two opposite edges 539A, 539B of each of the colour change pads, as conceptually presented in FIG. 5. The server scans the test area from a first side 537A to a second side 537B opposite the first side. The server identifies discontinuities in brightness as it scans across the test area. Discontinuities in brightness relate to a change in colour from the colour of the background region 545 of the test area (i.e. the colour of the portion 545 of test area that surrounds the colour change pads) to the colour of a colour change pad. In an example, the background colour of the test area is white, and the colour change pads are non-white.

In an example as presented in the conceptual diagram of FIG. 5, the server scans from the topmost side 537A of the test area 537 in a direction toward the bottommost side 537B of the test area 537. In another example, the server may scan from a leftmost edge of the test area to a rightmost edge.

When scanning in this direction the server identifies a first brightness discontinuity when passing from the background region 545 of the test area 537 onto a first colour change pad 209-1. This brightness discontinuity is indicative of the first edge 539A-1 of the first colour change pad 209-1. The server stores coordinates of this first edge 539A-1 using a coordinate system for the image.

The server continues scanning toward the bottommost side of the of the test area 537 and identifies a second brightness discontinuity when passing from the first colour change pad 209-1 to the background region 545 of the test area 537. This brightness discontinuity is indicative of the second edge 539B-1 of the first colour change pad 209-1. The server stores coordinates of this second edge using the coordinate system.

From the first edge 539A-1 and the second edge 539B-1, the server determines the location of the first colour change pad as being the region contained between the two edges 539A-1 and 539B-1. That is, the coordinates of the first colour change pad 209-1 are the coordinates contained between the coordinates of the first edge 539A-1 and the second edge 539B-1.

The server repeats this process when scanning toward the bottommost side of the test area in order to identify the location of the second colour change pad 209-2 using coordinates of the first edge 539A-2 and second edge 539B-2 of the second colour change pad 209-2, the third colour change pad 209-3 using coordinates of the first edge 539A-3 and second edge 539B-3 of the third colour change pad 209-3, the fourth colour change pad 209-4 using coordinates of the first edge 539A-4 and second edge 539B-4 of the fourth colour change pad 209-4, and the fifth colour change pad 209-5 using coordinates of the first edge 539A-5 and second edge 539B-5 of the fifth colour change pad 209-5. The skilled person will readily understand that this is not limited to five colour change pads, and that the process can be carried out in a similar manner for equipment comprising one or more colour change pads.

Advantageously, step 410B allows for the location of the colour change pads 209 to be accurately determined. In particular, the location of colour change pads 209 can be determined without the need to use anchor points presented on the card 200. As such, anchor points are not required on the card 200 thereby saving space on the card 200 and allowing for a reduced size of card 200.

If the edge detection is successful in detecting two opposite edges 539A, 539B of each colour change pad, the process continues to step 414B.

If the colour change pad locating fails, for example if one or more of the expected edges cannot be detected, the process proceeds to step 412B and the server instructs the application to present the user with a notification, by the display of the electronic device, indicating that the processing has failed or cannot be carried out. In an example, the server can determine how many edges should be expected based upon information accessible using the machine readable label 211.

Once the location(s) of the colour change pad(s) 209 have been specifically determined, an area or sub-region of each colour change pad 209 is selected to provide a suitably representative colour sample. At step 414B, the server uses the location of each of the colour change pads, as determined in step 410B, to sample colour data of a testing sub-region 541 within each test region (i.e. each colour change pad), as conceptually presented in FIG. 5. The sampling comprises sampling the colour of the region. The sub-region 541 is a square (or any other suitable shape) that is smaller in size than the test region 209 in the image data as determined by the edge locating in step 410B, and contained within the test region. For each colour change pad 209, the server arranges the testing sub-region 541 such that it is in an area between the edges 543A and 543B of the colour change pad 209. That is, the testing sub-region is within the determined coordinate area of the colour change pad 209. The colour sampling processing is repeated for each of the colour change pads.

If the colour sampling at step 414B is successful, the process continues to step 416A. If the colour sampling fails, the process proceeds to step 412B and the server instructs the application to present the user with a notification, by the display of the electronic device, indicating that the processing has failed or cannot be carried out.

At step 416B shadow detection is carried out. The shadow detection is repeated for each of the colour change pads. The shadow detection is used to remove possible interference in the colour detection of a strong locally applied light source that may cause the electronic device to cast a shadow across the card 200. The shadow detection uses background sub-regions adjacent to the colour change pad(s) (the background sub-regions, or known white regions, are described in more detail subsequently). A large discrepancy between light quality readings across multiple background sub-regions is indicative of a shadow. If shadowing is detected, the server instructs the application to alert the user, and provide guidance to change the location in which the image capture for analysis is taking place; this suppresses the reporting of results from analysis when a shadow is present in the image data.

At step 418B chromatic adaption is carried out to account for varying brightness in the image data. The chromatic adaption is repeated for each of the colour change pads. The chromatic adaption uses brightness measurements at the background sub-regions adjacent to the colour change pad(s). A discrepancy in brightness across multiple background sub-regions is indicative of varying brightness in the image data. If a brightness discrepancy is detected, the server adapts the brightness across the image based upon the brightnesses at the background sub-regions.

At step 420B, the server performs a colour calibration of each sampled colour to account for effects in the sampled colours resulting from lighting conditions when the image data was captured.

Colour calibration or adjustment is achieved by taking a colour sample of background sub-regions either side of the colour change pad 209 (such as known "white" regions) in order to provide light quality readings, including colour temperature, or light temperature, and intensity. The skilled person will readily understand that, in the present context, the terms calibration and adjustment are interchangeable. These light readings are then used to adjust the colour sampled for ambient lighting conditions. In more detail, the colour calibration is carried out on colour data of the first testing sub-region 541-1 of the first colour change pad 209-1 as sampled at step 414B. The server determines colour calibration data, such as colour or light temperatures, of first background sub-regions 543A-1, 543B-1 separate from, arranged either side of, and corresponding to, the first colour change pad 209-1 as presented in the conceptual diagram in FIG. 5. A colour or light temperature is a characteristic of a light source illuminating an object and can range from a cool temperature or 'bluish' colour to a warm temperature or 'yellowish' colour; colour or light temperature relates to the temperature at which a black body would emit radiation of the same colour. The terms colour temperature and light temperature are used interchangeably. Whilst FIG. 5 is presented according to the embodiment of FIG. 2, it will be readily understood that the same process applies to the embodiment of FIG. 1. One first background sub-region 543A-1 is arranged proximal to a first side of the first colour change pad 209-1 and the other first background sub-region 543B-1 is arranged proximal to a second side of the first colour change pad 209-1; the first side of the colour change pad 209-1 being an opposite side to the second of the colour change pad 209-1.

The background sub-regions 543A-1, 543B-1 are sub-regions of the background region 545 of the card, surrounding or bordering the colour change pads 209. The background sub-regions 543A-1, 543B-1 are disposed at predetermined displacements either side of the first colour change pad 209-1 in order to sample the colour temperature(s) of the background region 545 either side of the first colour change pad 209-1. The colour change pads 209 are of a known size, and the card 200 is of a known size, for example as determined from the machine readable label 211, and due to the alignment of the card 200 in the window of the display when the image is captured, and these known sizes, as well as the determined location of the colour change pads, the server can utilise this information to arrange the background sub-regions such that they are on the background region 545 of the card 200 in the image, rather than on the colour change pad(s) 209 or away from the card 200 itself.

The background sub-regions 543A-1, 543B-1 are arranged such that a straight line extending between the two background sub-regions 543A-1, 543B-1 passes through the first testing sub-region 541-1. In an example, each of the background sub-regions 543A-1, 543B-1 is equal in size to the first testing sub-region 541-1.

The background region is substantially white in colour. The server determines a first colour temperature of the first background sub-region 543A-1 on a first side of the first colour change pad 209-1 and a second colour temperature of the first background sub-region 543B-1 on a second side of the colour change pad 209-1 opposite the first side. The server then determines a colour temperature gradient along the line using the first colour temperature and the second colour temperature as end points.

Advantageously the colour temperature of the white background region can be used to determine calibration data resulting from ambient lighting illuminating the card. This allows for the colour data to be calibrated thereby removing effects in the colour data resulting from the ambient lighting. Moreover, this removes the need to use separate colour reference charts either on the card, or captured with the image data of the card as the white background can instead be used.

Using the colour temperature gradient, and a coordinate system applied to the image, the server calculates a colour temperature at a position along the line corresponding to the position of the first testing sub-region 541-1. The server then calibrates the colour data of the first testing sub-region 541-1 using the calculated colour temperature for the first testing sub-region 541-1 to account for any distortions to colour in the image that result from the ambient lighting irradiating the card 200 when the image is captured. In an example, the server calibrates the colour data by subtracting the calculated captured light temperature from the colour data. The colour data can include descriptors, RGB values, LAB values, CMYK values amongst others.

The server then repeats the process for each of the colour change pads. That is, the server calibrates sampled colour data of a second testing sub-region 541-2 of the second colour change pad 209-2 using the second background sub-regions 543A-2 and 543B-2, a third testing sub-region 541-3 of the third colour change pad 209-3 using the third background sub-regions 543A-3 and 543B-3, a fourth testing sub-region 541-4 of the fourth colour change pad 209-4 using the fourth background sub-regions 543A-4 and 543B-4, and a fifth testing sub-region 541-5 of the fifth colour change pad 209-5 using the fifth background sub-regions 543A-5 and 543B-5. The skilled person will readily understand that this is not limited to five colour change pads, and that the process can be carried out in a similar manner for equipment comprising one or more colour change pads.

Advantageously, this colour calibration allows for the colour change pads to be analysed under varying lighting conditions such as sunlight and artificial lighting. Moreover, the gradient allows for differing lighting illuminating either side of the card to be accounted for, i.e. if two different light sources are illuminating the card from different positions. The colour calibration may utilise a camera flash associated with the camera of the electronic device when the image is captured such that the flash contributes to the ambient lighting thereby improving the image data recorded, and the sampled colour data.

In a further colour calibration technique, the colour calibration may utilise a camera flash associated with the camera of the electronic device when the image is captured. The camera flash of an electronic device such as a smartphone has a known predetermined colour temperature. Due to the proximity of the camera flash to the card 200 when the image is captured, the colour temperature of the camera flash dominates any ambient lighting effects. As such, the sampled colour data of the testing sub-regions 541-1, 541-2, 541-3, 541-4 and 541-5 can be calibrated by the server using the known colour temperature of the camera flash. The colour temperature of the flash can be included in metadata transmitted to the server, by the electronic device, when the image data is transmitted. In an example, the server calibrates the colour data by subtracting the colour temperature of the camera flash from the colour data. The server may utilise either or both of the colour calibration techniques.

In an alternative colour calibration technique, the server may use a colour reference chart 213 present on the card. Sampled colours of the colour reference chart 213 extracted from the image data can be compared to corresponding known predetermined colours by the server. The known predetermined colours may be accessed using information derivable from the machine readable label 211; for example, the known predetermined colours may be identified by the server using information derived from the machine readable label 211 and accessed by the server from storage accessible to the server using such information. The difference between the extracted colour from the image data of the colour reference chart 213 and the corresponding known predetermined colours can be used to calibrate the colour data of the testing sub-regions 541.

The server can utilise any individual one of the colour calibration techniques, or a combination of two or more of the colour calibration techniques.

Following the colour calibration, the process proceeds to step 422B.

At step 422B, the calibrated colour is compared to predetermined reference standards or reference colours in storage accessible by the server. A delta E value is determined between each reference colour and the adjusted sampled colour. The reference colour with the smallest delta E value is selected as the closest matching reference colour and is used to determine the reported value. In more detail, the server compares the calibrated colour data of the calibrated sampled colours to predetermined reference colours for each colour change pad prior to the application of urine. In an example, the predetermined reference colours are stored at the server. The predetermined colours can be identified based upon the determination of the type of test using the machine readable label 211, as described with reference to step 404. A delta E calculation is performed by the server to determine the difference between the predetermined reference colours and the calibrated sampled colour. For each colour change pad, the reference colour with the smallest delta E value, compared to the calibrated sampled colour, is determined. That is, the closest matching predetermined reference colour to the adjusted sampled colour is calculated by being the predetermined reference colour with the smallest delta E value when compared to the adjusted sampled colour. When a condition (such as a urinary tract infection, diabetes, or glucose levels for diabetic screening or monitoring, or a metabolic disorder, kidney disease, liver disease, a dietary disorder, or a pregnancy term complication, amongst others) is being tested for using a colour change pad, an indicator of the condition in the urine will cause the colour change pad to change colour when the urine interacts with reagents in the colour change pad. If the measured analyte is present in the urine the colour to which the colour change pad changes will correspond to a reference colour which is an indicator of the presence of the condition. That is, when the closest matching predetermined reference colour to the calibrated sample colour corresponds to a predetermined reference colour representing indicators of the condition being present in the bodily fluid sample, it is determined that the indicators of the condition are present in the bodily fluid sample, i.e. the condition is present in the bodily system of the provider of the bodily fluid. Likewise, when the closest matching predetermined reference colour to the calibrated sample colour does not correspond to a predetermined reference colour representing indicators of the condition being present in the bodily fluid sample, it is determined that the indicators of the condition are not present in the bodily fluid sample, i.e. the condition is not present in the bodily system of the provider of the bodily fluid.

Following the delta E calculation, the process continues to step 424B.

At step 424B, if it is determined that the indicator(s) of the condition being tested for are present in the urine sample, the server instructs the application to output, on the display of the electronic device, to the user, a result indicating that the condition is present in the bodily system of the user. Advantageously, this allows for the user of the equipment to have immediate access to the results. Likewise, if it is determined that the indicator(s) of the condition being tested for are not present in the urine sample the server instructs the application to output a result, on the display of the electronic device, to the user, indicating that the condition is not present in the bodily system of the user.

In the case of either the application carrying out the processing described with reference to FIG. 4, or the server carrying out the processing, in some examples, only one colour change pad is required to identify that the condition is present in the bodily system of the user. That is, only one indicator need be detected in the applied urine. In other examples, in which multiple indicators are required in the applied urine to identify that the condition is present in the bodily system of the user, multiple colour change pads can be analysed using the method described with reference to FIG. 4, with each colour change pad sensitive to a different indicator. That is, the result may be determined based upon one colour change pad with which one indicator in the urine has interacted, or the result may be determined based upon a plurality of colour change pads with which a plurality of indicators in the urine have respectively interacted.

In the aforementioned process, progression of the process to step 412A or 412B, as a result of a failure to complete one of steps 410A, 414A, 416A or 410B, 414B, 416B respectively, the application may prompt the user to capture new image data of the card so that the process may begin again at step 402.

Figure 6:
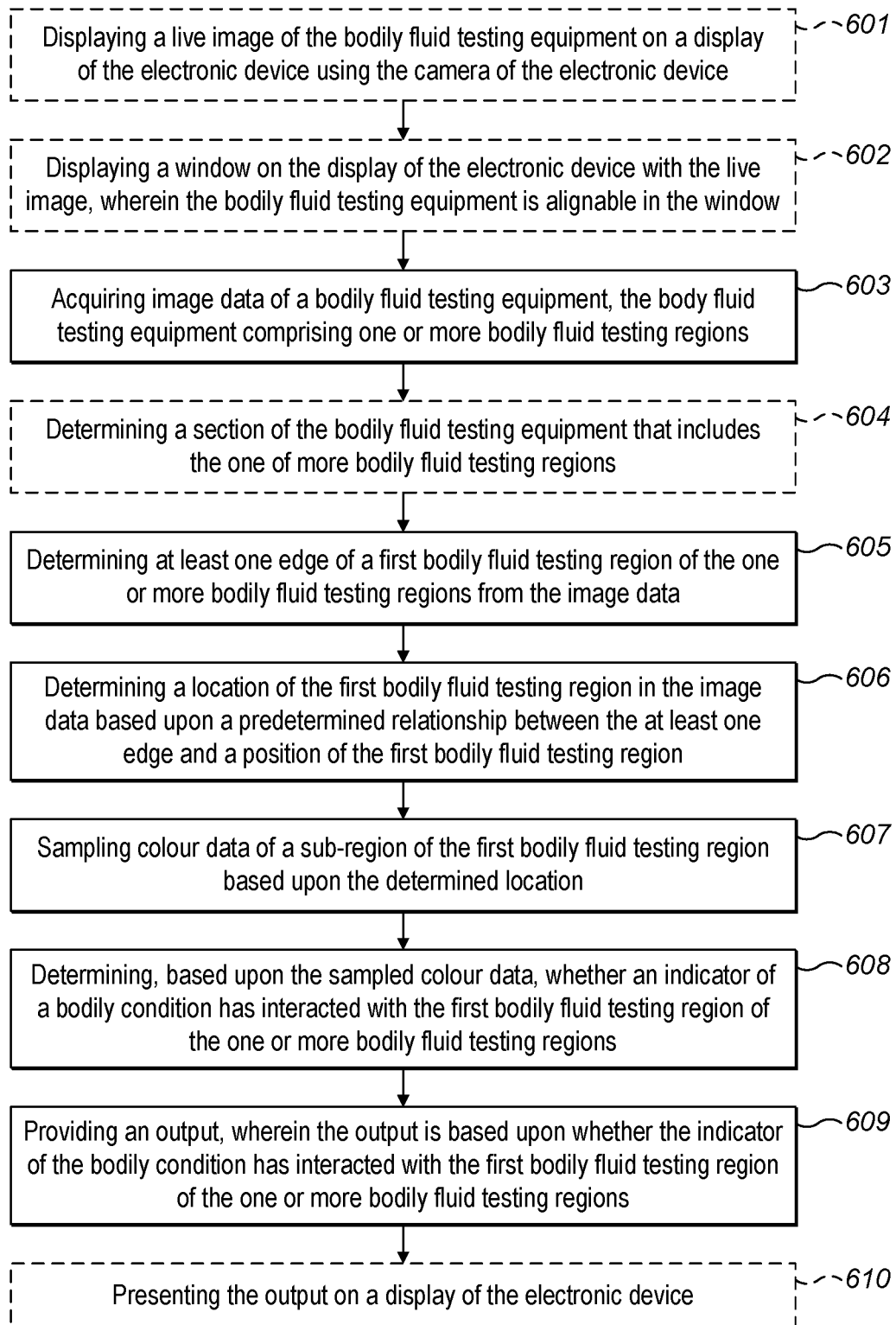
FIG. 6 is a flow diagram of steps involved in test location detection.

FIG. 6 shows a flow diagram of a method for determining an indicator of a bodily condition in an image of a bodily fluid testing equipment captured by an electronic device compatible with that particularly described with reference to steps 410A and 410B.

Optionally, at step 601, a live image of the bodily fluid testing equipment, or card, is displayed on a display of the electronic device using the camera of the electronic device.

Optionally, at step 602, a window is displayed on the display of the electronic device with the live image, wherein the bodily fluid testing equipment is alignable in the window.

In an example, steps 601 and 602 occur simultaneously.

The user can align the bodily fluid testing equipment in the live image within the window presented on the display of the electronic device. In an example, the window is of a similar shape to that of the bodily fluid testing equipment such that the edges of the bodily fluid testing equipment are alignable with edges of the window. A sub-window can also be presented within the window; the sub-window is arranged such that the user is prompted to align the machine readable label or QR code within the sub-window. This can improve the alignment of the card for image capture.

At step 603 image data of the bodily fluid testing equipment is acquired by the electronic device, the bodily fluid testing equipment comprising one or more bodily fluid testing regions, or colour change pads. In an example, acquiring the image data comprises capturing the image data by a camera on the electronic device, preferably in the form of a photograph. In an example, the electronic device is a smartphone. In an example, the one or more bodily fluid testing regions are colour change pads that change colour in response to interaction with indicators in bodily fluid. In an example, the bodily fluid is urine.

In an example, the electronic device automatically captures the image data of the bodily fluid testing equipment in response to identifying that the bodily fluid testing equipment is aligned in the window and/or the machine readable label is aligned within the sub-window. If the machine readable label is obscured, due to a finger or thumb of the user covering (or partially covering) the label for example, the application may not capture the image until the machine readable label is no longer obscured (i.e. the user has moved their finger or thumb away from the machine readable label).

Optionally, step 604, a section of the bodily fluid testing equipment is determined that includes the one or more bodily fluid testing regions. The determining of the section of the bodily fluid testing equipment that includes the one or more bodily fluid testing regions can be based upon a predetermined relationship. The predetermined relationship can be between the window in which the bodily fluid testing equipment is alignable and the section. Alternatively or additionally, the predetermined relationship can be between a determined location of the machine readable label (the determined location based upon the alignment of the machine readable label and the sub-window) and the section.

At step 605, at least one edge of a first bodily fluid testing region of the one or more bodily fluid testing regions is determined from the image data. In an example, determining the at least one edge comprises determining a discontinuity in brightness between the testing region and a surrounding region indicative of the interface between the testing region and the surrounding region. In an example, the determining the at least one edge further comprises scanning the determined section of the bodily fluid testing equipment.

In an example the determining of the at least one edge of the first bodily fluid testing region comprises determining two opposite edges of the first bodily fluid testing region, and the method further comprises determining the location of the first bodily fluid testing region as being confined between the two edges. In another example, the determining the at least one edge of the first bodily fluid testing region comprises determining all four edges of a square or rectangular shaped bodily fluid testing region; in such an example, the method can further comprise determining the location of the bodily fluid testing region as being confined between the four edges.

At step 606 a location of the first bodily fluid testing region is determined in the image data based upon a predetermined relationship between the at least one edge and a position of the first bodily fluid testing region.

At step 607, colour data of a sub-region of the first bodily fluid testing region is sampled based upon the determined location.

At step 608, it is determined, based upon the sampled colour data, whether an indicator of a bodily condition has interacted with the first bodily testing region of the one or more bodily fluid testing regions.

At step 609, an output is provided wherein the output is based upon whether the indicator of the bodily condition has interacted with the first bodily fluid testing region of the one or more bodily fluid testing regions.

In an example, steps 601 to 609 are all performed at the electronic device.

In another example, the image data is acquired at the electronic device (for example encompassing steps 601 to 603) and the electronic device transmits the image data to a server; steps 604 to 609 are then performed at the server.

In an example, the method then further comprises transmitting, by the server to the electronic device, instructions that instruct the electronic device to present a determined output, based upon the sampled colour data, on a display of the electronic device.

Optionally, at step 610, the output is presented on the display of the electronic device. For example, the application displays the result as a textual or pictorial message, or a combination thereof. In an example step 610 occurs as a result of steps 601 to 609 being performed at the electronic device. In another example, step 610 occurs as a result of steps 604 to 609 being performed at the server.

Figure 7:
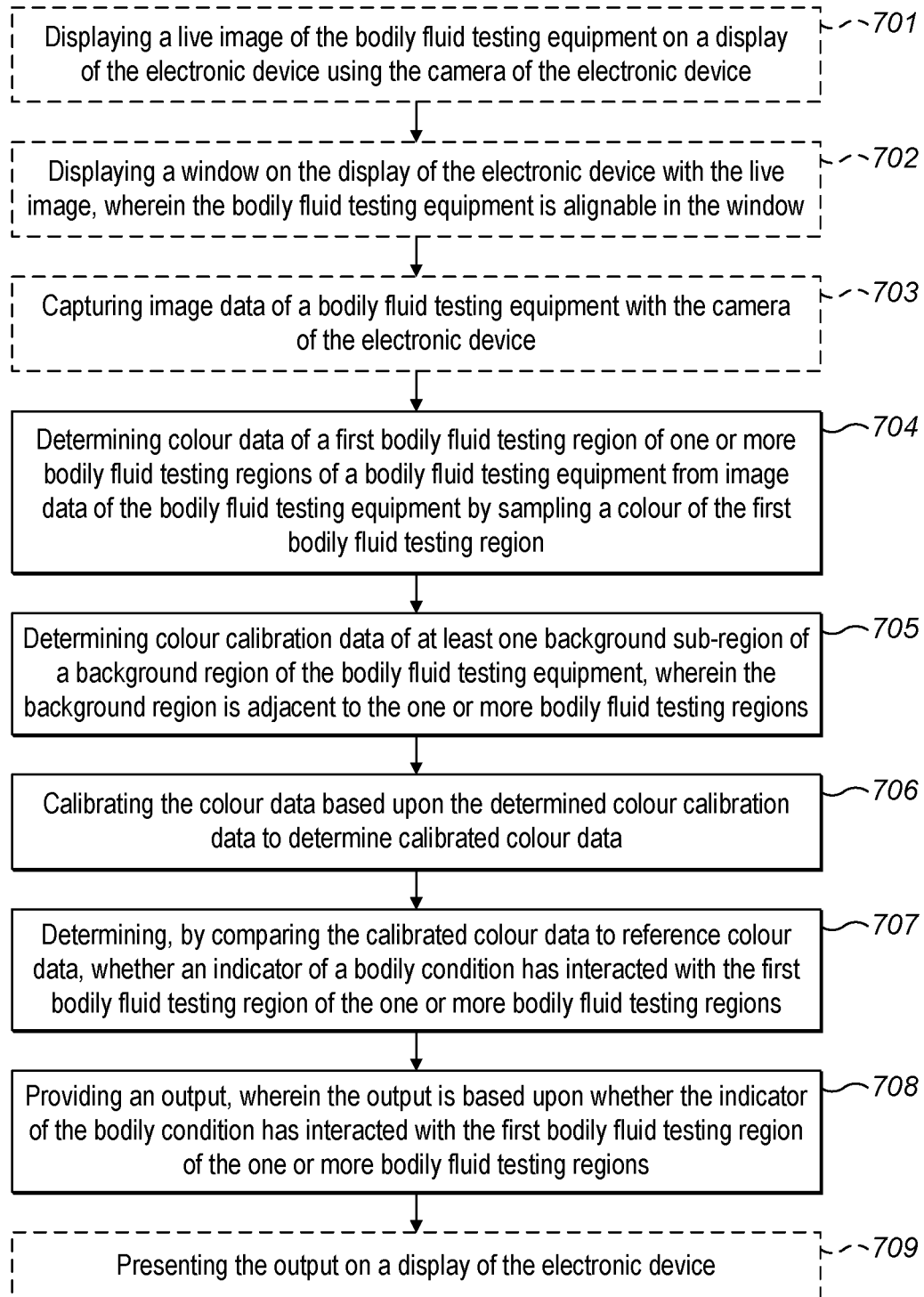
FIG. 7 is a flow diagram of steps involved in colour calibration.

FIG. 7 shows a flow chart of method for determining an indication of a bodily condition in image data of bodily fluid testing equipment, the image data captured by an electronic device compatible with that described particularly with reference to steps 420A and 420B.

Optionally, at step 701 a live image of the bodily fluid testing equipment is displayed on a display of an electronic device using the camera of the electronic device.

Optionally, at step 702 a window is displayed on the display of the electronic device with the live image, wherein the bodily fluid testing equipment is alignable in the window.

In an example, steps 701 and 702 occur simultaneously.

The user can align the bodily fluid testing equipment in the live image within the window presented on the display of the electronic device. In an example, the window is of a similar shape to that of the bodily fluid testing equipment such that the edges of the bodily fluid testing equipment are alignable with edges of the window. A sub-window can also be presented within the window; the sub-window is arranged such that the user is prompted to align the machine readable label or QR code within the sub-window. This can improve the alignment of the card for image capture.

Optionally, at step 703 image data of the bodily fluid testing equipment is captured with the camera of the electronic device. In an example, the electronic device automatically captures the image data of the bodily fluid testing equipment in response to identifying that the bodily fluid testing equipment is aligned in the window and/or machine readable label is aligned within the sub-window. If the machine readable label is obscured, due to a finger or thumb of the user covering (or partially covering) the label for example, the application may not capture the image until the machine readable label is no longer obscured (i.e. the user has moved their finger or thumb away from the machine readable label).

At step 704 colour data of a first bodily fluid testing region of one or more bodily fluid testing regions of a bodily fluid testing equipment is determined from image data of the bodily fluid testing equipment by sampling a colour of the first bodily fluid testing region.

In an example, the image data is captured using the camera of an electronic device such as a smartphone. In an example the bodily fluid testing region comprises a colour change pad that changes colour in response to interaction with an indicator in the bodily fluid. In an example the bodily fluid is urine.

In an example, the colour data is determined based upon sampling a testing sub-region of the first bodily fluid testing region, the testing sub-region at a location within the bodily fluid testing region.

At step 705 a colour calibration data of at least one background sub-region of a background region of the bodily fluid testing equipment is determined, wherein the background region is adjacent to the one or more bodily fluid testing regions.

In an example, the background region is a border surrounding the bodily fluid testing region on the bodily fluid testing equipment. In an example, the background region is substantially white in colour. In an example, the colour calibration data is a colour temperature of the at least one background sub-region of the background region. A colour temperature is a characteristic of a light source illuminating an object and can range from a cool temperature or 'bluish' colour to a warm temperature or 'yellowish' colour; colour temperature relates to the temperature at which a black body would emit radiation of the same colour.

In an example, if there is more than one background sub-region, the calibration of the colour data is based upon the determined colour calibration data of each of the background sub-regions. In an example, the at least one background sub-region is determined based upon a predetermined displacement from the location of the testing sub-region. In an example, the testing sub-region, and the bodily fluid testing equipment are of known sizes, for example as determined from a machine readable label presented on the bodily fluid testing equipment. Due to alignment of the bodily fluid testing equipment in a window presented on a display of the electronic device when the image data is captured, and these known sizes, and a determined location of the testing sub-region, this information can be utilised to arrange the background sub-region(s) such that they are on the background region of the bodily fluid testing equipment in the image data, rather than on the testing sub-region or away from the bodily fluid testing equipment itself. In an example, the at least one background sub-region comprises two background sub-regions.

In an example, a first background sub-region of the two background sub-regions is displaced away from the bodily fluid testing region on a first side of the bodily fluid testing region, and a second background sub-region of the two background sub-regions is displaced away from a second side of the bodily fluid testing region, wherein the second side of the bodily fluid testing region is an opposing side of the bodily fluid testing region to the first side of the bodily fluid testing region.

At step 706 the colour data is calibrated based upon the determined colour calibration data to determine a calibrated colour data.

In an example, each of the testing sub-region, the first background sub-region and the second background sub-region are arranged along a straight line between the first background sub-region and the second background sub-region. In an example, first colour calibration data (such as a first colour temperature) of the first background sub-region is determined, second colour calibration data (such as a second colour temperature) of the second background sub-region is determined, and a colour calibration gradient (such as a colour temperature gradient) along the line joining the testing sub-region, the first background sub-region and the second background sub-region is determined based upon the first colour calibration data and the second colour calibration data. Calculated colour calibration data (such as a calculated colour temperature) is calculated based upon the colour calibration gradient, at a point along the line, wherein the point corresponds to the location of the testing sub-region. Calibrating the colour data based upon the determined colour calibration data comprises calibrating the colour data at the testing sub-region based upon the calculated colour calibration data to determine the calibrated colour data.

In an example, the image data is captured with a camera of an electronic device, using a camera flash associated with the camera, and the calibrating of the colour data further comprises using the colour calibration data of the flash.

At step 707 it is determined, by comparing the calibrated colour data to reference colour data, whether an indicator of a bodily condition has interacted with the first bodily testing region of the one or more bodily fluid testing regions.

At step 708, an output is provided, wherein the output is based upon whether the indicator of the bodily condition has interacted with the first bodily fluid testing region of the one or more bodily fluid testing regions.

Optionally, at step 709, the output is presented on a display of an electronic device, such as a smartphone. For example, the application displays the result as a textual or pictorial message, or a combination thereof.

In an example steps 701 to 709 are performed at an electronic device, and the image data is captured with a camera of the electronic device, such as a smartphone.

In another example, the steps 701 to 703 are performed at an electronic device, and the steps 704 to 708 are performed at a server in response to the electronic device transmitting the image data of the bodily fluid testing equipment to the server. In an example the electronic device is a smartphone. In an example the server utilises a Python application programming interface. In an example, providing the output at step 708 comprises the server transmitting the output to the electronic device and step 709 occurs at the electronic device.

Figure 8:
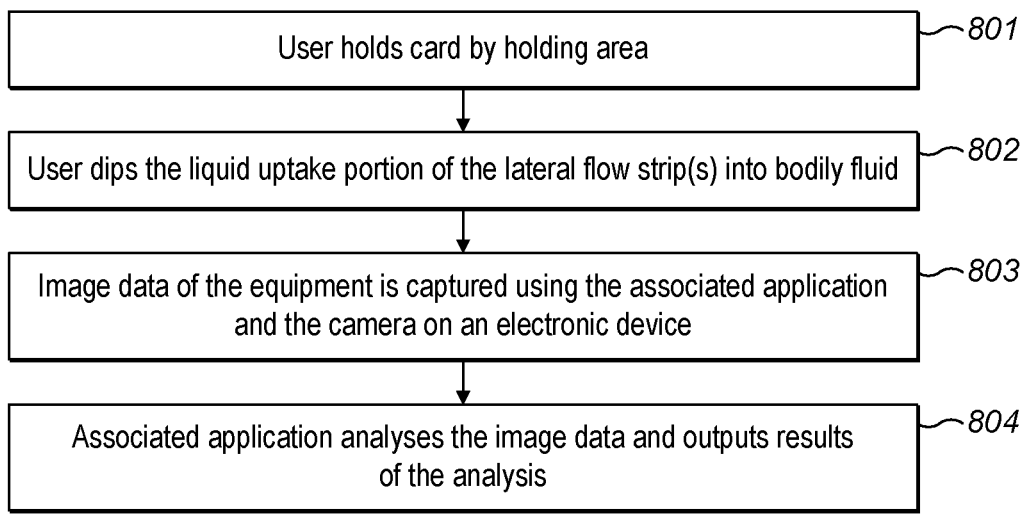
FIG. 8 is a flow diagram of a method by which a user can use an application-analysable lateral flow bodily fluid testing equipment.

FIG. 8 depicts a flow diagram of a method by which a user of the application-analysable lateral flow bodily fluid testing equipment 300, or card 300, as described with reference to FIG. 3, uses the equipment and associated application.

At step 801, the user of the card 300 holds the card 300 by the holding area 301. At step 802 the user dips the liquid uptake portion 351 of the lateral flow strip(s) 309 into a bodily fluid sample such as urine. At step 803 the user image data of the card 300 is captured using the associated application and camera on an electronic device such as a smartphone. In some examples, the user may be need to wait for a time period to elapse to allow for the bodily fluid to wick along the lateral flow strip and bind to the immobilised antibodies before the image data can be captured. At step

804 the associated application analyses the image data and outputs the results of the analysis.

Figure 9:
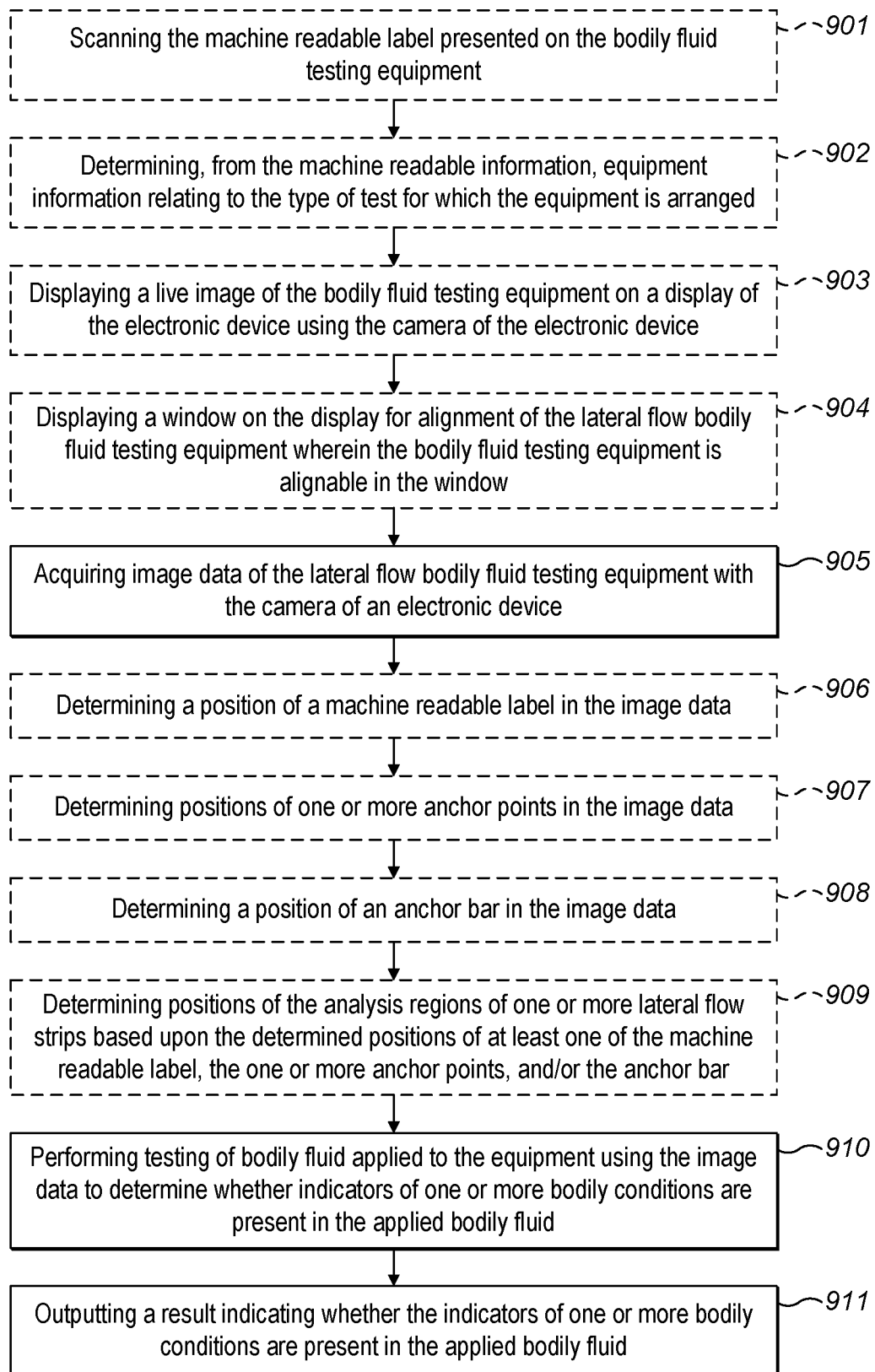
FIG. 9 is a flow diagram of processing and analysis steps performed at an application associated with an application-analysable lateral flow bodily fluid testing equipment.

FIG. 9 depicts a flow diagram of processing steps performed at the application executed on an electronic device such as a smartphone during the steps 803 and 804 described with reference to FIG. 8. The electronic device can be a smartphone; however, the skilled person will readily understand that any other suitable electronic device may be used, such as a tablet computer.

The application uses the camera of the electronic device to present a live image of the card on the display of the electronic device when the card is position in front of the camera. Optionally, at step 901, the electronic device scans the machine readable information 311 presented on the card 300. In an example, the application uses the camera of the electronic device to scan the machine readable information 311.

Optionally, at step 902, the application determines, from the machine readable information, equipment information relating to the type of test for which the equipment 300, or card 300, is arranged; for example pregnancy testing, drug misuse, and testing for hormones or antibodies in conditions where these provide diagnostic support such as ovulation health, prostate specific antigen levels, malaria, infertility, sexually transmitted infections, and diabetes HbA1c, amongst others. In an example, the application uses the machine readable information to access equipment information corresponding to the machine readable information from storage accessible by the application. The equipment information can include a size or aspect ratio of the card, the type of indicators the lateral flow strips are sensitive to, the number of lateral flow strips, the position of the lateral flow strips in relation to the one or more anchor points, and the size of the card amongst other parameters.

Optionally, at step 903, the application displays a live image of the bodily fluid testing equipment on a display of the electronic device using the camera of the electronic device.

Optionally, at step 904, the application displays a window, or box, on the display of the electronic device for alignment of the card 300. In an example, the window overlays the live feed from the camera. The window is of a similar shape to that of the body 305 of the card 300 so as to guide the user to align the card 300 for image capture. A sub-window can be presented within the window; the sub-window can be arranged such that the user is prompted to align the machine readable label or QR code within the sub-window. This can improve the alignment of the card for image capture. In an example, steps 903 and 904 occur simultaneously.

At step 905, the application acquires image data of the card 300. In an example, acquiring the image data comprises capturing the image data using a camera of the electronic device. In an example, the application automatically captures the image data in response to identifying that the card 300 is sufficiently aligned in the window and/or the machine readable information 311 is aligned within the sub-window. If the machine readable information 311 is obscured, due to a finger or thumb of the user covering (or partially covering) the machine readable information for example, the application may not capture the image until the machine readable information 311 is no longer obscured (i.e. the user has moved their finger or thumb away from the machine readable label). In another example, the user instructs the application to use the camera of the electronic device to capture the image data by, for example, pressing a 'capture image' button.

In an alternative, in place of steps 901-905, the application presents the user with an interface allowing the user to import a previously captured photograph of the card 300. In an example, the application then scans the machine readable label.

Optionally, at step 906, the application determines the position of the machine readable label/information (or QR code) 311 in the image data. This is aided by the alignment of the machine readable label 311 in the sub-window.

Optionally, at step 907, the application determines positions of the one or more anchor points 349 in the image data. In an example, the one or more anchor points comprise indicia presented on the first surface of the body portion. In an example, the one or more anchor points comprise a plurality of anchor points positioned proximal to the analysis region, and wherein one of the anchor is distinct from the other anchor points. The application can use the distinct anchor point to identify the orientation of the application-analysable bodily fluid testing equipment in the image data.

Optionally, at step 908, the application determines a position of the anchor bar 357 in the image data. In an example, the anchor bar is arranged on the first surface of the body portion at a substantially central position.

Optionally, at step 909, the application determines positions of the analysis regions of the one or more lateral flow strips based upon the determined positions of at least one of the machine readable label 311, the one or more anchor points 349 and/or the anchor bar 357. In an example, the application determines the positions of the analysis region 355 of the lateral flow strips 309 by utilising information contained in the equipment information accessed at step 902. A predetermined relationship (or displacement) between the at least one of the machine readable label 311, the one or more anchor points 349 and the anchor bar 357 with respect to the analysis region 355 is known from the equipment information for the specific type of card. Due to the alignment of the card 300 in the window of the display when the image is captured, and using these known displacements, the application can determine the location of the analysis region 355 from the machine readable label 311, the one or more anchor points 349 and the anchor bar 357. The combination of these points allows the application to accurately determine the position(s) of the lateral flow strip(s) 309.

At step 910, the application performs testing of bodily fluid applied to the equipment using the image data to determine whether indicators of one or more bodily conditions are present in the applied bodily fluid. Optionally, the testing comprises the application determining whether one or more lines are present in the analysis regions of the one or more lateral flow strips. In an example, the application determines whether a line is present by projecting a virtual line along the length of the lateral flow strip. Colour density is measured along the line. In an example, a white colour has no density and a black has 100% density. Points where the density increases correspond to a line or band being present. The intensity of the test line or band is directly proportional (up to a saturation point) to the concentration of analyte of interest present in the bodily fluid and thus can quantify the result. The intensity of the test line can be determined by comparing the test line against the control line, which has a corresponding fixed value. Optionally, the testing further comprises the determining the intensity of the line.

At step 911, the application outputs a result indicating whether the indicators of one or more bodily conditions are present in the applied bodily fluid. Optionally, the outputting the result comprises outputting a positive result that indicators are present in the bodily fluid for each lateral flow strip for which a line appears in the respective analysis region, and outputting a negative result that indicators are not present in the bodily fluid for each lateral flow strip for which a line does not appear in the respective analysis region. In an example, the application outputs the result on the display of the electronic device. For example, the application displays the result as a textual or pictorial message, or a combination thereof.

Advantageously, this allows for lateral flow testing to be achieved in an efficient manner without the reliance on specialist lateral flow testing devices.

Figure 10:
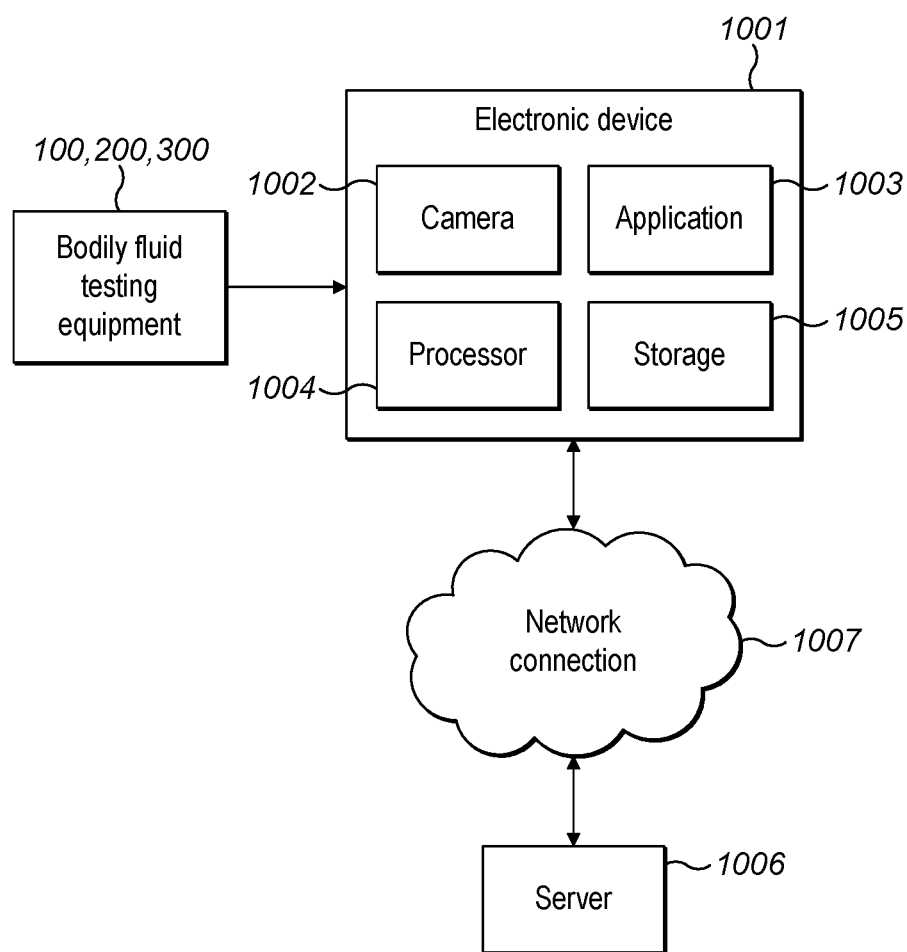
FIG. 10 is a block diagram of hardware entities in bodily fluid testing systems according to embodiments of the disclosure.

FIG. 10 presents a block diagram of the hardware entities in the bodily fluid testing systems of the present disclosure. The electronic device 1001, such as a smartphone, comprises a camera 1002. The electronic device 1001 has an application 1003 stored thereon arranged to perform methods previously described in the present description. The electronic device 1001 further has a processor 1004 arranged to execute the application. The electronic device 1001 further includes storage 1005; the storage 1005 storing code executable by the processor 1004 to execute the application 1003 as well as parameters relating to the application 1003. The camera 1002 is arranged to capture image data, or photograph(s), of the bodily fluid testing equipment or card 100, 200, 300 as previously described in the present description. In some examples the application 1003 carries out the previously described analysis methods locally. In other examples, the previously described analysis methods are at least partially carried out at a server 1006. In such a case, the electronic device 1001 is connected to the server 1006 by a network connection 1007, for example an internet connection or a 4G connection (amongst other suitable network connection means). The electronic device 1001 and the server 1006 exchange communications using the network connection 1007.

It will be readily understood to the skilled person that the preceding embodiments are not limiting; features of each embodiment may be incorporated into the other embodiments as appropriate.

The processing steps described herein carried out by the electronic device may be stored in a non-transitory computer-readable medium, or storage, associated with the electronic device. A computer-readable medium can include non-volatile media and volatile media. Volatile media can include semiconductor memories and dynamic memories, amongst others. Non-volatile media can include optical disks and magnetic disks, amongst others.

The invention claimed is:

1. A lateral flow bodily fluid testing system, the system comprising:
an application-analysable bodily fluid testing equipment having a body portion, a QR code on the body portion, and one or more lateral flow testing strips combined with a first surface of the body portion, the one or more lateral flow testing strips having a predetermined displacement from the QR code, the one or more lateral flow testing strips being sensitive to indicators of bodily conditions in bodily fluid, and wherein the one or more lateral flow testing strips each comprise at least one respective fluid uptake region connected to at least one respective analysis region; and
an electronic device comprising a camera and one or more processors, wherein the one or more processors are configured to:
acquire image data of the bodily fluid testing equipment with the camera of the electronic device;
determine a position of the QR code in the image data;
determine a position of the at least one respective analysis region of the one or more lateral flow testing strips using the predetermined displacement based upon the determined position of the QR code;
perform testing of bodily fluid applied to the bodily fluid testing equipment, using the image data at the determined position of the at least one respective analysis region, to determine whether indicators of one or more bodily conditions are present in the applied bodily fluid; and
output a result indicating whether the indicators of one or more bodily conditions are present in the applied bodily fluid.

2. The system of claim 1, wherein the body portion comprises a holding area, the holding area holdable by a user both when applying bodily fluid to the one or more lateral flow testing strips and capturing image data of the bodily fluid testing equipment.

3. The system of claim 2, wherein the holding area comprises indicia indicating to a user of the bodily fluid testing equipment to hold the bodily fluid testing equipment by the holding area.

4. The system of claim 1, wherein the body portion is substantially planar.

5. The system of claim 1, wherein at least a portion of the at least one respective fluid uptake region of each of the one or more lateral flow testing strips extends over an edge of the first surface of the body portion.

6. The system of claim 1, wherein the one or more lateral flow testing strips comprises a plurality of lateral flow testing strips separate from one another and combined with a common holding region.

7. The system of claim 6, wherein the plurality of lateral flow testing strips are arranged to test for indicators of different conditions in bodily fluid.

8. The system of claim 1, wherein the one or more lateral flow testing strips is arranged to detect the presence of indicators of one or more drugs in bodily fluid applied the one or more lateral flow testing strips.

9. The system of claim 1, wherein the bodily fluid is urine.

10. The system of claim 1, wherein the one or more processors are further configured to:
determine whether one or more lines are present in the at least one respective analysis region of the one or more lateral flow testing strips when performing the testing of the bodily fluid.

11. The system of claim 10, wherein the one or more processors are further configured to:
output a positive result that indicators are present in the bodily fluid for each lateral flow testing strip for which a predetermined test line appears in the at least one respective analysis region; and
output a negative result that indicators are not present in the bodily fluid for each lateral flow testing strip for which a predetermined test line does not appear in the at least one respective analysis region.

12. The system of claim 10, wherein the one or more processors are further configured to determine the intensity of the one or more lines in response to determining that a predetermined test line is present.

13. The system of claim 1, wherein before acquiring image data, the one or more processors are further configured to:
display a live image of the bodily fluid testing equipment on a display of the electronic device using the camera of the electronic device; and display a window on the display of the electronic device with the live image, wherein the bodily fluid testing equipment is alignable in the window.

14. The system of claim 13, wherein the one or more processors are further configured to:
automatically capture the image data of the bodily fluid testing equipment in response to identifying that the bodily fluid testing equipment is aligned in the window.

15. The system of claim 1, wherein the one or more processors are further configured to determine the position of the at least one respective analysis region of the one or more lateral flow testing strips based upon the determined position of the QR code and determined positions of one or more anchor points and/or an anchor bar arranged on the bodily fluid testing equipment.

16. The system of claim 15, wherein the QR code is arranged on the first surface of the body portion.

17. The system of claim 15, wherein the body portion further comprises one or more application-detectable anchor points arranged on the first surface of the body portion, and wherein the one or more processors are further configured to determine positions of the one or more anchor points in the image data.

18. The system of claim 17, wherein the one or more anchor points comprise a plurality of anchor points positioned proximal to the at least one respective analysis region, and wherein one of the anchor points is distinct from the other anchor points.

19. A method of testing bodily fluid in a lateral flow bodily fluid testing system, the method comprising:
acquiring, by a camera of an electronic device, image data of an application-analysable bodily fluid testing equipment comprising a body portion, a QR code on the body portion, and one or more lateral flow testing strips combined with a first surface of the body portion, the one or more lateral flow testing strips having a predetermined displacement from the QR code, the one or more lateral flow testing strips being sensitive to indicators of bodily conditions in bodily fluid, and wherein the one or more lateral flow testing strips each comprise at least one respective fluid uptake region connected to at least one respective analysis region;
determining, by the electronic device, a position of the QR code in the image data;
determining, by the electronic device, a position of the at least one respective analysis region of the one or more lateral flow testing strips using the predetermined displacement based upon the determined position of the QR code;
performing, by the electronic device, testing of bodily fluid applied to the bodily fluid testing equipment, using the image data at the determined position of the at least one respective analysis region, to determine whether indicators of one or more bodily conditions are present in the applied bodily fluid; and
outputting, by the electronic device, a result indicating whether the indicators of one or more bodily conditions are present in the applied bodily fluid.

20. A non-transitory computer-readable medium with instructions stored thereon that when executed by a processor cause the processor to perform the method comprising:
acquiring, by a camera of an electronic device, image data of an application-analysable bodily fluid testing equipment comprising a body portion, a QR code on the body portion, and one or more lateral flow testing strips combined with a first surface of the body portion, the one or more lateral flow testing strips having a predetermined displacement from the QR code, the one or more lateral flow testing strips being sensitive to indicators of bodily conditions in bodily fluid, and wherein the one or more lateral flow testing strips each comprise at least one respective fluid uptake region connected to at least one respective analysis region;
determining, by the electronic device, a position of the QR code in the image data;
determining, by the electronic device, a position of the at least one respective analysis region of the one or more lateral flow testing strips using the predetermined displacement based upon the determined position of the QR code;
performing, by the electronic device, testing of bodily fluid applied to the bodily fluid testing equipment, using the image data at the determined position of the at least one respective analysis region, to determine whether indicators of one or more bodily conditions are present in the applied bodily fluid; and
outputting, by the electronic device, a result indicating whether the indicators of one or more bodily conditions are present in the applied bodily fluid.

* * * * *